US007019112B1

(12) United States Patent
Slingluff et al.

(10) Patent No.: US 7,019,112 B1
(45) Date of Patent: Mar. 28, 2006

(54) PEPTIDES RECOGNIZED BY MELANOMA-SPECIFIC A1-, A2- AND A3-RESTRICTED CYTOXIC LYMPHOCYTES, AND USES THEREFOR

(75) Inventors: Craig L. Slingluff, Charlottesville, VA (US); Donald F. Hunt, Charlottesville, VA (US); Jeffrey Shabanowitz, Charlottesville, VA (US); Andrea L. Cox, Charlottesville, VA (US); Victor H. Engelhard, Charlottesville, VA (US); David Kittlesen, Charlottesville, VA (US); Jonathan Skipper, Oxford (GB); Ronald C. Hendrikson, Seattle, WA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 383 days.

(21) Appl. No.: 08/816,454

(22) Filed: Mar. 12, 1997

Related U.S. Application Data

(60) Provisional application No. 60/027,627, filed on Oct. 4, 1996, provisional application No. 60/013,972, filed on Mar. 19, 1996.

(51) Int. Cl.
 *C07K 7/06* (2006.01)
(52) U.S. Cl. .................................................... 530/328
(58) Field of Classification Search ............. 424/184.1, 424/185.1, 277.1; 530/324, 328
 See application file for complete search history.

(56) References Cited

U.S. PATENT DOCUMENTS 4,478,823 A 10/1984 Sanderson

FOREIGN PATENT DOCUMENTS

| WO | 9414459 | 7/1994 |
| WO | 9522561 | 8/1995 |
| WO | 9525122 | 9/1995 |
| WO | 9529193 | * 11/1995 |
| WO | 9740156 | 10/1997 |
| WO | 9833810 | 8/1998 |

OTHER PUBLICATIONS

Burgess et al. J of Cell Bio. 111:2129-2138, 1990.*
Lazar et al. Molecular and Cellular Biology 8:1247-1252 (1988).*
Tao et al., The Journal of Immunology, 143:2595-2601 (1989).*
Bowie et al (Science, 247:1306-1310, 1990.*
Yamshchikov, G, et al, 2001, Analysis of a natural immune response against tumor antigens in a melanoma survivor: Lessons applicable to clinical trial evaluations, Clinical Cancer Research, vol. 7, No. 3 supplement, pp. 909s-916s.*
Bodey, B, et al, 2000, Failure of cancer vaccines: the significant limitations of this approach to immunotherapy, Anticancer Research, vol. 20, pp. 2665-2676.*
Cox, AL, et al, 1994, Identification of a peptide recognized by five melanoma-specific human cytotoxic T cell lines, Science, vol. 264, pp. 716-719.*
Ezzell, C, 1995, Cancer "vaccines": an idea whose time has come?, Journal of NIH Research, vol. 7, pp. 46-49.*
Splitler, LE, 1995, Cancer vaccines: the interferon analogy, Cancer Biotherapy, vol. 10, No. 1, pp. 1-3.*
Boon, T, 1992, Toward a genetic analysis of tumor rejection antigens, Advances in Cancer Research, vol. 58, pp. 177-210.*
Arceci, RJ, 1998, The potential for antitumor vaccination in acute myelogenous leukemia, Journal of Molecular Medicine, vol. 76, pp. 80-93.*
Lee, K-H, et al, 1999, Increased vaccine-specific T cell frequency after peptide-based vaccination correlates with increased susceptibility to in vitro stimulation but does not lead to tumor regression, Journal of Immunology, vol. 163, pp. 6292-6300.*
Zaks, TZ, et al, 1998, Immunization with a peptide epitope (p369-377) from HER-2/neu leads to peptide-specific cytotoxic T lymphocytes that fail to recognize HER-2/neu+ tumors, Cancer Research, vol. 58, pp. 4902-4908.*
Gao, P, et al, 2000, Tumor vaccination that enhances antitumor T-cell responses does not inhibit th growth of established tumors, Journal of Immunotherapy, vol. 23, No. 6, pp. 643-653.*
Hu, X, et al, 1996, Enhancement of cytolytic T lymphocyte precursor frequency in melanoma patients following immunization with MAGE-1 peptide, Cancer Research, vol. 56, pp. 2479-2483.*
Jaeger, E, et al, 1996, Generation of cytotoxic T-cell responses with synthetic melanoma-associated peptides in vivo, International Journal of Cancer, vol. 66, No. 2, pp. 162-169.*
Mukherji, B, et al, 1995, Induction of antigen-specific cytolytic T cells in situ in human melanoma by immunization, Proceedings of the National Academy of Science USA, vol. 92, pp. 8078-8082.*
Timmerman, JM, et al, 1999, Dendritic cell vaccines for cancer immunotherapy, Annual Review of Medicine, vol. 50, pp. 507-529.*
Tockman, MS, et al, 1992, Considerations in bringing a cancer biomarker to clinical application, Cancer Research, vol. 52, Suppl., pp. 2711s-2718s.*

(Continued)

*Primary Examiner*—Larry R. Helms
*Assistant Examiner*—Stephen L. Rawlings
(74) *Attorney, Agent, or Firm*—Fulbright & Jaworski LLP

(57) ABSTRACT

Melanoma-specific, A1- and A3-restricted CTL epitopes have been identified in tyrosinase and pMel-17, respectively, and may be used in the design of vaccines.

5 Claims, 25 Drawing Sheets

OTHER PUBLICATIONS

Gura, T, 1997, Systems for identifying drugs are often faulty, Science, vol. 278, pp. 1041-1042.*

Adema et al., Melanocyte Lineage-Specific Antigens Recognized by Monoclonal Antibodies NKI-beteb, HMB-50, and HMB-45 are Encoded by a Single cDNA., *Am. J. Path*, vol. 143, No. 6, pp. 1579-1585, Dec. 1993.

Jaeger et al., Generation of Cytotoxic T-Cell Responses with Synthetic Melanoma-Associated Peptides In VIVO: Implications for Tumor Vaccines with Melanoma-Associated Antigens, *Int. J. Cancer*, vol. 66, pp. 162-169, 1996.

Slingluff et al., Recognition of Human Melanoma Cells by HLA-A2.1-Restricted Cytotoxic T Lymphocytes is Mediated by at Least Six Shared Peptide Epitopes, *J. Immunol.*, vol. 150, No. 7, pp. 2955-2963, 1993.

Vose et al., Human Tumour Antigens Defined by Cytotoxicity and Proliferative Responses of Cultured Lymphoid Cells, *Nature*, vol. 296, pp. 359-361, Mar. 25, 1982.

Knuth et al., T-Cell-Mediated Cytotoxicity Against Autologous Malignant Melanoma: Analysis with Interleukin 2-Dependent T-Cell Cultures, *Proc. Natl. Acad. Sci. USA*, vol. 81, pp. 3511-3515, Jun. 1984.

Slingluff et al., Human T Cells Specifically Activated Against Autologous Malignant Melanoma, *Arch Surg*, vol. 122, pp. 1407-1411, Dec. 1987.

Slingluff et al., Melanoma-Specific Cytotoxic T Cells Generated from Peripheral Blood Lymphocytes, *Ann. Surg.*, vol. 210, No. 2, pp. 194-202, Aug. 1989.

Muul et al., Identification of Specific Cytolytic Immune Responses Against Autologous Tumor in Humans Bearing Malignant Melanoma, *The Journal of Immunology*, vol. 138, No. 3, pp. 989-995, Feb. 1987.

Van Den Eynde et al., Presence on a Human Melanoma of Multiple Antigens Recognized by Autologous CTL, *Int. J. Cancer*, vol. 44, pp. 634-640, 1989.

Anichini et al., Clonal Analysis of Cytotoxic T-Lymphocyte Response to Autologous Human Metastatic Melanoma, *Int. J. Cancer*, vol. 35, pp. 683-689, 1985.

Elliott et al., Naturally Processed Peptides, *Nature*, vol. 348, pp. 195-197, Nov. 15, 1990.

Townsend et al., Antigen Recognition By Class I-Restricted T Lymphocytes, *Ann. Rev. Immunol.*, vol. 7, pp. 601-624, 1989.

Hunt et al., Characterization of Peptides Bound to the Class I MHC Molecule HLA-A2.1 by Mass Spectrometry, *Science*, vol. 255, pp. 1261-1263, Mar. 6, 1992.

Van Der Bruggen et al., A Gene Encoding an Antigen Recognized by Cytolic T Lymphocytes on a Human Melanoma, *Science*, vol. 254, pp. 1643-1647, Dec. 13, 1991.

Traversari et al., A Nonapeptide Encoded by Human Gene MAGE-1 is Recognized on HLA-A1 by Cytolytic T Lymphocytes Directed against Tumor Antigen MZ2-E, *J. Exp. Med.*, vol. 176, pp. 1453-1457, Nov. 1992.

Brichard et al., The Tyrosinase Gene Codes for an Antigen Recognized by Autologous Cytolytic T Lymphocytes on HLA-A2 Melanomas, *J. Exp. Med.*, vol. 178, pp. 489-495, Aug. 1993.

Wolfel et al., Two Tyrosinase Nonapeptides Recognzied on HLA-A2 Melanomas by Autologous Cytolytic T Lymphocytes, *Eur. J. Immunol.*, vol. 24, pp. 759-763, 1994.

Boon et al., Tumor Antigens Recognized by T Lymphocytes, *Ann. Rev. Immunol.*, vol. 12, pp. 337-365, 1994.

Finn, Olivera J., Tumor-Rejection Antigens Recognized by T Lymphocytes, *Current Opinion in Immunology*, vol. 5, pp. 701-708, 1993.

Cox et al., Identification of a Peptide Recognized by Five Melanoma-Specific Human Cytotoxic T Cell . . . , *Science*, vol. 264, pp. 716-719, Apr. 1994.

Engelhard et al., Mass Spectrometric Analysis of Peptides Associated with the Human Class I MHC Molecules HLA-A2.1 and HLA-B7 and Identification of Structural Features that Determine Binding, *Chem Immunol. Basel, Karger*, vol. 57, pp. 39-62, 1993.

Kwon et al., A Melanocyte-Specific Gene, Pmel 17, Maps Near the Silver Coat Color Locus on Mouse Chromosome 10 and is in a Syntenic Region on Human Chromosome 12, *Proc. Natl. Acad. Sci., USA*, vol. 88, pp. 9228-9232, Oct. 1991.

Anichini et al., Melanoma Cells and Normal Melanocytes Share Antigens Recognized by HLA-A2-restricted Cytotoxic T Cell Clones from Melanoma Patients, *J. Exp. Med*, vol. 177, pp. 989-998, Apr. 1993.

Van Bleek et al., Isolation of an Endogenuously Processed Immunodominant Viral Peptide from the Class I $H-2K^b$ Molecule, *Nature*, vol. 348, pp. 213-216, Nov. 1990.

Kawakami et al., Identification of a Human Melanoma Antigen Recognized by Tumor-Infiltrating Lymphocytes Associated with in vivo Tumor Rejection, *Proc. Natl. Acad. Sci. USA*, vol. 91, pp. 6458-6462, Jul. 1994.

Kawakami et al., Cloning of the Gene Coding for a Shared Human Melanoma Antigen Recognized by Autologous T Cells Infiltrating into Tumor, *Proc. Natl. Acad. Sci. USA*, vol. 91, pp. 3515-3519, Apr. 1994.

Mandelbolm et al., CTL Induction by a Tumour-Associated Antigen Octapeptide Derived from a Murine Lung Carcinoma, *Nature*, vol. 369, pp. 67-71, May 1994.

Henderson et al., Direct Identification of an Endogenous Peptide Recognized by Multiple HLA-A2.1-Specific Cytotoxic T Cells, *Proc. Natl. Acad. Sci. USA*, vol. 90, pp. 10275-10279, Nov. 1993.

Huczko et al., Characteristics of Endogenous Peptides Eluted fromt he Class I MHC Molecule HLA-B7 Determined by Mass Spectrometry and Computer Modeling, *The Journal of Immunology*, vol. 151, pp. 2572-2587, Sep. 1993.

Kast et al., Role of HLA-A Motifs in Identification of Potential CTL Epitopes in Human Papillomavirus Type 16 E6 and E7 Proteins, *The Journal of Immunology*, vol. 152, No. 8, pp. 3904-3912, Apr. 1994.

Kawakami et al., Recognition of Multiple Epitopes in the Human Melanoma Antigen gp100 by Tumor-Infiltrating T Lymphocytes Associated with In Vivo Tumor Regression, *The Journal of Immunology*, vol. 154, No. 8, pp. 3961-3968, Apr. 1995.

Estin et al., Recombinant Vaccinia Virus Vaccine Against the Human Melanoma Antigen p97 for Use in Immunotherapy, *Proc. Natl. Acad. Sci. USA*, vol. 85, pp. 1052-1056, Feb. 1988.

Kwon et al., Melanocyte-Specific Complementary DNA Clone whose Expression is Inducible by Melanotropin and Isobutylmethyl Xanthine, *Molecular Biology and Medicine*, vol. 4, pp. 339-355, Dec. 1987.

Bodmer et al., Anti-HLA-A2 Antibody-Enhancement of Peptide Association with HLA-A2 as Detected by Cytotoxic T Lymphocytes, *Nature*, vol. 342, pp. 443-446, Nov. 1989.

Bednarek et al., Minimum Peptide Epitope from the Influenza Virus Matrix Protein: Extra and Intracellular Loading of HLA-A2, *J. of Immunology*, vol. 147, pp. 4047-4053, Dec. 1991.

Oetting et al., Molecular Analysis of an Extended Family with Type 1A (Tyrosinase-negative) Oculocutaneous Albinism, *J. of Investigative Dermatology*, vol. 97, pp. 15-19, Jul. 1991.

Hearing et al., Analysis of Mammalian Pigmentation at the Molecular Level, *Pigment Cell Research*, vol. 2, pp. 75-85, Mar./Apr. 1989.

Chen et al., Naturally Processed Peptides Longer than Nine Amino Acid Residues Bind to the Class I MHC Molecule HLA-A2.1 with High Affinity and in Different Conformations, *J. of Immunology*, vol. 152, pp. 2874-2881, Mar. 1994.

Udaka et al., Naturally Occurring Peptide Recognized by Alloreactive CD8+ Cytotoxic T Lymphocytes in Association with a Class I MHC Protein, *Cell*, vol. 69, pp. 989-998, Jun. 1992.

Falk et al., Identification of Naturally Processed Viral Nonapeptides Allows their Quantification in Infected Cells and Suggests an Allele-specific T Cell Epitope Forecast, *J. of Experimental Medicine*, vol. 174, pp. 425-434, Aug. 1991.

Gaugler et al., Human Gene MAGE-3 Codes for an Antigen Recognized on a Melanoma by Autologous Cytolytic T Lymphocytes, *J. of Experimental Medicine*, vol. 179, pp. 921-930, Mar. 1994.

Bakker et al., Melanocyte Lineage-specific Antigen gp100 Is Recognized by Melanoma-derived Tumor-infiltrating Lymphocytes, *J. of Experimental Medicine*, vol. 179, pp. 1005-1009, Mar. 1994.

Coulie et al., New Gene Coding for a Differentiation Antigen Recognized by Autologous Cytolytic T Lymphocytes on HLA-A2 Melanomas, *J. of Experimental Medicine*, vol. 180, pp. 35-42, Jul. 1994.

Kawakami et al., Identification of the Immunodominant Peptides of the MART-1 Human Melanoma Antigen Recognized by the Majority of HLA-A2-restricted Tumor Infiltrating Lymphocytes, *J. of Experimental Medicine*, vol. 180, pp. 347-352, Jul. 1994.

Ruppert et al., Prominent Role of Secondary Anchor Residues in Peptide Binding to HLA-A2.1 Molecules, *Cell*, vol. 74, pp. 929-937, Sep. 1993.

Madden et al., Antigenic Identity of Peptide-MHC Complexes: a Comparison of the Conformations of Five Viral Peptides Presented by HLA-A2, *Cell*, vol. 75, pp. 693-708, Nov. 1993.

Hobohm et al., Pattern Search Method for Putative Anchor Residues in T Cell Epitopes, *European J. of Immunology*, vol. 23, pp. 1271-1276, Jun. 1993.

Lathe et al., Tumour Prevention and Rejection with Recombinant Vaccinia, *Nature*, vol. 326, pp. 878-880, Apr. 1987.

Bernards et al., Effective Tumor Immunotherapy Directed Against an Oncogene-encoded Product Using a Vaccinia Virus Vector, *Proc. of the Natl Acad Sci. USA*, vol. 84, pp. 6854-6858, Oct. 1987.

Bertoletti et al., Definition of a Minimal Optimal Cytotoxic T-cell Epitope within the Hepatitis B Viral Nucleocapsid Protein, *J. of Virology*, vol. 67, pp. 2376-2380, Apr. 1993.

Bouchard et al., Induction of Pigmentation in Mouse Fibroblasts by Expression of Human Tyrosinase cDNA, *J. of Experimental Medicine*, vol. 169, pp. 2029-2042, Jun. 1989.

Suzuki et al., Identification of Peptide: N-glycanase Activity in Mammalian-derived Cultured Cells, *Biochemical and Biophysical Research Communications*, vol. 194, pp. 1124-1130, Aug. 1993.

Suzuki et al., Purification and Enzymatic Properties of Peptide: N-glycanase from C3H Mouse-derived L-929 Fibroblast Cells, *J. of Biological Chemistry*, vol. 269, pp. 17611-17618, Jul. 1994.

Aronson et al., Lysosomal Degradation of Asn-linked Glycoproteins, *FASEB J.*, vol. 3, pp. 2615-2622, Dec. 1989.

Kaartinen et al., Substrate Specificity and Reaction Mechanism of Human Glycoasparaginase, *J. of Biological Chemistry*, vol. 267, pp. 6855-6858, Apr. 1992.

Mononen et al., Aspartylglycosaminuria: Protein Chemistry and Molecular Biology of the Most Common Lysosomal Storage Disorder of Glycoprotein Degradation, *FASEB J.*, vol. 7, pp. 1247-1256, Oct. 1993.

Hearing et al., Mammalian Tyrosinase—the Critical Regulatory Control Point in Melanocyte Pigmentation, *International J. of Biochemistry*, vol. 19, pp. 1141-1147, 1987.

Ohkura et al., Purification of Hamster Melanoma Tyrosinases and Structural Studies of their Asparagine-linked Sugar Chains, *Archives of Biochemistry and Biophysics*, vol. 235, pp. 63-77, Nov. 1984.

Darrow et al., Autologous Lymph Node Cell-Derived Tumor-Specific Cytotoxic T-Cells for Use in Adoptive Immunotherapy of Human Melanoma, *Cancer*, vol. 62, pp. 84-91, 1988.

Rock et al., Peptide-Priming of Cytolytic T Cell Immunity In Vivo Using $\beta_2$-Microglobulin as an Adjuvant, *The Journal of Immunology*, vol. 150, No. 4, pp. 1244-1252, Feb. 1993.

Chintamaneni, et al., A single base insertion in the putative transmembrane domain of the tyrosinase gene as a cause for tyrosinase-negative oculocutaneous albinism, Proc. Natl. Acad. Sci. USA, vol. 88, pp. 5272-5276, Jun. 1991.

Kesari, et al., *A Single Amino Acid Substitution in the H-2Kb Molecule Generates a Defined Allogeneic Epitope*, Molecular Immunology, vol. 30, No. 18, pp. 1671-1677, 1993.

Poindexter, et al., *Isolation of a Kidnew-Specific Peptide Recognized by Alloreactive HLA-A3-Restricted Human CTL*, Journal of Immunology, vol. 154, No. 8, pp. 3880-3887, 1995.

* cited by examiner

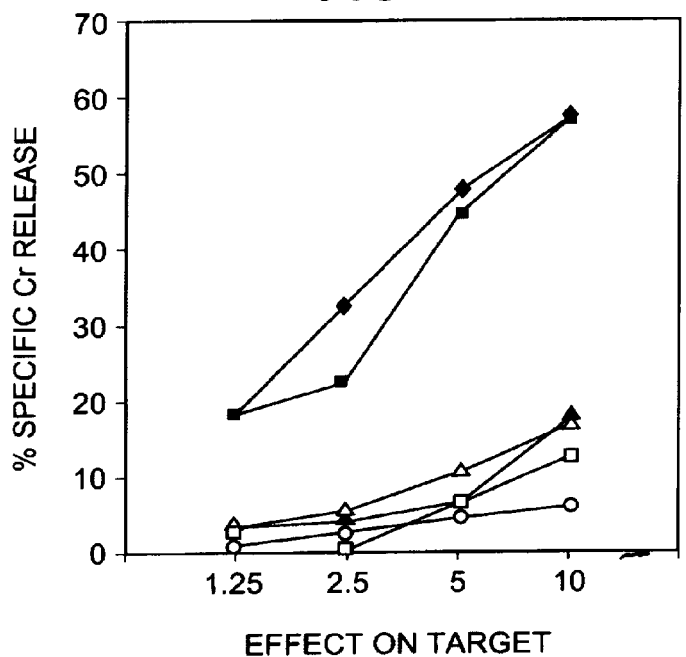
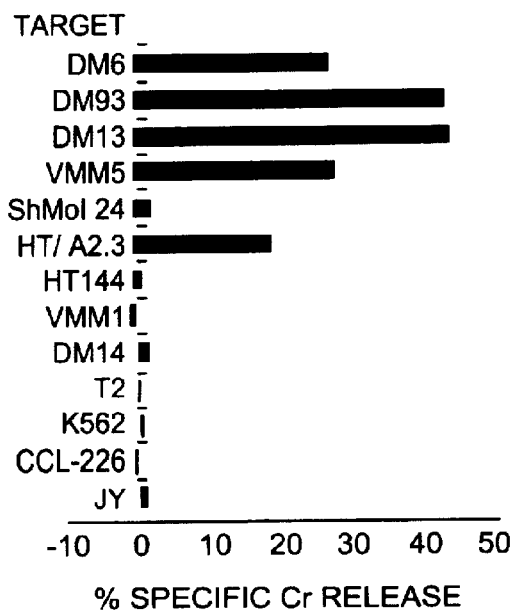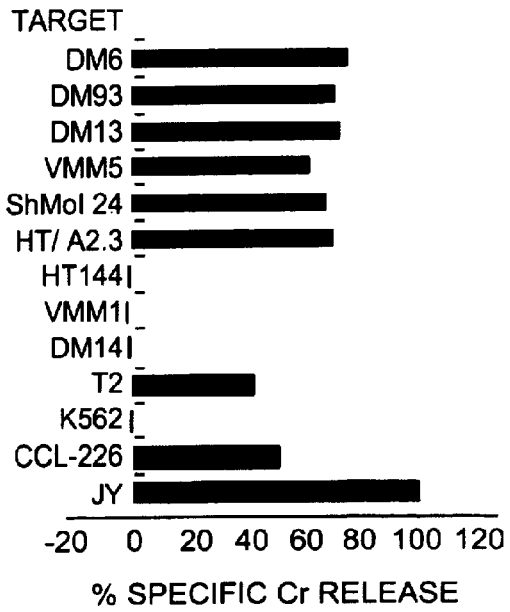

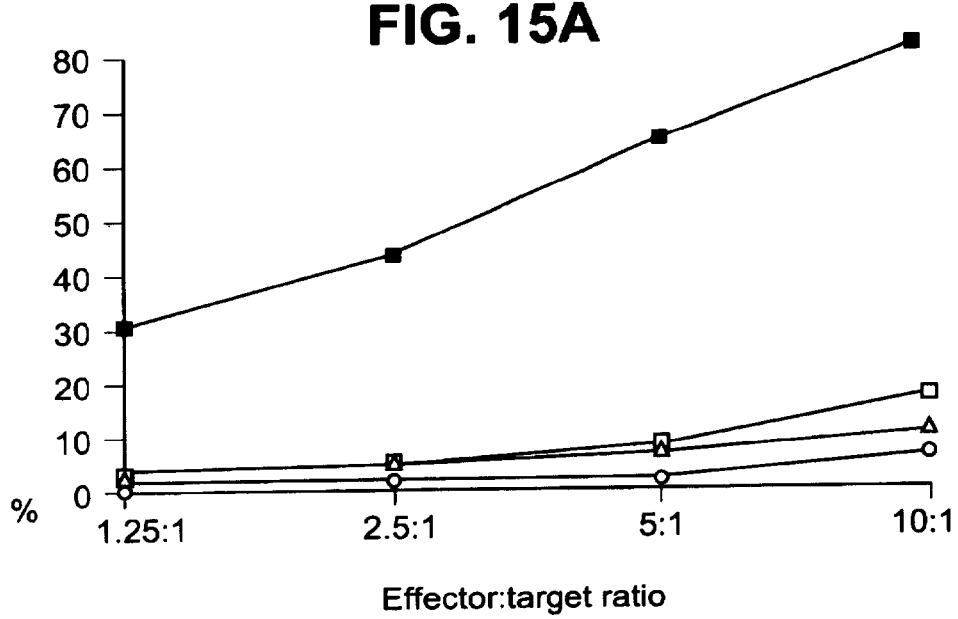
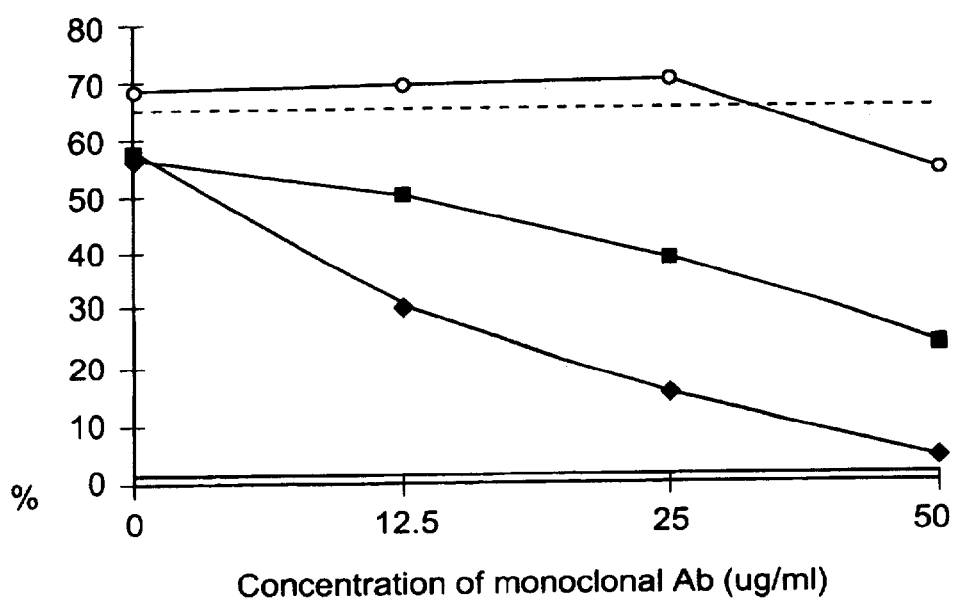

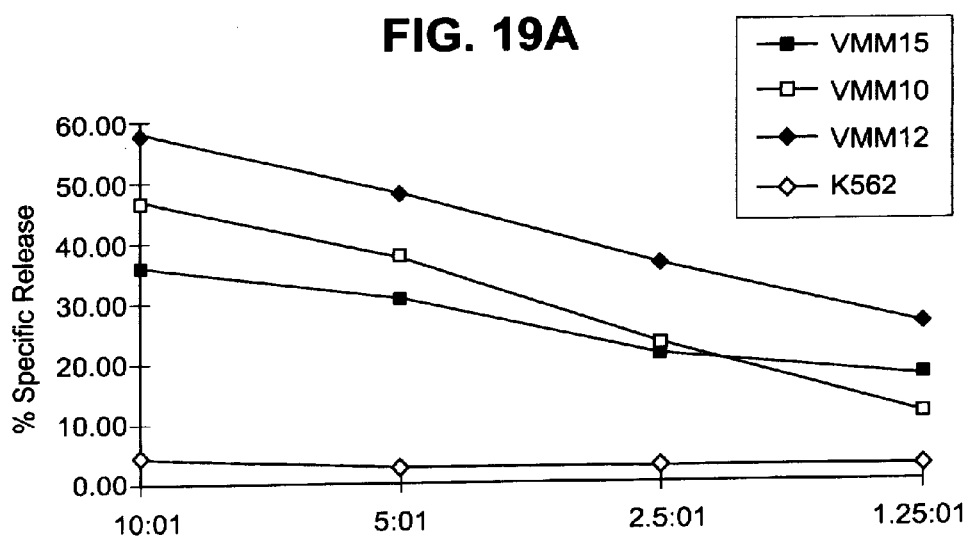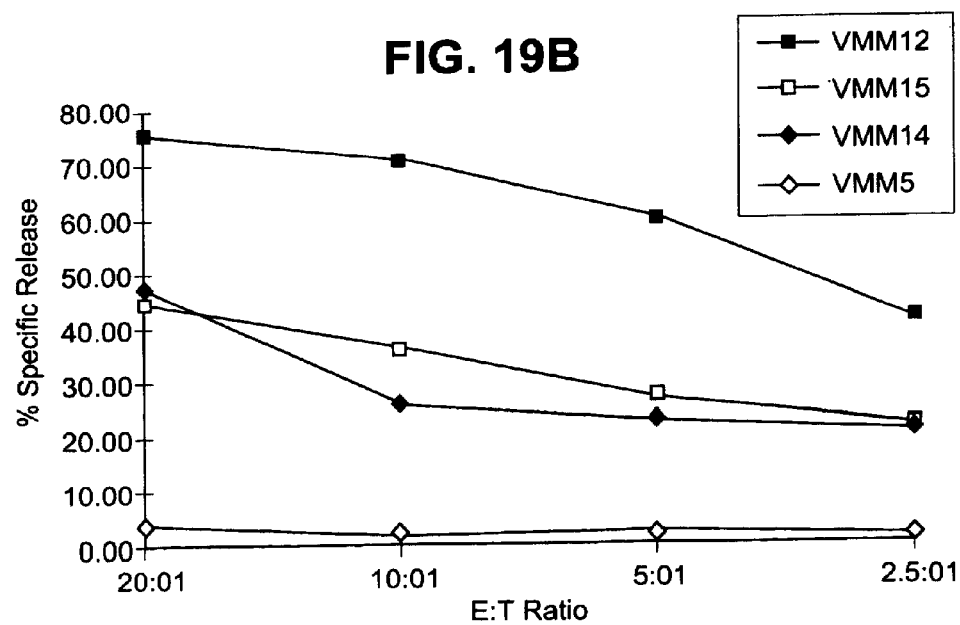

FIG. 21A

| 1st synthesis | 2/15, 2/22 and those tested | 2/29 #? | those in 3Ti | SEQ ID NO: |
|---|---|---|---|---|
| AKHTISSDY | AKHTISSDY | 20 | AKHTISSDY 21 | 161 |
| APEKDKFFAY | APEKDKFFAY | 9 | | 162 |
| | APVVTHTY | 35 | | 163 |
| DLFVWIHYY | DLFVWIHYY | 22 | DLFVWIHYY (diff seq) | 164 |
| DLFVWMHIY | DLFVWMHIY | 23 | DLFVWMHIY(diff seq) | 165 |
| DRESWPSVFY | DRESWPSVFY | 8 | DRESWPSVFY | 166 |
| DSDPDSFQDY | DSDPDSFQDY | 3 | | 167 |
| DSFQDYIKSY | DSFQDYIKSY | 4 | | 168 |
| DYVIPIGTY | DYVIPIGTY | 21 | DYVIPIGTY 22 | 169 |
| EFCLSLTQY | EFCLSLTQY | 26 | EFCLSLTQY 27 | 170 |
| EKEDYHSLY | EKEDYHSLY | 16 | | 171 |
| FISSKDLGY | FISSKDLGY | 17 | | 172 |
| FQDYIKSY | FQDYIKSY | 33 | | 173 |
| GDENFTIPY | GDENFTIPY | 15 | GDENFTIPY 15 | 174 |
| ISSKDLGYDY | ISSKDLGYDY | 2 | | 175 |
| IVCSRLEEY | IVCSRLEEY | 25 | IVCSRLEEY 26 | 176 |
| IYDLFVWMHY | IYDLFVWMHY | 5 | IYDLFVWMHY 5 | 177 |
| KCDICTDEY | KCDICTDEY | 11 | KCDICTDEY 12 | 178 |
| KDLGYDYSY | KDLGYDYSY | 29 | | 179 |
| KEDYHSLY | KEDYHSLY | 34 | | 180 |
| PEKDKFFAY | PEKDKFFAY | 19 | | 181 |
| PIGHNRESY | PIGHNRESY | 28 | | 182 |
| PLLMEKEDY | PLLMEKEDY | 32 | | 183 |
| PMFNDINIY | PMFNDINIY | 10 | PMFNDINIY 11 | 184 |
| RESWPSVFY | RESWPSVFY | 18 | | 185 |
| RHRPLQEVY | RHRPLQEVY | 27 | | 186 |
| SDPDSFQDY | SDPDSFQDY | 30 | | 187 |
| SFQDYIKSY | SFQDYIKSY | 31 | | 188 |
| SKDLGYDY | SKDLGYDY | 36 | | 189 |
| SKDLGYDYSY | SKDLGYDYSY | 7 | | 190 |
| SMDALLGGY | SMDALLGGY | 24 | SMDALLGGY(diff seq) | 191 |
| SMHNALHIY | SMHNALHIY | 12 | SMHNALHIY 13 | 192 |
| SSKDLGYDY | SSKDLGYDY | 14 | | 193 |
| SSMHNALHIY | SSMHNALHIY | 1 | SSMHNALHIY 1 | 194 |
| TGDENFTIPY | TGDENFTIPY | 6 | TGDENFTIPY 7 | 195 |
| YMVPFIPLY | YMVPFIPLY | 13 | | 196 |

FIG. 21B

| | | | SEQ ID NO: |
|---|---|---|---|
| ANAPIGHNRESY | ANAPIGHNRESY | | 197 |
| APIGHNRESY | APIGHNRESY | | 198 |
| DAEKCDICTDEY | DAEKCDICTDEY | 3 DAEKCDICTDEY | 199 |
| DLFVWMHYY | DLFVWMHYY | 4 DLFVWMHYY | 200 |
| DPDSFQDYIKSY | DPDSFQDYIKSY | | 201 |
| DVEFCLSLTQY | DVEFCLSLTQY | 6 DVEFCLSLTQY | 202 |
| EKCDICTDEY | EKCDICTDEY | 7 EKCDICTDEY | 203 |
| ESYMVPFIPLY | ESYMVPFIPLY | | 204 |
| FFISSKDLGY | FFISSKDLGY | | 205 |
| FISSKDLGYDY | FISSKDLGYDY | | 206 |
| GDEDFTIPY | GDEDFTIPY | 11 GDEDFTIPY (n to d) | 207 |
| GSTPMFNDINIY | GSTPMFNDINIY | 12 GSTPMFNDINIY | 208 |
| ISSDYVIPIGTY | ISSDYVIPIGTY | 13 ISSDYVIPIGTY | 209 |
| ISSKDLGYDYSY | ISSKDLGYDYSY | | 210 |
| IYDLFVWIHY | IYDLFVWIHY | 15 IYDLFVWIHY (seq. diff.) | 211 |
| IYDLFVWIHYY | IYDLFVWIHYY | 16 IYDLFVWIHYY (seq. diff.) | 212 |
| IYDLFVWMHYY | IYDLFVWMHYY | 17 IYDLFVWMHYY | 213 |
| LAKHTISSDY | LAKHTISSDY | 18 LAKHTISSDY (partial) | 214 |
| LMEKEDYHSLY | LMEKEDYHSLY | | 215 |
| LQDSDPDSFQDY | LQDSDPDSFQDY | | 216 |
| LSAPEKDKFFAY | LSAPEKDKFFAY | | 217 |
| LTGDEDFTIPY | LTGDEDFTIPY | 22 LTGDEDFTIPY (n to d) | 218 |
| LTGDENFTIPY | LTGDENFTIPY | 23 LTGDENFTIPY | 219 |
| LTLAKHTISSDY | LTLAKHTISSDY | 24 LTLAKHTISSDY (partial) | 220 |
| MEKEDYHSLY | MEKEDYHSLY | | 221 |
| PDSFQDYIKSY | PDSFQDYIKSY | | 222 |
| QDSDPDSFQDY | QDSDPDSFQDY | | 223 |
| QIVCSRLEEY | QIVCSRLEEY | 25 QIVCSRLEEY | 224 |
| QPLLMEKEDY | QPLLMEKEDY | | 225 |
| QRHRPLQEVY | QRHRPLQEVY | | 226 |
| QSSMHNALHIY | QSSMHNALHIY | 31 QSSMHNALHIY | 227 |
| RESYMVPFIPLY | RESYMVPFIPLY | | 228 |
| RRHRPLQEVY | RRHRPLQEVY | | 229 |
| SDYVIPIGTY | SDYVIPIGTY | 34 SDYVIPIGTY | 230 |
| SQSSMHNALHIY | SQSSMHNALHIY | 35 SQSSMHNALHIY | 231 |
| SSDYVIPIGTY | SSDYVIPIGTY | 36 SSDYVIPIGTY | 232 |
| SSKDLGYDYSY | SSKDLGYDYSY | | 233 |
| STPMFNDINIY | STPMFNDINIY | 38 STPMFNDINIY | 234 |
| SYMVPFIPLY | SYMVPFIPLY | | 235 |
| TGDEDFTIPY | TGDEDFTIPY | 40 TGDEDFTIPY (n to d) | 236 |
| TLAKHTISSDY | TLAKHTISSDY | 41 TLAKHTISSDY (partial) | 237 |
| TPMFNDINIY | TPMFNDINIY | 42 TPMFNDINIY | 238 |
| VDDRESWPSVFY | VDDRESWPSVFY | | 239 |
| VEFCLSLTQY | VEFCLSLTQY | 44 VEFCLSLTQY | 240 |
| VSMDALLGGY | VSMDALLGGY | 45 VSMDALLGGY (seq. diff.) | 241 |
| YVSMDALLGGY | YVSMDALLGGY | 46 YVSMDALLGGY (seq. diff.) | 242 |

FIG. 21C

| 3rd synthesis | those tested | those in 3TI | SEQ ID NO: |
|---|---|---|---|
| AMERPRDLY | | ? | 243 |
| EVSTPQILTY | | ? | 244 |
| ITTACIRAIY | | ? | 245 |
| IWAMTIAIY | | ? | 246 |
| RSTTAISLY | | ? | 247 |
| TTACIRAIY | | ? | 248 |
| VSTPQILTY | | ? | 249 |
| WRSTTAISLY | | ? | 250 |
| YDLFVWIHY | | YDLFVWIHY (seq. diff) | 251 |
| YDLFVWIHYY | | YDLFVWIHYY (seq. diff) | 252 |
| YDLFVWMHY | | YDLFVWMHY | 253 |
| YDLFVWMHYY | | YDLFVWMHYY | 254 |

FIG. 21D

| 4th synthesis | # | 4th synthesis | those in 3TI | SEQ ID NO: |
|---|---|---|---|---|
| ANDPIFLLH | 3 | ANDPIFLLH | | 255 |
| ANDPIFLLHH | 4 | ANDPIFLLHH | | 256 |
| CCPPWSGDR | 32 | CCPPWSGDR | | 257 |
| CTDEYMGGQ | 21 | CTDEYMGGQ | CTDEYMGGQ | 258 |
| CTDEYMGGQH | 24 | CTDEYMGGQH | CTDEYMGGQH | 259 |
| CTERRLLVR | 2 | CTERRLLVR | | 260 |
| CTERRLLVRR | 7 | CTERRLLVRR | | 261 |
| CVSSKNLMEK | 35 | CVSSKNLMEK | | 262 |
| DGTPEGPLRR | 25 | DGTPEGPLRR | DGTPEGPLRR (n to d) | 263 |
| DIDFAHEAPA | 36 | DIDFAHEAPA | DIDFAHEAPA | 264 |
| DPDSFQDYIK | 5 | DPDSFQDYIK | | 265 |
| DSDPDSFQD | 10 | DSDPDSFQD | | 266 |
| DVEFCLSLTQ | 8 | DVEFCLSLTQ | DVEFCLSLTQ | 267 |
| ECCPPWSGDR | 37 | ECCPPWSGDR | | 268 |
| FNDINIYDLF | 26 | FNDINIYDLF | FNDINIYDLF | 269 |
| FTIPYWDWR | 12 | FTIPYWDWR | FTIPYWDWR | 270 |
| GSEIWRDIDF | 1 | GSEIWRDIDF | GSEIWRDIDF | 271 |
| GTPEGPLRR | 22 | GTPEGPLRR | GTPEGPLRR | 272 |
| GYEIWRDIDF | 16 | GYEIWRDIDF | GYEIWRDIDF (seq. change) | 273 |
| IFDLSAPEK | 33 | IFDLSAPEK | | 274 |
| LPEEKQPLLM | 30 | LPEEKQPLLM | | 275 |
| LSAPEKDKF | 18 | LSAPEKDKF | | 276 |
| LSAPEKDKFF | 20 | LSAPEKDKFF | | 277 |
| NGDFFISSK | 13 | NGDFFISSK | | 278 |
| NGTPEGPLRR | 27 | NGTPEGPLRR | NGTPEGPLRR | 279 |
| QTSAGHFPR | 23 | QTSAGHFPR | | 280 |
| QYESGSMDK | 6 | QYESGSMDK | QYESGSMDK | 281 |
| SADVEFCLSL | 14 | SADVEFCLSL | SADVEFCLSL | 282 |
| SMDKAADFSF | 28 | SMDKAADFSF | SMDKAADFSF (n to d) | 283 |
| SMDKAANFSF | 29 | SMDKAANFSF | SMDKAANFSF | 284 |
| SSDYVIPIG | 19 | SSDYVIPIG | SSDYVIPIG | 285 |
| SSDYVIPIGT | 11 | SSDYVIPIGT | SSDYVIPIGT | 286 |
| TLEGFASPLT | 17 | TLEGFASPLT | TLEGFASPLT | 287 |
| YLEQASRIWS | 9 | YLEQASRIWS | | 288 |
| YMVPFIPLYR | 15 | YMVPFIPLYR | | 289 |
| YPEANAPIGH | 31 | YPEANAPIGH | | 290 |
| YWDWRDAEK | 34 | YWDWRDAEK | YWDWRDAEK | 291 |

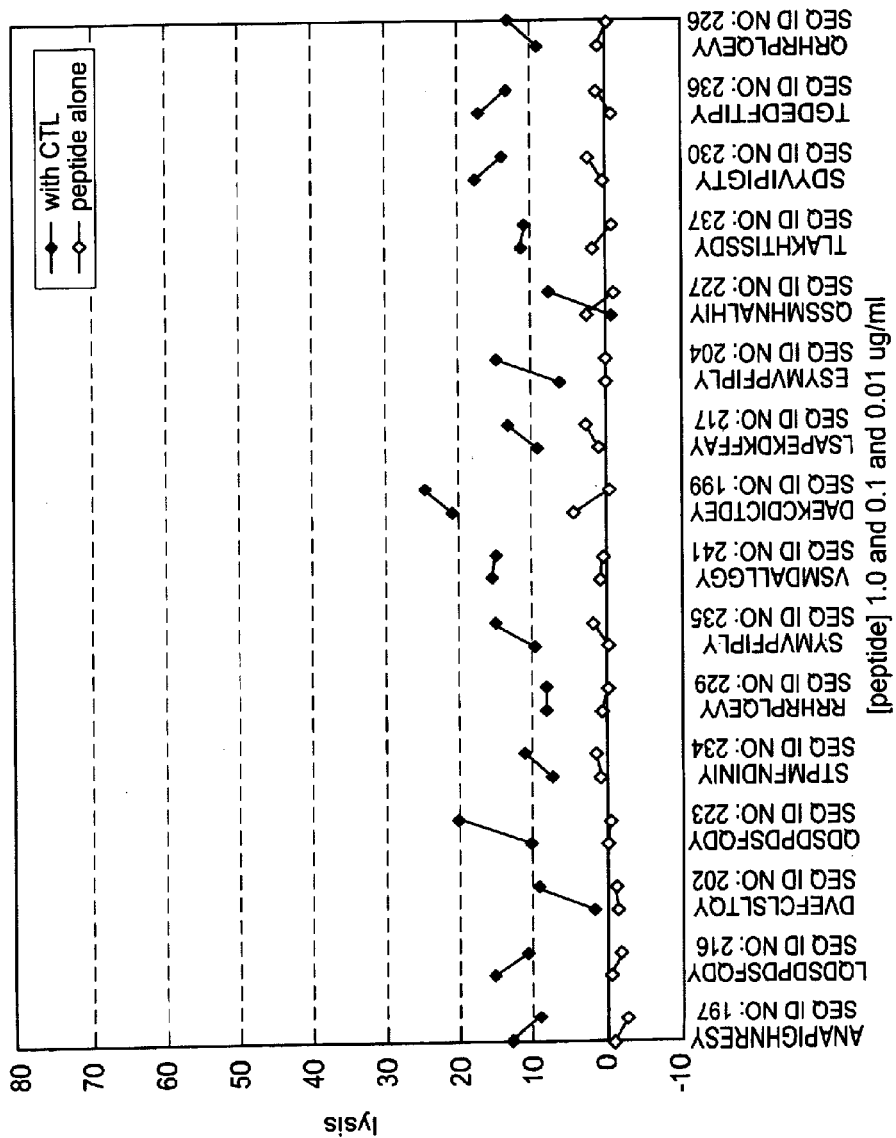

FIG. 24

```
  1  MLLAVLYCLL  WSFQTSAGHF  PRACVSSKNL  MEKECCPPWS  GDRSPCGQLS
 51  GRGSCQNILL  SNAPLGPQFP  FTGVDDRESW  PSVFYNRTCQ  CSGNFMGFNC
101  GNCKFGFWGP  NCTERRLLVR  RNIFDLSAPE  KDKFFAYLTL  AKHTISSDYV
151  IPIGTYGQMK  NGSTPMFNDI  NIYDLFVWMH  YYVSMDALLG  GSEIWRDIDF
201  AHEAPAFLPW  HRLFLLRWEQ  EIQKLTGDEN  FTIPYWDWRD  AEKCDICTDE
251  YMGGQHPTNP  NLLSPASFFS  SWQIVCSRLE  EYNSHQSLCN  GTPEGPLRRN
301  PGNHDKSRTP  RLPSSADVEF  CLSLTQYESG  SMDKAANFSF  RNTLEGFASP
351  LTGIADASQS  SMHNALHIYM  NGTMSQVQGS  ANDPIFLLHH  AFVDSIFEQW
401  LQRHRPLQEV  YPEANAPIGH  NRESYMVPFI  PLYRNGDFFI  SSKDLGYDYS
451  YLQDSDPDSF  QDYIKSYLEQ  ASRIWSWLLG  AAMVGAVLTA  LLAGLVSLLC
501  RHKRKQLPEE  KQPLLMEKED  YHSLYQSHL   (SEQ ID NO: 292)
```

KCDICTDEY represents residues 243-251 of the tyrosinase sequence

| | | | |
|---|---|---|---|
| 17/529 Residues are Cysteine | = 3.2% | 2/9 Residues of KCDICTDEY are Cysteine | = 22% |
| 30/529 Residues are Aspartic acid | = 5.7% | 2/9 Residues of KCDICTDEY are Asp Acid | = 22% |
| 27/529 Residues are Glutamic acid | = 5.1% | 3/9 Residues of KCDICTDEY are Glutamic acid | = 11% |
| 17/529 Residues are Lysine | = 3.2% | 1/9 Residues of KCDICTDEY are Cysteine | = 11% |
| Total of C-D-E-K | = 17.2% | | = 67% |

SEQUENCE LISTING (1) GENERAL INFORMATION:

(iii) NUMBER OF SEQUENCES: 294

(2) INFORMATION FOR SEQ ID NO: 1:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Asp Leu Val Leu Lys Arg Cys Leu Leu
1               5

(2) INFORMATION FOR SEQ ID NO: 2:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Leu Leu His Leu Ala Val Ile Gly Ala
1               5

(2) INFORMATION FOR SEQ ID NO: 3:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 3:

His Leu Ala Val Ile Gly Ala Leu Leu
1               5

(2) INFORMATION FOR SEQ ID NO: 4:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 4:

Leu Leu Ala Val Gly Ala Thr Lys
1               5

(2) INFORMATION FOR SEQ ID NO: 5:

(i) SEQUENCE CHARACTERISTICS:
       (A) LENGTH: 9 amino acids
       (B) TYPE: amino acid
       (C) STRANDEDNESS: single
       (D) TOPOLOGY: linear

```
        (ii) MOLECULE TYPE: peptide (xi) SEQUENCE DESCRIPTION: SEQ ID NO: 5:

Gln Leu Tyr Pro Glu Trp Thr Glu Ala
1               5

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Val Ile Trp Val Asn Asn Thr Ile Ile
1               5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Val Leu Gly Gly Pro Val Ser Gly Leu
1               5

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Gly Leu Ser Ile Gly Thr Gly Arg Ala
1               5

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Tyr Met Asp Gly Thr Met Ser Gln Val
1               5

(2) INFORMATION FOR SEQ ID NO: 10:

(i) SEQUENCE CHARACTERISTICS:
        (A) LENGTH: 9 amino acids
        (B) TYPE: amino acid
        (C) STRANDEDNESS: single
```

```
        (D) TOPOLOGY: linear (ii) MOLECULE TYPE: peptide (xi) SEQUENCE DESCRIPTION: SEQ ID NO: 10:

Ser Ile Gly Thr Gly Arg Ala Met Leu
1               5

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Met Leu Gly Thr His Thr Met Glu Val
1               5

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Gln Leu His Asp Pro Ser Gly Tyr Leu
1               5

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Thr Leu Ile Ser Arg Ala Pro Val Val
1               5

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Tyr Leu Glu Pro Gly Pro Val Thr Ala
1               5

(2) INFORMATION FOR SEQ ID NO: 15:

(i) SEQUENCE CHARACTERISTICS:
        (A) LENGTH: 9 amino acids
        (B) TYPE: amino acid
```

```
            (C) STRANDEDNESS: single
            (D) TOPOLOGY: linear (ii) MOLECULE TYPE: peptide (xi) SEQUENCE DESCRIPTION: SEQ ID NO: 15:

Gly Met Thr Pro Glu Lys Val Pro Val
1               5

(2) INFORMATION FOR SEQ ID NO: 16:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Gly Met Thr Pro Ala Glu Val Ser Ile
1               5

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Ser Ile Thr Gly Ser Leu Gly Pro Leu
1               5

(2) INFORMATION FOR SEQ ID NO: 18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 18:

Pro Leu Leu Asp Gly Thr Ala Thr Leu
1               5

(2) INFORMATION FOR SEQ ID NO: 19:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 19:

Thr Leu Arg Leu Val Lys Arg Gln Val
1               5

(2) INFORMATION FOR SEQ ID NO: 20:

(i) SEQUENCE CHARACTERISTICS:
            (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Arg Leu Val Lys Arg Gln Val Pro Leu
1               5

(2) INFORMATION FOR SEQ ID NO: 21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Asp Ile Val Gln Gly Ile Glu Ser Ala
1               5

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Val Leu Pro Ser Pro Ala Cys Gln Leu
1               5

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Ser Leu Ala Asp Thr Asn Ser Leu Ala
1               5

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Ser Leu Ala Val Val Ser Thr Gln Leu
1               5

(2) INFORMATION FOR SEQ ID NO: 25:

(i) SEQUENCE CHARACTERISTICS:
```

(A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Gln Leu Ile Met Pro Val Pro Gly Ile
1               5

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Leu Ile Met Pro Val Pro Gly Ile Leu
1               5

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Ile Met Pro Val Pro Gly Ile Leu Leu
1               5

(2) INFORMATION FOR SEQ ID NO: 28:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Gly Ile Leu Leu Thr Gly Gln Glu Ala
1               5

(2) INFORMATION FOR SEQ ID NO: 29:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Leu Leu Thr Gly Gln Glu Ala Gly Leu
1               5

(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Gly Leu Gly Gln Val Pro Leu Ile Val
1               5

(2) INFORMATION FOR SEQ ID NO: 31:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Pro Leu Ile Val Gly Ile Leu Leu Val
1               5

(2) INFORMATION FOR SEQ ID NO: 32:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Leu Ile Val Gly Ile Leu Leu Val Leu
1               5

(2) INFORMATION FOR SEQ ID NO: 33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Gly Ile Leu Leu Val Leu Met Ala Val
1               5

(2) INFORMATION FOR SEQ ID NO: 34:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Ile Leu Leu Val Leu Met Ala Val Val
1               5

(2) INFORMATION FOR SEQ ID NO: 35:

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Leu Leu Val Leu Met Ala Val Val Leu
1               5

(2) INFORMATION FOR SEQ ID NO: 36:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Leu Met Ala Val Val Leu Ala Ser Leu
1               5

(2) INFORMATION FOR SEQ ID NO: 37:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Arg Leu Met Lys Gln Asp Phe Ser Val
1               5

(2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Pro Ile Gly Glu Asn Ser Pro Leu Leu
1               5

(2) INFORMATION FOR SEQ ID NO: 39:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Tyr Ile Glu Pro Gly Pro Val Thr Ala
1               5
```

(2) INFORMATION FOR SEQ ID NO: 40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Val Leu Lys Arg Cys Leu Leu His Leu Ala
1               5                   10
```

(2) INFORMATION FOR SEQ ID NO: 41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

```
Cys Leu Leu His Leu Ala Val Ile Gly Ala
1               5                   10
```

(2) INFORMATION FOR SEQ ID NO: 42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

```
Leu Leu His Leu Ala Val Ile Gly Ala Leu
1               5                   10
```

(2) INFORMATION FOR SEQ ID NO: 43:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

```
His Leu Ala Val Ile Gly Ala Leu Leu Ala
1               5                   10
```

(2) INFORMATION FOR SEQ ID NO: 44:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

```
Ala Leu Leu Ala Val Gly Ala Thr Lys Val
1               5                   10
```

(2) INFORMATION FOR SEQ ID NO: 45:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 45:

Trp Leu Gly Val Ser Arg Gln Leu Arg Thr
1               5                   10

(2) INFORMATION FOR SEQ ID NO: 46:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Arg Leu Asp Cys Trp Arg Gly Gly Gln Val
1               5                   10

(2) INFORMATION FOR SEQ ID NO: 47:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Ser Leu Lys Val Ser Asn Asp Gly Pro Thr
1               5                   10

(2) INFORMATION FOR SEQ ID NO: 48:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Ala Met Leu Gly Thr His Thr Met Glu Val
1               5                   10

(2) INFORMATION FOR SEQ ID NO: 49:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Ala Met Leu Gly Thr His Thr Met Glu Val
1               5                   10

-continued (2) INFORMATION FOR SEQ ID NO: 50:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Met Leu Gly Thr His Thr Met Glu Val Thr
1               5                   10

(2) INFORMATION FOR SEQ ID NO: 51:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Pro Leu Ala His Ser Ser Ser Ala Phe Thr
1               5                   10

(2) INFORMATION FOR SEQ ID NO: 52:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Ala Leu Asp Gly Gly Asn Lys His Phe Leu
1               5                   10

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Phe Leu Arg Asn Gln Pro Leu Thr Phe Ala
1               5                   10

(2) INFORMATION FOR SEQ ID NO: 54:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Gln Leu His Asp Pro Ser Gly Tyr Leu Ala (2) INFORMATION FOR SEQ ID NO: 55:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

Tyr Leu Ala Glu Ala Asp Leu Ser Tyr Thr
1               5                   10

(2) INFORMATION FOR SEQ ID NO: 56:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Thr Leu Ile Ser Arg Ala Pro Val Val Thr
1               5                   10

(2) INFORMATION FOR SEQ ID NO: 57:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Pro Leu Thr Ser Cys Gly Ser Ser Pro Val
1               5                   10

(2) INFORMATION FOR SEQ ID NO: 58:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Thr Leu Ala Glu Met Ser Thr Pro Glu Ala
1               5                   10

(2) INFORMATION FOR SEQ ID NO: 59:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

```
Gly Met Thr Pro Ala Glu Val Ser Ile Val
1               5                   10
```

(2) INFORMATION FOR SEQ ID NO: 60:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

```
Val Leu Ser Gly Thr Thr Ala Ala Gln Val
1               5                   10
```

(2) INFORMATION FOR SEQ ID NO: 61:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

```
Ser Leu Gly Pro Leu Leu Asp Gly Thr Ala
1               5                   10
```

(2) INFORMATION FOR SEQ ID NO: 62:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

```
Leu Leu Asp Gly Thr Ala Thr Leu Arg Leu
1               5                   10
```

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

```
Val Leu Tyr Arg Tyr Gly Ser Phe Ser Val
1               5                   10
```

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

```
Glu Leu Thr Val Ser Cys Gln Gly Gly Leu
1               5                   10
```

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

```
Gly Leu Pro Lys Glu Ala Cys Met Glu Ile
1               5                   10
```

(2) INFORMATION FOR SEQ ID NO: 66:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

```
Val Leu Pro Ser Pro Ala Cys Gln Leu Val
1               5                   10
```

(2) INFORMATION FOR SEQ ID NO: 67:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

```
Ser Leu Ala Asp Thr Asn Ser Leu Ala Val
1               5                   10
```

(2) INFORMATION FOR SEQ ID NO: 68:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

```
Ser Leu Ala Val Val Ser Thr Gln Leu Ile
1               5                   10
```

(2) INFORMATION FOR SEQ ID NO: 69:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

Gln Leu Ile Met Pro Val Pro Gly Ile Leu
1               5                   10

(2) INFORMATION FOR SEQ ID NO: 70:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 70:

Ile Leu Leu Val Leu Met Ala Val Val Leu
1               5                   10

(2) INFORMATION FOR SEQ ID NO: 71:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 71:

Ile Leu Leu Thr Gly Gln Glu Ala Gly Leu
1               5                   10

(2) INFORMATION FOR SEQ ID NO: 72:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 72:

Pro Leu Ile Val Gly Ile Leu Leu Val Leu
1               5                   10

(2) INFORMATION FOR SEQ ID NO: 73:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 73:

Leu Leu Val Leu Met Ala Val Val Leu Ala
1               5                   10

(2) INFORMATION FOR SEQ ID NO: 74:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 74:

Val Leu Met Ala Val Val Leu Ala Ser Leu
1               5                  10

(2) INFORMATION FOR SEQ ID NO: 75:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 75:

Leu Met Ala Val Val Leu Ala Ser Leu Ile
1               5                  10

(2) INFORMATION FOR SEQ ID NO: 76:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 76:

Gln Leu Pro His Ser Ser Ser His Trp Leu
1               5                  10

(2) INFORMATION FOR SEQ ID NO: 77:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 77:

Val Leu Pro Asp Gly Gln Val Ile Trp Val
1               5                  10

(2) INFORMATION FOR SEQ ID NO: 78:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 78:

Leu Ile Ser Arg Ala Pro Val Val Thr
1               5

(2) INFORMATION FOR SEQ ID NO: 79:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 79:

Val Leu Gln Ala Ala Ile Pro Leu Thr
1               5

(2) INFORMATION FOR SEQ ID NO: 80:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 80:

Ser Ile Val Val Leu Ser Gly Thr Thr
1               5

(2) INFORMATION FOR SEQ ID NO: 81:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 81:

Ser Ile Met Ser Thr Glu Ser Ile Thr
1               5

(2) INFORMATION FOR SEQ ID NO: 82:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 82:

Ser Leu Gly Pro Leu Leu Asp Gly Thr
1               5

(2) INFORMATION FOR SEQ ID NO: 83:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 83:

Leu Leu His Leu Ala Val Ile Gly Ala Leu Leu
1               5                   10

(2) INFORMATION FOR SEQ ID NO: 84:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 84:

Cys Leu Leu His Leu Ala Val Ile Gly Ala Leu
1               5                   10

(2) INFORMATION FOR SEQ ID NO: 85:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

His Leu Ala Val Ile Gly Ala Leu Leu Ala Val
1               5                   10

(2) INFORMATION FOR SEQ ID NO: 86:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Asp Leu Val Leu Lys Arg Cys Leu Leu His Leu
1               5                   10

(2) INFORMATION FOR SEQ ID NO: 87:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Val Leu Lys Arg Cys Leu Leu His Leu Ala Val
1               5                   10

(2) INFORMATION FOR SEQ ID NO: 88:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Ser Met Ala Pro Gly Asn Thr Ser Val
1               5

(2) INFORMATION FOR SEQ ID NO: 89:

(i) SEQUENCE CHARACTERISTICS:
        (A) LENGTH: 9 amino acids
        (B) TYPE: amino acid
        (C) STRANDEDNESS: single (D) TOPOLOGY: linear (ii) MOLECULE TYPE: peptide (iii) FEATURE INFORMATION:
        (A) Xaa at position 2 is "Leu" or "Ile"

(xi) SEQUENCE DESCRIPTION: SEQ ID NO: 89:

Ala Xaa Tyr Asp Ala Thr Tyr Glu Thr
1               5

(2) INFORMATION FOR SEQ ID NO: 90:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 90:

TACCTGGAGC CTGGCCAAGT CACTGCC                                    27

(2) INFORMATION FOR SEQ ID NO: 91:

(i) SEQUENCE CHARACTERISTICS:
        (A) LENGTH: 2131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 91:

GGAAGAACAC AATGGATCTG GTGCTAAAAA GATGCCTTCT TCATTTGGCT GTGATAGGTG    60

CTTTGCTGGC TGTGGGGGCT ACAAAAGTAC CCAGAAACCA GGACTGGCTT GGTGTCTCAA   120

GGCAACTCAG AACCAAAGCC TGGAACAGGC AGCTGTATCC AGAGTGGACA GAAGCCCAGA   180

GACTTGACTG CTGGAGAGGT GGTCAAGTGT CCCTCAAGGT CAGTAATGAT GGGCCTACAC   240

TGATTGGTGC AAATGCCTCC TTCTCTATTG CCTTGAACTT CCCTGGAAGC CAAAAGGTAT   300

TGCCAGATGG GCAGGTTATC TGGGTCAACA ATACCATCAT CAATGGGAGC CAGGTGTGGG   360

GAGGACAGCC AGTGTATCCC CAGGAAACTG ACGATGCCTG CATCTTCCCT GATGGTGGAC   420

CTTGCCCATC TGGCTCTTGG TCTCAGAAGA GAAGCTTTGT TTATGTCTGG AAGACCTGGG   480

GCCAATACTG GCAAGTTCTA GGGGGCCCAG TGTCTGGGCT GAGCATTGGG ACAGGCAGGG   540

CAATGCTGGG CACACACACC ATGGAAGTGA CTGTCTACCA TCGCCGGGGA TCCCGGAGCT   600

ATGTGCCTCT TGCTCATTCC AGCTCAGCCT TCACCATTAC TGACCAGGTG CCTTTCTCCG   660

TGAGCGTGTC CCAGTTGCGG GCCTTGGATG GAGGGAACAA GCACTTCCTG AGAAATCAGC   720

CTCTGACCTT TGCCCTCCAG CTCCATGACC CTAGTGGCTA TCTGGCTGAA GCTGACCTCT   780

CCTACACCTG GACTTTGGA GACAGTAGTG GAACCCTGAT CTCTCGGGCA CCTGTGGTCA   840

CTCATACTTA CCTGGAGCCT GGCCCAGTCA CTGCCCAGGT GGTCCTGCAG GCTGCCATTC   900

CTCTCACCTC CTGTGGCTCC TCCCCAGTTC CAGGCACCAC AGATGGGCAC AGGCCAACTG   960

CAGAGGCCCC TAACACCACA GCTGGCCAAG TGCCTACTAC AGAAGTTGTG GGTACTACAC  1020

CTGGTCAGGC GCCAACTGCA GAGCCCTCTG AACCACATC TGTGCAGGTG CCAACCACTG  1080

AAGTCATAAG CACTGCACCT GTGCAGATGC CAACTGCAGA GAGCACAGGT ATGACACCTG  1140

AGAAGGTGCC AGTTTCAGAG GTCATGGGTA CCACACTGGC AGAGATGTCA ACTCCAGAGG  1200

```
CTACAGGTAT GACACCTGCA GAGGTATCAA TTGTGGTGCT TTCTGGAACC ACAGCTGCAC    1260

AGGTAACAAC TACAGAGTGG GTGGAGACCA CAGCTAGAGA GCTACCTATC CCTGAGCCTG    1320

AAGGTCCAGA TGCCAGCTCA ATCATGTCTA CGGAAAGTAT TACAGGTTCC CTGGGCCCCC    1380

TGCTGGATGG TACAGCCACC TTAAGGCTGG TGAAGAGACA AGTCCCCCTG GATTGTGTTC    1440

TGTATCGATA TGGTTCCTTT TCCGTCACCC TGGACATTGT CCAGGGTATT GAAAGTGCCG    1500

AGATCCTGCA GGCTGTGCCG TCCGGTGAGG GGATGCATT  TGAGCTGACT GTGTCCTGCC    1560

AAGGCGGGCT GCCCAAGGAA GCCTGCATGG AGATCTCATC GCCAGGGTGC CAGCCCCCTG    1620

CCCAGCGGCT GTGCCAGCCT GTGCTACCCA GCCCAGCCTG CCAGCTGGTT CTGCACCAGA    1680

TACTGAAGGG TGGCTCGGGG ACATACTGCC TCAATGTGTC TCTGGCTGAT ACCAACAGCC    1740

TGGCAGTGGT CAGCACCCAG CTTATCATGC CTGTGCCTGG GATTCTTCTC ACAGGTCAAG    1800

AAGCAGGCCT TGGGCAGGTT CGGCTGATCG TGGGCATCTT GCTGGTGTTG ATGGCTGTGG    1860

TCCTTGCATC TCTGATATAT AGGCGCAGAC TTATGAAGCA AGACTTCTCC GTACCCCAGT    1920

TGCCACATAG CAGCAGTCAC TGGCTGCGTC TACCCCGCAT CTTCTGCTCT TGTCCCATTG    1980

GTGAGAATAG CCCCCTCCTC AGTGGGCAGC AGGTCTGAGT ACTCTCATAT GATGCTGTGA    2040

TTTTCCTGGA GTTGACAGAA ACACCTATAT TTCCCCCAGT CTTCCCTGGG AGACTACTAT    2100

TAACTGAAAT AAATACTCAG AGCCTGAAAA A                                   2131

(2) INFORMATION FOR SEQ ID NO: 92:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 92:

TATATGGATG GAACAATGTC CGAGGTA                                         27

(2) INFORMATION FOR SEQ ID NO: 93:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

Lys Cys Asp Ile Cys Thr Asp Glu Tyr
1               5

(2) INFORMATION FOR SEQ ID NO: 94:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

Tyr Met Asn Gly Thr Met Ser Gln Val
1               5
```

(2) INFORMATION FOR SEQ ID NO: 95:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

```
Met Leu Leu Ala Val Leu Tyr Cys Leu
1               5
```

(2) INFORMATION FOR SEQ ID NO: 96:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

```
Glu Val Asp Pro Ile Gly His Leu Tyr
1               5
```

(2) INFORMATION FOR SEQ ID NO: 97:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

```
Ala Ala Gly Ile Gly Ile Leu Thr Val
1               5
```

(2) INFORMATION FOR SEQ ID NO: 98:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

```
Ala Leu Leu Ala Val Gly Ala Thr Lys
1               5
```

(2) INFORMATION FOR SEQ ID NO: 99:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 99:

```
Glu Ala Asp Pro Thr Gly His Ser Tyr
```

-continued 1           5

(2) INFORMATION FOR SEQ ID NO: 100:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

Gln Val Pro Leu Arg Pro Met Thr Tyr Lys
1               5                   10

(2) INFORMATION FOR SEQ ID NO: 101:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 101:

Asp Ala Glu Lys Cys Asp Ile Cys Thr Asp Glu Tyr
1               5                   10

(2) INFORMATION FOR SEQ ID NO: 102:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 102:

Glu Lys Cys Asp Ile Cys Thr Asp Glu Tyr
1               5                   10

(2) INFORMATION FOR SEQ ID NO: 103:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

Tyr Leu Glu Pro Gly Val Thr Val
1               5

(2) INFORMATION FOR SEQ ID NO: 104:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

```
Ala Phe Leu Pro Trp His Arg Leu Phe
1               5
```

(2) INFORMATION FOR SEQ ID NO: 105:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

```
Ala Phe Leu Pro Trp His Arg Leu Phe Leu
1               5                   10
```

(2) INFORMATION FOR SEQ ID NO: 106:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

```
Ser Glu Ile Trp Arg Asp Ile Asp Phe
1               5
```

(2) INFORMATION FOR SEQ ID NO: 107:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

```
Lys Thr Trp Gly Gln Tyr Trp Gln Val
1               5
```

(2) INFORMATION FOR SEQ ID NO: 108:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

```
Ile Thr Asp Gln Val Pro Phe Ser Val
1               5
```

(2) INFORMATION FOR SEQ ID NO: 109:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

```
Ala Ala Gly Ile Gly Ile Leu Thr Val
1               5
```

(2) INFORMATION FOR SEQ ID NO: 110:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

```
Ile Leu Thr Val Ile Leu Gly Val Leu
1               5
```

(2) INFORMATION FOR SEQ ID NO: 111:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

```
Ser Ala Tyr Gly Glu Pro Arg Lys Leu
1               5
```

(2) INFORMATION FOR SEQ ID NO: 112:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

```
Phe Leu Trp Gly Pro Arg Ala Leu Val
1               5
```

(2) INFORMATION FOR SEQ ID NO: 113:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

```
Ala Ala Arg Ala Val Phe Leu Ala Leu
1               5
```

(2) INFORMATION FOR SEQ ID NO: 114:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

Tyr Arg Pro Arg Pro Arg Arg Tyr
1               5

(2) INFORMATION FOR SEQ ID NO: 115:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Lys Ile Phe Gly Ser Leu Ala Phe Leu
1               5

(2) INFORMATION FOR SEQ ID NO: 116:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

Val Met Ala Gly Val Gly Ser Pro Tyr Val
1               5                   10

(2) INFORMATION FOR SEQ ID NO: 117:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

Ile Ile Ser Ala Val Val Gly Ile Leu
1               5

(2) INFORMATION FOR SEQ ID NO: 118:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

Tyr Leu Ser Gly Ala Asn Leu Asn Leu
1               5

(2) INFORMATION FOR SEQ ID NO: 119:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 119:

Glu Ala Tyr Gly Leu Asp Phe Tyr Ile Leu
1               5                   10

(2) INFORMATION FOR SEQ ID NO: 120:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 120:

Gln Asp Leu Thr Met Lys Tyr Gln Ile Phe
1               5                   10

(2) INFORMATION FOR SEQ ID NO: 121:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 121:

Glu Glu Lys Leu Ile Val Val Leu Phe
1               5

(2) INFORMATION FOR SEQ ID NO: 122:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 122:

Ser Tyr Leu Asp Ser Gly Ile His Phe
1               5

(2) INFORMATION FOR SEQ ID NO: 123:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) FEATURE INFORMATION:
            (A) Xaa at position 2 is "Leu" or "Ile"

(xi) SEQUENCE DESCRIPTION: SEQ ID NO: 123:

Tyr Xaa Glu Pro Gly Pro Val Thr Ala
1               5

(2) INFORMATION FOR SEQ ID NO: 124:

(i) SEQUENCE CHARACTERISTICS:
            (A) LENGTH: 9 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 124:

Ser Met Ala Pro Gly Asn Thr Ser Val
1               5

(2) INFORMATION FOR SEQ ID NO: 125:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) FEATURE INFORMATION:
            (A) Xaa at position 2 is "Leu" or "Ile"

(xi) SEQUENCE DESCRIPTION: SEQ ID NO: 125:

Ala Xaa Tyr Asp Ala Thr Tyr Glu Thr
1               5

(2) INFORMATION FOR SEQ ID NO: 126:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 126:

Phe Leu Pro Ser Asp Tyr Phe Pro Ser Val
1               5                   10

(2) INFORMATION FOR SEQ ID NO: 127:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 127:

Ala Leu Trp Gly Phe Phe Pro Val Leu
1               5

(2) INFORMATION FOR SEQ ID NO: 128:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 128:

Ala Pro Arg Thr Val Ala Leu Thr Ala
1               5

(2) INFORMATION FOR SEQ ID NO: 129:
```

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 129:

Gln Leu Arg Ala Leu Asp Gly Gly Asn Lys
1               5                   10

(2) INFORMATION FOR SEQ ID NO: 130:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 130:

Ala Leu Gln Leu His Asp Pro Ser Gly Tyr
1               5                   10

(2) INFORMATION FOR SEQ ID NO: 131:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 131:

Ala Val Pro Ser Gly Glu Gly Asp Ala Phe
1               5                   10

(2) INFORMATION FOR SEQ ID NO: 132:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 132:

Thr Val Ser Cys Gln Gly Gly Leu Pro Lys
1               5                   10

(2) INFORMATION FOR SEQ ID NO: 133:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 133:

Gln Ile Leu Lys Gly Gly Ser Gly Thr Tyr
1               5                   10
```

(2) INFORMATION FOR SEQ ID NO: 134:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 134:

Ser Leu Ile Tyr Arg Arg Arg Leu Met Lys
1               5                   10

(2) INFORMATION FOR SEQ ID NO: 135:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 135:

Pro Leu Ala His Ser Ser Ser Ala Phe
1               5

(2) INFORMATION FOR SEQ ID NO: 136:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

Ala Leu Asp Gly Gly Asn Lys His Phe
1               5

(2) INFORMATION FOR SEQ ID NO: 137:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

Phe Leu Arg Asn Pro Pro Leu Thr Phe
1               5

(2) INFORMATION FOR SEQ ID NO: 138:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

Tyr Leu Ala Glu Ala Asp Leu Ser Tyr
1               5

-continued (2) INFORMATION FOR SEQ ID NO: 139:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

```
Gln Val Pro Leu Asp Cys Val Leu Tyr
1               5
```

(2) INFORMATION FOR SEQ ID NO: 140:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

```
Pro Leu Asp Cys Val Leu Tyr Arg Tyr
1               5
```

(2) INFORMATION FOR SEQ ID NO: 141:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

```
Cys Val Leu Tyr Arg Tyr Gly Ser Phe
1               5
```

(2) INFORMATION FOR SEQ ID NO: 142:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 142:

```
Gln Leu Val Leu His Gln Ile Leu Lys
1               5
```

(2) INFORMATION FOR SEQ ID NO: 143:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 143:

```
Ile Leu Lys Gly Gly Ser Gly Thr Tyr
1               5
```

-continued (2) INFORMATION FOR SEQ ID NO: 144:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 144:

Ala Val Val Leu Ala Ser Leu Ile Tyr
1               5

(2) INFORMATION FOR SEQ ID NO: 145:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 145:

Leu Ile Tyr Arg Arg Arg Leu Met Lys
1               5

(2) INFORMATION FOR SEQ ID NO: 146:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 146:

Gly Val Ser Arg Gln Leu Arg Thr Lys
1               5

(2) INFORMATION FOR SEQ ID NO: 147:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

Thr Leu Ile Gly Ala Asn Ala Ser Phe
1               5

(2) INFORMATION FOR SEQ ID NO: 148:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

Ala Leu Asn Phe Pro Gly Ser Gln Lys

```
1               5
```

(2) INFORMATION FOR SEQ ID NO: 149:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

```
Gln Val Trp Gly Gly Gln Pro Val Tyr
1               5
```

(2) INFORMATION FOR SEQ ID NO: 150:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 150:

```
Tyr Val Trp Lys Thr Trp Gly Gln Tyr
1               5
```

(2) INFORMATION FOR SEQ ID NO: 151:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 151:

```
Ala Ser Phe Ser Ile Ala Leu Asn Phe
1               5
```

(2) INFORMATION FOR SEQ ID NO: 152:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 152:

```
Ala Leu Val Val Thr His Thr Tyr
1               5
```

(2) INFORMATION FOR SEQ ID NO: 153:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 153:

```
Leu Asn Phe Pro Gly Ser Gln Lys
1               5
```

(2) INFORMATION FOR SEQ ID NO: 154:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 154:

```
Thr Ile Thr Asp Gln Val Pro Phe
1               5
```

(2) INFORMATION FOR SEQ ID NO: 155:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 155:

```
Gln Leu His Asp Pro Ser Gly Tyr
1               5
```

(2) INFORMATION FOR SEQ ID NO: 156:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 156:

```
Asp Leu Ser Tyr Thr Trp Asp Phe
1               5
```

(2) INFORMATION FOR SEQ ID NO: 157:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 157:

```
Val Leu Tyr Arg Tyr Gly Ser Phe
1               5
```

(2) INFORMATION FOR SEQ ID NO: 158:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 158:

```
Leu Val Leu His Gln Ile Leu Lys
1               5
```

(2) INFORMATION FOR SEQ ID NO: 159:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 159:

```
Val Val Leu Ala Ser Leu Ile Tyr
1               5
```

(2) INFORMATION FOR SEQ ID NO: 160:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 160:

```
Trp Leu Arg Leu Pro Arg Ile Phe
1               5
```

(2) INFORMATION FOR SEQ ID NO: 161:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 161:

```
Ala Lys His Thr Ile Ser Ser Asp Tyr
1               5
```

(2) INFORMATION FOR SEQ ID NO: 162:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 162:

```
Ala Pro Glu Lys Asp Lys Phe Phe Ala Tyr
1               5                   10
```

(2) INFORMATION FOR SEQ ID NO: 163:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 163:

Ala Pro Val Val Thr His Thr Tyr
1               5

(2) INFORMATION FOR SEQ ID NO: 164:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 164:

Asp Leu Phe Val Trp Ile His Tyr Tyr
1               5

(2) INFORMATION FOR SEQ ID NO: 165:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

Asp Leu Phe Val Trp Met His Ile Tyr
1               5

(2) INFORMATION FOR SEQ ID NO: 166:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

Asp Arg Glu Ser Trp Pro Ser Val Phe Tyr
1               5                   10

(2) INFORMATION FOR SEQ ID NO: 167:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

Asp Ser Asp Pro Asp Ser Phe Gln Asp Tyr
1               5                   10

(2) INFORMATION FOR SEQ ID NO: 168:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO: 168:

Asp Ser Phe Gln Asp Tyr Ile Lys Ser Tyr
1               5                  10

(2) INFORMATION FOR SEQ ID NO: 169:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 169:

Asp Tyr Val Ile Pro Ile Gly Thr Tyr
1               5

(2) INFORMATION FOR SEQ ID NO: 170:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 170:

Glu Phe Cys Ser Leu Thr Gln Tyr
1               5

(2) INFORMATION FOR SEQ ID NO: 171:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 171:

Glu Lys Glu Asp Tyr His Ser Leu Tyr
1               5

(2) INFORMATION FOR SEQ ID NO: 172:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 172:

Phe Ile Ser Ser Lys Asp Leu Gly Tyr
1               5

(2) INFORMATION FOR SEQ ID NO: 173:

(i) SEQUENCE CHARACTERISTICS:
            (A) LENGTH: 8 amino acids
            (B) TYPE: amino acid
            (C) STRANDEDNESS: single
            (D) TOPOLOGY: linear
```

```
    (ii) MOLECULE TYPE: peptide (xi) SEQUENCE DESCRIPTION: SEQ ID NO: 173:

Phe Gln Asp Tyr Ile Lys Ser Tyr
1               5

(2) INFORMATION FOR SEQ ID NO: 174:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 174:

Gly Asp Glu Asn Phe Thr Ile Pro Tyr
1               5

(2) INFORMATION FOR SEQ ID NO: 175:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 175:

Ile Ser Ser Lys Asp Leu Gly Tyr Asp Tyr
1               5                   10

(2) INFORMATION FOR SEQ ID NO: 176:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 176:

Ile Val Cys Ser Arg Leu Glu Glu Tyr
1               5

(2) INFORMATION FOR SEQ ID NO: 177:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 177:

Ile Tyr Asp Leu Phe Val Trp Met His Tyr
1               5                   10

(2) INFORMATION FOR SEQ ID NO: 178:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

```
         (ii) MOLECULE TYPE: peptide (xi) SEQUENCE DESCRIPTION: SEQ ID NO: 178:

Lys Cys Asp Ile Cys Thr Asp Glu Tyr
1               5

(2) INFORMATION FOR SEQ ID NO: 179:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 179:

Lys Asp Leu Gly Tyr Asp Tyr Ser Tyr
1               5

(2) INFORMATION FOR SEQ ID NO: 180:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 180:

Lys Glu Asp Tyr His Ser Leu Tyr
1               5

(2) INFORMATION FOR SEQ ID NO: 181:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 181:

Pro Glu Lys Asp Lys Phe Phe Ala Tyr
1               5

(2) INFORMATION FOR SEQ ID NO: 182:

(i) SEQUENCE CHARACTERISTICS:
              (A) LENGTH: 9 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 182:

Pro Ile Gly His Asn Arg Glu Ser Tyr
1               5

(2) INFORMATION FOR SEQ ID NO: 183:

(i) SEQUENCE CHARACTERISTICS:
              (A) LENGTH: 9 amino acids
              (B) TYPE: amino acid
              (C) STRANDEDNESS: single
```

```
        (D) TOPOLOGY: linear (ii) MOLECULE TYPE: peptide (xi) SEQUENCE DESCRIPTION: SEQ ID NO: 183:

Pro Leu Leu Met Glu Lys Glu Asp Tyr
1               5

(2) INFORMATION FOR SEQ ID NO: 184:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 184:

Pro Met Phe Asn Asp Ile Asn Ile Tyr
1               5

(2) INFORMATION FOR SEQ ID NO: 185:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 185:

Arg Glu Ser Trp Pro Ser Val Phe Tyr
1               5

(2) INFORMATION FOR SEQ ID NO: 186:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 186:

Arg His Arg Pro Leu Gln Glu Val Tyr
1               5

(2) INFORMATION FOR SEQ ID NO: 187:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 187:

Ser Asp Pro Asp Ser Phe Gln Asp Tyr
1               5

(2) INFORMATION FOR SEQ ID NO: 188:

(i) SEQUENCE CHARACTERISTICS:
        (A) LENGTH: 9 amino acids
        (B) TYPE: amino acid
```

```
            (C) STRANDEDNESS: single
            (D) TOPOLOGY: linear (ii) MOLECULE TYPE: peptide (xi) SEQUENCE DESCRIPTION: SEQ ID NO: 188:

Ser Phe Gln Asp Tyr Ile Lys Ser Tyr
1               5

(2) INFORMATION FOR SEQ ID NO: 189:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 189:

Ser Lys Asp Leu Asp Tyr Gly Tyr
1               5

(2) INFORMATION FOR SEQ ID NO: 190:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 190:

Ser Lys Asp Leu Gly Tyr Asp Tyr Ser Tyr
1               5                   10

(2) INFORMATION FOR SEQ ID NO: 191:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 191:

Ser Met Asp Ala Leu Leu Gly Gly Tyr
1               5

(2) INFORMATION FOR SEQ ID NO: 192:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 192:

Ser Met His Asn Ala Leu His Ile Tyr
1               5

(2) INFORMATION FOR SEQ ID NO: 193:

(i) SEQUENCE CHARACTERISTICS:
            (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 193:

Ser Ser Lys Asp Leu Gly Tyr Asp Tyr
1               5

(2) INFORMATION FOR SEQ ID NO: 194:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 194:

Ser Ser Met His Asn Ala Leu His Ile Tyr
1               5                   10

(2) INFORMATION FOR SEQ ID NO: 195:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 195:

Thr Gly Asp Glu Asn Phe Thr Ile Pro Tyr
1               5                   10

(2) INFORMATION FOR SEQ ID NO: 196:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 196:

Tyr Met Val Pro Phe Ile Pro Leu Tyr
1               5

(2) INFORMATION FOR SEQ ID NO: 197:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 197:

Ala Asn Ala Pro Ile Gly His Asn Arg Glu Ser Tyr
1               5                   10

(2) INFORMATION FOR SEQ ID NO: 198:

(i) SEQUENCE CHARACTERISTICS:
```

(A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 198:

Ala Pro Ile Gly His Asn Arg Glu Ser Tyr
1               5                   10

(2) INFORMATION FOR SEQ ID NO: 199:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 199:

Asp Ala Glu Lys Cys Asp Ile Cys Thr Asp Glu Tyr
1               5                   10

(2) INFORMATION FOR SEQ ID NO: 200:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 200:

Asp Leu Phe Val Trp Met His Tyr Tyr
1               5

(2) INFORMATION FOR SEQ ID NO: 201:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 201:

Asp Pro Asp Ser Phe Gln Asp Tyr Ile Lys Ser Tyr
1               5                   10

(2) INFORMATION FOR SEQ ID NO: 202:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 202:

Asp Val Glu Phe Cys Leu Ser Leu Thr Gln Tyr
1               5                   10

(2) INFORMATION FOR SEQ ID NO: 203:

```
     (i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 203:

Glu Lys Cys Asp Ile Cys Thr Asp Glu Tyr
1               5                   10

(2) INFORMATION FOR SEQ ID NO: 204:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 204:

Glu Ser Tyr Met Val Pro Phe Ile Pro Leu Tyr
1               5                   10

(2) INFORMATION FOR SEQ ID NO: 205:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 205:

Phe Phe Ile Ser Ser Lys Asp Leu Gly Tyr
1               5                   10

(2) INFORMATION FOR SEQ ID NO: 206:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 206:

Phe Ile Ser Ser Lys Asp Leu Gly Tyr Asp Tyr
1               5                   10

(2) INFORMATION FOR SEQ ID NO: 207:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 207:

Gly Asp Glu Asp Phe Thr Ile Pro Tyr
1               5

(2) INFORMATION FOR SEQ ID NO: 208:
```

```
    (i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 208:

Gly Ser Thr Pro Met Phe Asn Asp Ile Asn Thr Tyr
1               5                   10

(2) INFORMATION FOR SEQ ID NO: 209:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 209:

Ile Ser Ser Asp Tyr Val Ile Pro Ile Gly Thr Tyr
1               5                   10

(2) INFORMATION FOR SEQ ID NO: 210:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 210:

Ile Ser Ser Lys Asp Leu Gly Tyr Asp Tyr Ser Tyr
1               5                   10

(2) INFORMATION FOR SEQ ID NO: 211:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 211:

Ile Tyr Asp Leu Phe Val Trp Met His Tyr Tyr
1               5                   10

(2) INFORMATION FOR SEQ ID NO: 212:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 212:

Ile Tyr Asp Leu Phe Val Trp Ile His Tyr Tyr
1               5                   10
```

-continued (2) INFORMATION FOR SEQ ID NO: 213:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 213:

```
Ile Tyr Asp Leu Phe Val Trp Met His Tyr Tyr
1               5                   10
```

(2) INFORMATION FOR SEQ ID NO: 214:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 214:

```
Leu Ala Lys His Thr Ile Ser Ser Asp Tyr
1               5                   10
```

(2) INFORMATION FOR SEQ ID NO: 215:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 215:

```
Leu Met Glu Lys Glu Asp Tyr His Ser Leu Tyr
1               5                   10
```

(2) INFORMATION FOR SEQ ID NO: 216:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 216:

```
Leu Gln Asp Ser Asp Pro Asp Ser Phe Gln Asp Tyr
1               5                   10
```

(2) INFORMATION FOR SEQ ID NO: 217:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 217:

```
Leu Ser Ala Pro Glu Lys Asp Lys Phe Phe Ala Tyr
1               5                   10
```

(2) INFORMATION FOR SEQ ID NO: 218:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 218:

```
Leu Thr Gly Asp Glu Asp Phe Thr Ile Pro Tyr
1               5                   10
```

(2) INFORMATION FOR SEQ ID NO: 219:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 219:

```
Leu Thr Gly Asp Glu Asn Phe Thr Ile Pro Tyr
1               5                   10
```

(2) INFORMATION FOR SEQ ID NO: 220:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 220:

```
Leu Thr Leu Ala Lys His Thr Ile Ser Ser Asp Tyr
1               5                   10
```

(2) INFORMATION FOR SEQ ID NO: 221:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 221:

```
Met Glu Lys Glu Asp Tyr His Ser Leu Tyr
1               5                   10
```

(2) INFORMATION FOR SEQ ID NO: 222:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 222:

```
Pro Asp Ser Phe Gln Asp Tyr Ile Lys Ser Tyr
1               5                   10
```

(2) INFORMATION FOR SEQ ID NO: 223:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 223:

Gln Asp Ser Asp Pro Asp Ser Phe Gln Asp Tyr
1               5                   10

(2) INFORMATION FOR SEQ ID NO: 224:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 224:

Gln Ile Val Cys Ser Arg Leu Glu Glu Tyr
1               5                   10

(2) INFORMATION FOR SEQ ID NO: 225:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 225:

Gln Pro Leu Leu Met Glu Lys Glu Asp Tyr
1               5                   10

(2) INFORMATION FOR SEQ ID NO: 226:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 226:

Gln Arg His Arg Pro Leu Gln Glu Val Tyr
1               5                   10

(2) INFORMATION FOR SEQ ID NO: 227:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 227:

Gln Ser Ser Met His Asn Ala Leu His Ile Tyr (2) INFORMATION FOR SEQ ID NO: 228:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 228:

Arg Glu Ser Tyr Met Val Pro Phe Thr Pro Leu Tyr
1           5                 10

(2) INFORMATION FOR SEQ ID NO: 229:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 229:

Arg Arg His Arg Pro Leu Gln Glu Val Tyr
1           5                 10

(2) INFORMATION FOR SEQ ID NO: 230:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 230:

Ser Asp Tyr Val Ile Pro Ile Gly Thr Tyr
1           5                 10

(2) INFORMATION FOR SEQ ID NO: 231:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 231:

Ser Gln Ser Ser Met His Asn Ala Leu His Ile Tyr
1           5                 10

(2) INFORMATION FOR SEQ ID NO: 232:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 232:

```
Ser Ser Asp Tyr Val Ile Pro Ile Gly Thr Tyr
1               5                   10
```

(2) INFORMATION FOR SEQ ID NO: 233:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 233:

```
Ser Ser Lys Asp Leu Gly Tyr Asp Tyr Ser Tyr
1               5                   10
```

(2) INFORMATION FOR SEQ ID NO: 234:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 234:

```
Ser Thr Pro Met Phe Asn Asp Ile Asn Ile Tyr
1               5                   10
```

(2) INFORMATION FOR SEQ ID NO: 235:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 235:

```
Ser Tyr Met Val Pro Phe Ile Pro Leu Tyr
1               5                   10
```

(2) INFORMATION FOR SEQ ID NO: 236:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 236:

```
Thr Gly Asp Glu Asp Phe Thr Ile Pro Tyr
1               5                   10
```

(2) INFORMATION FOR SEQ ID NO: 237:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 237:

```
Thr Leu Ala Lys His Thr Ile Ser Ser Asp Tyr
1               5                   10
```

(2) INFORMATION FOR SEQ ID NO: 238:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 238:

```
Thr Pro Met Phe Asn Asp Ile Asn Ile Tyr
1               5                   10
```

(2) INFORMATION FOR SEQ ID NO: 239:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 239:

```
Val Asp Asp Arg Glu Ser Trp Pro Ser Val Phe Tyr
1               5                   10
```

(2) INFORMATION FOR SEQ ID NO: 240:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 240:

```
Val Glu Phe Cys Leu Ser Leu Thr Gln Tyr
1               5                   10
```

(2) INFORMATION FOR SEQ ID NO: 241:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 241:

```
Val Ser Met Asp Ala Leu Leu Gly Gly Tyr
1               5                   10
```

(2) INFORMATION FOR SEQ ID NO: 242:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 242:

Tyr Val Ser Met Asp Ala Leu Leu Gly Gly Tyr
1               5                   10

(2) INFORMATION FOR SEQ ID NO: 243:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 243:

Ala Met Glu Arg Pro Arg Asp Leu Tyr
1               5

(2) INFORMATION FOR SEQ ID NO: 244:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 244:

Glu Val Ser Thr Pro Gln Ile Leu Thr Tyr
1               5                   10

(2) INFORMATION FOR SEQ ID NO: 245:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 245:

Ile Thr Thr Ala Cys Ile Arg Ala Ile Tyr
1               5                   10

(2) INFORMATION FOR SEQ ID NO: 246:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 246:

Ile Trp Ala Met Thr Ile Ala Ile Tyr
1               5

(2) INFORMATION FOR SEQ ID NO: 247:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO: 247:

Arg Ser Thr Thr Ala Ile Ser Leu Tyr
1               5

(2) INFORMATION FOR SEQ ID NO: 248:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 248:

Thr Thr Ala Cys Ile Arg Ala Ile Tyr
1               5

(2) INFORMATION FOR SEQ ID NO: 249:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 249:

Val Ser Thr Pro Gln Ile Leu Thr Tyr
1               5

(2) INFORMATION FOR SEQ ID NO: 250:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 250:

Trp Arg Ser Thr Thr Ala Ile Ser Leu Tyr
1               5                   10

(2) INFORMATION FOR SEQ ID NO: 251:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 251:

Tyr Asp Leu Phe Val Trp Ile His Tyr
1               5

(2) INFORMATION FOR SEQ ID NO: 252:

(i) SEQUENCE CHARACTERISTICS:
         (A) LENGTH: 10 amino acids
         (B) TYPE: amino acid
         (C) STRANDEDNESS: single
         (D) TOPOLOGY: linear
```

(ii) MOLECULE TYPE: peptide (xi) SEQUENCE DESCRIPTION: SEQ ID NO: 252:

Tyr Asp Leu Phe Val Trp Ile His Tyr Tyr
1               5                   10

(2) INFORMATION FOR SEQ ID NO: 253:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 253:

Tyr Asp Leu Phe Val Trp Met His Tyr
1               5

(2) INFORMATION FOR SEQ ID NO: 254:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 254:

Tyr Asp Leu Phe Val Trp Met His Tyr Tyr
1               5                   10

(2) INFORMATION FOR SEQ ID NO: 255:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 255:

Ala Asn Asp Pro Ile Phe Leu Leu His
1               5

(2) INFORMATION FOR SEQ ID NO: 256:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 256:

Ala Asn Asp Pro Ile Phe Leu Leu His His
1               5                   10

(2) INFORMATION FOR SEQ ID NO: 257:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 257:

Cys Cys Pro Pro Trp Ser Gly Asp Arg
1               5

(2) INFORMATION FOR SEQ ID NO: 258:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 258:

Cys Thr Asp Glu Tyr Met Gly Gly Gln
1               5

(2) INFORMATION FOR SEQ ID NO: 259:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 259:

Cys Thr Asp Glu Tyr Met Gly Gly Gln His
1               5                   10

(2) INFORMATION FOR SEQ ID NO: 260:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 260:

Cys Thr Glu Arg Arg Leu Leu Val Arg
1               5

(2) INFORMATION FOR SEQ ID NO: 261:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 261:

Cys Thr Glu Arg Arg Leu Leu Val Arg Arg
1               5                   10

(2) INFORMATION FOR SEQ ID NO: 262:

(i) SEQUENCE CHARACTERISTICS:
            (A) LENGTH: 10 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO: 262:

Cys Val Ser Ser Lys Asn Leu Met Glu Lys
1               5                   10

(2) INFORMATION FOR SEQ ID NO: 263:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 263:

Asp Gly Thr Pro Glu Gly Pro Leu Arg Arg
1               5                   10

(2) INFORMATION FOR SEQ ID NO: 264:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 264:

Asp Ile Asp Phe Ala His Glu Ala Pro Ala
1               5                   10

(2) INFORMATION FOR SEQ ID NO: 265:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 265:

Asp Pro Asp Ser Phe Gln Asp Tyr Ile Lys
1               5                   10

(2) INFORMATION FOR SEQ ID NO: 266:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 266:

Asp Ser Asp Pro Asp Ser Phe Gln Asp
1               5

(2) INFORMATION FOR SEQ ID NO: 267:

(i) SEQUENCE CHARACTERISTICS:
            (A) LENGTH: 10 amino acids
            (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 267:

Asp Val Glu Phe Cys Leu Ser Leu Thr Gln
1               5                   10

(2) INFORMATION FOR SEQ ID NO: 268:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 268:

Glu Cys Cys Pro Pro Trp Ser Gly Asp Arg
1               5                   10

(2) INFORMATION FOR SEQ ID NO: 269:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 269:

Phe Asn Asp Ile Asn Ile Tyr Asp Leu Phe
1               5                   10

(2) INFORMATION FOR SEQ ID NO: 270:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 270:

Phe Thr Ile Pro Tyr Trp Asp Trp Arg
1               5

(2) INFORMATION FOR SEQ ID NO: 271:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 271:

Gly Ser Glu Ile Trp Arg Asp Ile Asp Phe
1               5                   10

(2) INFORMATION FOR SEQ ID NO: 272:

(i) SEQUENCE CHARACTERISTICS:
            (A) LENGTH: 9 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 272:

Gly Thr Pro Glu Gly Pro Leu Arg Arg
1               5

(2) INFORMATION FOR SEQ ID NO: 273:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 273:

Gly Tyr Glu Ile Trp Arg Asp Ile Asp Phe
1               5                   10

(2) INFORMATION FOR SEQ ID NO: 274:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 274:

Ile Phe Asp Leu Ser Ala Pro Glu Lys
1               5

(2) INFORMATION FOR SEQ ID NO: 275:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 275:

Leu Pro Glu Glu Lys Gln Pro Leu Leu Met
1               5                   10

(2) INFORMATION FOR SEQ ID NO: 276:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 276:

Leu Ser Ala Pro Glu Lys Asp Lys Phe
1               5

(2) INFORMATION FOR SEQ ID NO: 277:

(i) SEQUENCE CHARACTERISTICS:
```

```
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 277:

Leu Ser Ala Pro Glu Lys Asp Lys Phe Phe
1               5                   10

(2) INFORMATION FOR SEQ ID NO: 278:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 278:

Asn Gly Asp Phe Phe Ile Ser Ser Lys
1               5

(2) INFORMATION FOR SEQ ID NO: 279:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 279:

Asn Gly Thr Pro Glu Gly Pro Leu Arg Arg
1               5                   10

(2) INFORMATION FOR SEQ ID NO: 280:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 280:

Gln Thr Ser Ala Gly His Phe Pro Arg
1               5

(2) INFORMATION FOR SEQ ID NO: 281:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 281:

Gln Tyr Glu Ser Gly Ser Met Asp Lys
1               5

(2) INFORMATION FOR SEQ ID NO: 282:
```

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 282:

Ser Ala Asp Val Glu Phe Cys Leu Ser Leu
1               5                   10

(2) INFORMATION FOR SEQ ID NO: 283:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 283:

Ser Met Asp Lys Ala Ala Asp Phe Ser Phe
1               5                   10

(2) INFORMATION FOR SEQ ID NO: 284:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 284:

Ser Met Asp Lys Ala Ala Asn Phe Ser Phe
1               5                   10

(2) INFORMATION FOR SEQ ID NO: 285:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 285:

Ser Ser Asp Tyr Val Ile Pro Ile Gly
1               5

(2) INFORMATION FOR SEQ ID NO: 286:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 286:

Ser Ser Asp Tyr Val Ile Pro Ile Gly Thr
1               5                   10

(2) INFORMATION FOR SEQ ID NO: 287:

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 287:

Thr Leu Glu Gly Phe Ala Ser Pro Leu Thr
1               5                   10

(2) INFORMATION FOR SEQ ID NO: 288:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 288:

Tyr Leu Glu Gln Ala Ser Arg Ile Trp Ser
1               5                   10

(2) INFORMATION FOR SEQ ID NO: 289:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 289:

Tyr Met Val Pro Phe Ile Pro Leu Tyr Arg
1               5                   10

(2) INFORMATION FOR SEQ ID NO: 290:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 290:

Tyr Pro Glu Ala Asn Ala Pro Ile Gly His
1               5                   10

(2) INFORMATION FOR SEQ ID NO: 291:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 291:

Tyr Trp Asp Trp Arg Asp Ala Glu Lys
1               5
```

-continued (2) INFORMATION FOR SEQ ID NO: 292:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 292:

```
Met Leu Leu Ala Val Leu Tyr Cys Leu Leu Trp Ser Phe Gln Thr Ser
 1               5                  10                  15

Ala Gly His Phe Pro Arg Ala Cys Val Ser Ser Lys Asn Leu Met Glu
             20                  25                  30

Lys Glu Cys Cys Pro Pro Trp Ser Gly Asp Arg Ser Pro Cys Gly Gln
         35                  40                  45

Leu Ser Gly Arg Gly Ser Cys Gln Asn Ile Leu Leu Ser Asn Ala Pro
     50                  55                  60

Leu Gly Pro Gln Phe Pro Phe Thr Gly Val Asp Asp Arg Glu Ser Trp
 65                  70                  75                  80

Pro Ser Val Phe Tyr Asn Arg Thr Cys Gln Cys Ser Gly Asn Phe Met
                 85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
        195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
    290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Asp Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
```

-continued

```
                    355                 360                 365
    Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
    385                 390                 395                 400

Leu Gln Arg His Arg Pro Leu Gln Glu Val Tyr Pro Glu Ala Asn Ala
                    405                 410                 415

Pro Ile Gly His Asn Arg Glu Ser Tyr Met Val Pro Phe Ile Pro Leu
                    420                 425                 430

Tyr Arg Asn Gly Asp Phe Phe Ile Ser Ser Lys Asp Leu Gly Tyr Asp
                    435                 440                 445

Tyr Ser Tyr Leu Gln Asp Ser Asp Pro Asp Ser Phe Gln Asp Tyr Ile
        450                 455                 460

Lys Ser Tyr Leu Glu Gln Ala Ser Arg Ile Trp Ser Trp Leu Leu Gly
    465                 470                 475                 480

Ala Ala Met Val Gly Ala Val Leu Thr Ala Leu Leu Ala Gly Leu Val
                    485                 490                 495

Ser Leu Leu Cys Arg His Lys Arg Lys Gln Leu Pro Glu Glu Lys Gln
                    500                 505                 510

Pro Leu Leu Met Glu Lys Glu Asp Tyr His Ser Leu Tyr Gln Ser His
            515                 520                 525

Leu (2) INFORMATION FOR SEQ ID NO: 293:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 293:

Glu Glu Lys Leu Ser Val Val Leu Phe
1               5

(2) INFORMATION FOR SEQ ID NO: 294:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 294:

Ser Tyr Leu Asp Ser Gly Ile His Ser
1               5
```

PEPTIDES RECOGNIZED BY MELANOMA-SPECIFIC A1-, A2- AND A3-RESTRICTED CYTOXIC LYMPHOCYTES, AND USES THEREFOR

This application claims the benefit under 35 USC §119 of prior provisional application 60/013,972, filed Mar. 19, 1996 (Dkt: Slingluff=2) and of 60/027,627, filed Oct. 4, 1996 (Dkt: Slingluff=3), both incorporated by reference in their entirety.

CROSS-REFERENCE TO RELATED APPLICATIONS

See PCT/US95/01991, filed Feb. 16, 1995, Ser. No. 08/234,784, filed Apr. 29, 1994, now pending, Ser. No. 08/197,399 filed Feb. 16, 1994, now pending, all hereby incorporated by reference in their entirety.

MENTION OF GOVERNMENT GRANT

Certain aspects of the invention may have been supported by US Public Health Service grants CA57653, AI20963, GM37537 and AI33993. The U.S. Government may have certain rights in the invention.

BACKGROUND OF THE INVENTION

1. Field of the Invention

The present invention is directed to peptides that, in association with Class I MHC molecules, form epitopes recognized by cytotoxic T-cells specific for human melanoma, to immunogens comprising said epitopic peptides, and to related compositions, methods and apparatus.

2. Description of the Background Art

Melanoma affects 30,000 new patients per year in the United States. It is a cancer manifested by the unabated proliferation of melanocytes. Eighty percent of melanoma patients are diagnosed during their productive years between the ages of 25 and 65. The incidence of melanoma is rapidly increasing, in 1935 the lifetime risk of developing melanoma was 1:1,500 individuals, at present, the risk has risen to 1:105. It is believed that by the year 2000 the risk of developing melanoma will increase to about 1:70 to 1:90. Early diagnosis and treatment of this disease is crucial. Once a primary tumor becomes metastatic the disease is almost always fatal.

Cytotoxic lymphocyte (CTL) response has been shown to be an important host defense against malignant cells, Rock et al. J. Immunol., (1993), 150:1244.

Lymphocytes isolated from patients having melanoma, when stimulated in vitro with recombinant interleukin-2 (rIL-2) and autologous melanoma cells, develop a melanoma specific cytotoxic response, Vose et al., Nature, (1982), 296:359; Knuth et al., Proc. Natl. Acad. USA, (1984), 81:3511; Slingluff et al., Arch. Surg., (1987), 122: 1407; Darrow et al., Cancer, (1988), 62:84; Slingluff et al., J. Natl. Cancer Inst., (1988), 80:1016; Slingluff et al., Ann. Surg., (1989), 210:194; Muul et al., J. Immunol., (1987), 138:989; Van den Eynde et al., Int. J. Cancer, (1989), 44:634; Anichini et al., Int. J. Cancer, (1985), 35:683. The majority of melanoma-specific effector lymphocytes are CD8$^+$ cytotoxic T lymphocytes (CTL) that are restricted by class I Major Histocompatibility Complex (MHC) molecules, Vose et al; Slingluff et al (1988), supra, Hersey et al., Cancer Immunol. Immunother., (1986), 22:15. These characteristics are present whether CTL have been generated from peripheral blood lymphocytes (PBL), lymph node cells, or tumor infiltrating lymphocytes.

The evidence that the CTL response to human melanoma is restricted by class I MHC molecules includes demonstration of cross-reactivity for allogenic melanoma cells that share a restricting class I MHC molecule with the autologous tumor. The HLA-A2 molecule and its variants, of which HLA-A2.1 is by far the most common, is an effective restricting element for the melanoma-specific CTL response. Additionally, melanoma-specific HLA-restricted CTL lyse the majority of A2$^+$ melanomas tested, Darrow et al., J. Immunol., (1989), 142:3329; Wolfel et al., J. Exp. Med., (1989), 170:797; Hom et al., J. Immunother., (1991), 3:153. By demonstrating lysis of A2-melanomas transfected with the A2.1 gene, it has been shown that these transfected melanomas can present the epitopes recognized by A2-restricted melanoma-specific CTL, Kawakami et al., J. Immunol., (1992), 148:638. These results suggest that these CTL recognize A2-restricted epitopes that are shared by the majority of melanomas, although very little is known about the number and identity of their epitopes.

Class I molecules of the Major Histocompatibility Complex (MHC) bind to peptides derived from intracellular pathogens or from proteins expressed in tumor cells, and present them on the cell surface to the host immune system. The mechanism of peptide presentation involves protein synthesis and proteolysis in the cytosol, followed by transport of peptides into the endoplasmic reticulum (ER), through the action of the TAP transporter molecules. Peptides then become associated with newly synthesized class 1 molecules, and the resulting complexes move to the cell surface. Proteins that are membrane associated or secreted contain signal sequences that cause them to be contranslationally transferred into the ER from membrane-bound ribosomes. Such proteins would thus be protected from the action of cytoplasmic proteases. However, since peptide epitopes do arise from such proteins, although their TAP dependent expression is unclear, it has been assumed that the proteolysis to generate these peptide epitopes occurs after these proteins have been aberrantly translated on cytoplasmic ribosomes.

Adoptive transfer of tumor stimulated CTL has been associated with some tumor regressions, Rosenberg et al., N. Eng. J. Med., (1988), 319:1676.

An alternate approach to augmenting the T-cell response to melanoma is the use of a vaccine to stimulate CTL in vivo (active specific immunotherapy). Epitopes for CD8$^+$ CTL are believed to be short, usually 9-residue peptides that bind to a cleft on the surface of the class I MHC molecule, Udaka et al., Cell, (1992), 69:989; VanBleek et al., Nature, (1990), 348:213; Falk et al., J. Exp. Med., (1991), 174:425. These peptides, generated from proteolysis of endogenous proteins in the cytosol, are transported to the endoplasmic reticulum, where they become associated with newly synthesized class I MHC molecules. They are then transported to the cell surface, Elliott et al., Nature, (1990), :348:195. CTL epitopes have been reconstituted in vitro by allowing exogenous peptides to bind to MHC molecules on the cell surface of target cells, Townsend et al., Annu. Rev. Immunol., (1989), 7:601. However, because of the complexity of the peptide mixture associated with class I MHC molecules, Hunt et al., Science, (1992), 255:1261, the definition of individual peptides that comprise specific CTL epitopes has proven extremely difficult.

One method has been to generate genomic or cDNA libraries from tumor cells followed by transfection of progressively smaller subsets of these molecular clones into cells that express the appropriate MHC molecule, but not the tumor specific epitope. Molecular clones that encode T cell epitopes are identified by their ability to reconstitute tumor-specific T cell recognition of the transfected cells. The exact T cell epitope is then identified by a combination of molecular subcloning and the use of synthetic peptides based on the predicted amino acid sequence. See, e.g., P. van der Bruggen et al., Science 254, 1643 (1991); C. Traversari, et al., J. Exp. Med. 176, 1453 (1992); B. Gaugler, et al., ibid. 179, 921 (1994); T. Boon, et al., Annu. Rev. Immunol. 12, 337 (1994); A. B. H. Baker, et al., J. Exp. Med. 179, 1005 (1994); Y. Kawakami, et al., Proc. Natl. Acad. Sci. USA 91, 6458 (1994); P. G. Coulie, et al., J. Exp. Med. 180, 35 (1994); Y. Kawakami, et al., ibid. 180, 347 (1994); V. Brichard, et al., ibid. 178, 489 (1993); T. Wolfei, et al., Eur. J. Immunol. 150, 2955 (1993). Unfortunately, it is possible to inadvertently identify clones that encode cross-reacting peptides that are recognized because of their high level of expression in the transfectants.

By this genetic method HLA-A1 restricted T cell epitope (EADPTGHSY) (SEQ ID NO:99 of a melanoma-associated antigen, MAGE-1, was identified. Traversari, et al., J. Exp. Med., 176:1453–57 (1992). MAGE-1 is expressed in about 20–40% of cancers of several different tissue types, including melanomas, breast cancers, non-small cell lung cancers, head and neck squamous cell cancers, and bladder cancer. It is also found in the normal male testis. The MAGE gene family also includes another member, MAGE-3 for which a homologous HLA-A1 restricted CTL epitope Glu Gal Asp Pro Ile Gly His Leu Tyr (SEQ ID NO:96) only after the first priority date. HLA-A1-restricted CTL epitopes are of limited utility because only a minority of melanomas are HLA-A1+. The function of the MAGE gene products is not known.

The genetic approach has also been used to identify HLA-A2.1-restricted CTL epitopes on tyrosinase. This enzyme is not tumor-specific; it is expressed by normal melanocytes as well as melanoma cells. Tyrosinase is involved in melanin biosynthesis. Autologus CTL recognized tyrosinase-derived HLA-A2-restricted epitopes (Tyr met Asn Gly Thr Met Ser Gln Val (SEQ ID NO:94) Wolfel, et al., Eur. J. Immunol., 24:759–64 (1994). However, these peptides were not recognized by the other CTL lines tested.

Another tissue-specific protein, gp100, is the target of the antibody HMB45, which is specific for melanoma and melanocytes. Based on the correlation between HMB45 activity and recognition by a single TIL-derived HLA-A2-restricted melanoma-specific CTL line, Bakker, et al., J. Exp. Med., 179:1005–9 (1994) established that transfection of cells with the gene for gp100 reconstituted the epitope recognized by this T cell. A subsequent study, using the same T-cell line to screen transfected cDNA libraries also identified the peptide Leu Leu Asp Gly Thr Ala Thr Leu Arg Leu (SEQ ID NO:62) as being sufficient to reconstitute activity. This study was not published prior to Applicants' first priority date. Gp100 is believed to play a role in melanin biosynthesis.

An HLA-A2.1 restricted epitope Ala Ala Gly Ile Leu Thr Val (SEQ ID NO: 97) has also been identified genetically in another melanocytic protein, MART-1 (Melan-A). Kawakami, et al., J. Exp. Med., 180:347–52 (1994) and Proc. Nat. Acad. Sci. USA, 91:3515–19 (1994), and see also Coulie, et al., J. Exp. Med., 180:35–42 (1994).

An alternate approach toward characterization of CTL epitopes is to identify them directly. Naturally occurring peptides associated with MHC molecules on the tumor cells are directly extracted, fractionated by HPLC and used to reconstitute recognition by tumor specific CTL of a non-tumor cell expressing appropriate MHC molecules. Sequencing can be performed by Edman degradation. Mandelboim, et al., Nature, 369:67–71 (1994) (CTL epitope on murine lung carcinoma). However, Applicants pioneered the use of tandem mass spectrometry to evaluate HHC-associated peptides. C. L. Slingluff, et al., J. Immunol. 150, 2955 (1993); D. F. Hunt, et al., Science 255, 1261 (1992); R. A. Henderson, et al., Proc. Natl. Acad. Sci. USA 90, 10275 (1993).

However, when peptides associated with MHC molecules on tumor cells are extracted, a complex mixture, of up to 10,000–20,000 different peptides of similar size (mostly nonamers), is obtained. Within this mixture, only a small number of molecules are likely to correspond to the peptides of interest. Consequently, their isolation and sequencing was extremely difficult. Boon, et al., Ann. Rev. Immunol., 12:337–65 (1994) states, "to our knowledge, the peptide elution method has not yet ensured the identification of a peptide recognized by anti-tumor CTL". More colorfully, Finn, et al., Curr. Op. Immunol., 5:701–8 (1993) likened the process to "throwing a fish hook into the ocean, hoping to catch the big one", given, inter alia, the "very low amounts of peptides".

In the present invention, HLA associated peptides have been extracted, isolated and identified from different melanoma lines. These peptides can be used to reconstitute epitopes for HLA-A2.1- and HLA-A3-restricted melanoma-specific CTL. These peptides and the stimulated CTL may be useful for the in vivo immunotherapeutic treatment of melanoma. Aspects of applicants' invention were described in Cox, et al., Science, 264:716–719 (1994), which was published on Apr. 29, 1994.

SUMMARY OF THE INVENTION

The present invention relates to immunogens which are capable of eliciting a melanoma-specific cytotoxic lymphocyte response in at least some individuals, which response is directed to peptide epitopes carried by those immunogens, and to the use of those immunogens in active specific immunotherapy and immunoprophylaxis against melanoma.

These immunogens may be used as vaccines, in active specific immunotherapy. The immunogens may be administered directly or by gene therapy. The epitopic peptides may also be used to stimulate lymphocytes, the latter then being used for adoptive immunotherapy.

In one embodiment, a CTL epitope of the present invention is a sequence which is at least substantially homologous with a CTL epitope of the melanoma antigens pMel-17 and gp100, (these two antigens are essentially identical). One such epitope is the peptide 946L. Peptide 946I is substantially homologous to peptide 946L.

In another embodiment, a CTL epitope of the present invention is a sequence which is at least substantially homologous with a CTL epitope of tyrosinase. One such epitope is the peptide Lys-Cys-Asp-Ile-Cys-Thr-Asp-Glu-Tyr (SEQ ID NO:93).

Peptides 946I and 946L, related to a single segment in pMel-17 (a protein homologous to gp100), had unexpectedly high A2.1 CTL stimulatory activity. They also are recognized by CTL from different individuals.

Another pMel-17-derived peptide Ala Leu Leu Ala Val Gly Ala Thr Lys (SEQ ID NO:98) had acceptable A3 CTL stimulatory activity, and is the first HLA-A3-associated stimulatory peptide identified in pMel-17 and one of the few, if any, A3-associated peptides identified in melanoma antigens generally.

Peptide SEQ ID NO:93 is the first A1-restricted epitope to be identified in tyrosinase and one of the few such epitopes identified in melanoma antigens generally (A1 epitopes have been identified in MAGE-1 Glu Ala Asp Pro Thr Gly His Ser Tyr (SEQ ID NO:99) 3 (SEQ ID NO:96).

It is advantageous to be able to elicit a melanoma-specific CTL response from one or more A1-, A2.1- and/or A3-FIG. 19. restricted CTLs, and preferably all of them. In a similar manner, a melanoma-specific CTL response may be elicited which is restricted by other MHC molecules.

Additional embodiments of the present invention are described below.

BRIEF DESCRIPTION OF THE DRAWINGS

FIG. 1 is a graph of the specificity of VMM5 CTL on day 39;

FIG. 2 is a graph illustrating the specificity of VMM5 CTL FIG. 2A, line VMM5; FIG. 2B, line AX21-9 against a panel of 13 targets;

FIG. 15A Melanoma specific recognition of autologous tumor by VMM18 CTL. VMM18 cells (solid squares) were lysed by the CTL in a 4 h $^{51}$Cr release assay, while minimal lysis of non-melanoma targets K562 (open squares), VMM12-EBV (open circles) and the HLA-A3-melanoma DM6 (open triangles) was observed.

FIG. 15B Recognition of VMM18 melanoma by VMM18 CTL was restricted by the class I MHC molecule HLA-A3. Lysis of autologous melanoma was inhibited after incubation of target cells with W6/32 (solid diamonds) and GAP-A3 (solid squares) MAbs, specific for class I MHC and HLA-A3 respectively. Incubation with L243 (open circles) had little effect on recognition of autologous melanoma. Specific lysis of autologous melanoma was 65% (dotted line), while lysis of VMM12-EBV was 1.5% (solid line). The effector:target ratio used was 10:1.

FIG. 19. Recognition of autologous and HLA-matched melanomas by melanoma-reactive CTL. In 19A), VMM12 CTL are evaluated for lysis of a panel of target cells. The VMM12 CTL recognize shared melanoma antigens presented by HLA-A1 (VMM15 melanoma cells share HLA-A1 with VMM12), and by HLA-A3 (VMM10 melanoma cells share HLA-A3 with VMM12). Similarly, in 19B), VMM15 CTL are evaluated in the same manner. VMM15 CTL recognize shared melanoma antigens presented by HLA-A1 (VMM12 melanoma cells) and by either HLA-A1, -A25, or -B8 (VMM14 melanoma cells).

FIG. 21. List of peptides synthesized and tested for recognition by VMM12 and VMM15 CTL. These peptides were predicted from the defined sequence of tyrosinase, accounting for some possible alternate sequences and for possible post-translational modifications. Those listed in the 3rd synthesis were not tested. FIGS. 21A–D refers to syntheses 1–4, respectively.

FIG. 22. VMM15 CTL recognize peptides containing Lys Cys Asp Ile Cys Thr Asp Glu Tyr (SEQ ID NO:93)in association with HLA-A1. C1R-A1 cells were pulsed with 10 uM, 1 uM and 0.1 uM concentrations of synthetic peptides prior to addition of VMM15 CTL. Background lysis of C1R was approximately 10w. Direct cytotoxicity by the peptides themselves was negligible (open diamonds), averaging 0–2%. An epitope for VMM15 CTL was reconstituted by three of the test peptides, numbers 5, 12 and 15, corresponding to (SEQ ID NO:93); and Asp Ala Glu Lys Cys Asp Ile Cys Thr Asp Glu Tyr (SEQ ID NO:101) (FIG. 5A), or negative control extracts (FIG. 5B), and Glu Lys Cys Asp Ile Cys Thr Asp Glu Tyr (SEQ ID NO:102)

FIG. 24. Amino acid sequence of tyrosinase, with the position of (SEQ ID NO:93) highlighted and underlined. The high proportion of cystine residues and acidic residues are noted relative to the proportion in the intact protein.

DETAILED DESCRIPTION OF THE PREFERRED EMBODIMENTS OF THE INVENTION

Figure 3:
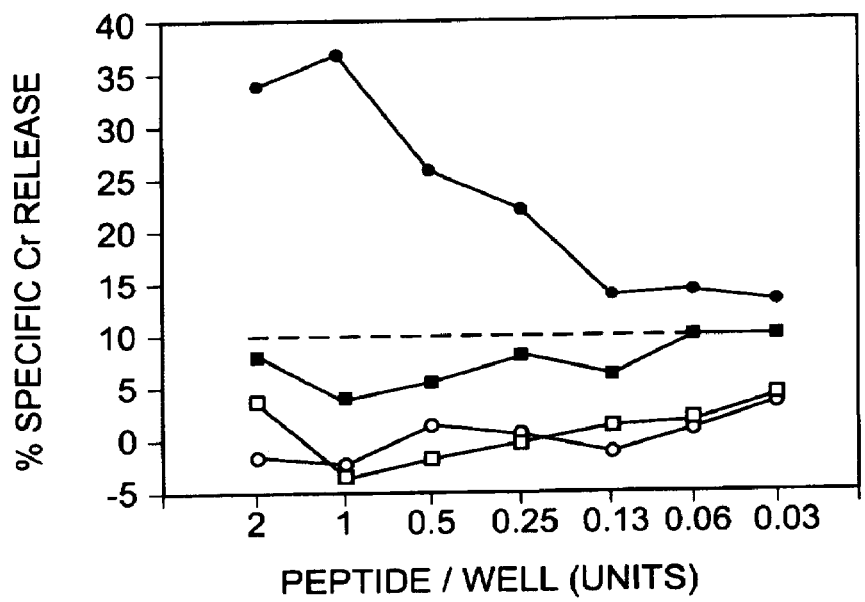
FIG. 3 is a graph of the reconstitution of HLA-A2.1—restricted melanoma—specific epitopes for CTL using peptides eluted from A2.1 molecules on DM93.

The present invention relates to certain melanoma-specific CTL epitopes, and their incorporation into immunogens for immunoprophylactic and immunotherapeutic purposes. For the purpose of the present invention, a melanoma-specific CTL epitope is an epitope which is recognized by a T-cell receptor of at least some cytotoxic lymphocytes of at least some individuals in the population of interest, and which is more frequently or strongly associated with melanoma cells than with at least some other cancer and/or normal cells. There may be some cross-reactivity, for example, with other cells of melanocytic lineage. Absolute specificity is not required, provided that a useful prophylactic, therapeutic or diagnostic effect is still obtained.

Melanoma-Specific CTL Epitopes

The melanoma-specific CTL epitopes of the present invention are peptides, typically 9–13 amino acids in length, which are sufficiently similar to a melanoma-specific epitope recognized by a melanoma-specific CTL to be useful, under suitable conditions of use, to protect an individual from melanoma, or to be useful in the diagnosis of melanoma or of a patient's ability to fight a melanoma by a CTL response. Preferably, these epitopes are identical to or otherwise substantially homologous with melanoma-specific peptide epitopes recognized by melanoma-specific CTLs.

The family of melanoma epitopes which are recoverable from an individual is dependent on the nature of the binding site of the Class I MHC (HLA) molecules expressed by the individual, and, as a result of the polymorphism of the Class I MHC (HLA) molecules, can vary considerably from one individual to another. For the purpose of the present invention, the melanoma cell line used as a source of melanoma-specific CTL epitopes may be any melanoma cell line; similarly, the Class I MHC (HLA) molecule may be any such molecule borne by a melanoma which is capable of binding to and presenting a melanoma-specific epitope, including, but not limited to, the various allelic forms of Class I MHC molecules, including but not limited to those enumerated in Table I. Among the Class I molecules, the principal genetic loci are denoted as HLA-A, HLA-B, and HLA-C. The preferred epitopic sequence may vary depending on the restriction system.

Application of active specific immunotherapy to a heterogeneous melanoma patient population would be facilitated by identification of CTL epitopes presented in association with a wide range of class I MHC molecules. Besides HLA-A2, the most commonly expressed class I MHC molecules are A1 and A3, then B7 and B8. Approximately 90% of the melanoma patient population should express one or more of these molecules or HLA-A2. Peptides from MAGE-1 and MAGE-3 have been identified as HLA-A1-restricted CTL epitopes, and a few peptides have been identified for some of the less common MHC molecules, including A24, A31, and B44. Little work has been done toward identification of HLA-A3-restricted responses, and except for the peptides from MAGE proteins—little work has been done toward identification of HLA-A1-restricted responses.

Preferably, the epitope is one restricted by one of the more prevalent forms (in the melanoma patient population) of these loci. The loci HLA-A1, HLA-A2, HLA-A3, HLA-B7 and HLA-B8 are of greatest interest. Within HLA-A2, HLA-A2.1 is of particular interest.

Preferably, the CTL epitopes of the present invention, in the cytotoxicity assay described hereafter, when used in oligopeptide form to reconstitute epitopes for suitable CTL, achieve, at the dosage resulting in maximal lysis of target cells exposed to the stimulated CTL, a percentage lysis of target cells which is at least 10 percentage points higher (more preferably, at least 20 points higher) the background level of lysis of the target cells by the CTLs (i.e., in absence of the peptide).

Preferably, the peptide concentration at which the epitope-stimulated CTLs achieve half the maximal increase in lysis relative to background is no more than about 1 mM, preferably no more than 1 μM, more preferably no more than about 1 nM, still more preferably no more than about 100 pM, most preferably no more than about 10 pM. For the peptides 946L and 946I, half-maximal lysis of T2 cells is observed with concentrations of peptide in the pM range. In contrast, the MAGE-1 peptide EADPTGHSY had half-maximal lysis between 1 and 100 nM (prob about 10); while the tyrosinase peptides (SEQ ID NO:94) and (SEQ ID NO:95) reported by Boon induced half-maximal lysis (even with pre-treatment with MA2.1 antibody) at over 10 nM.

(SEQ ID NO: 98) is at present the only pMel-17 derived peptide known to be immunogenic in the context of HLA-A3, which is expressed by 20% of the patient population. It achieves half-maximal lysis of T2 cells expressing HLA-A3 at a concentration of about 10 nM. While not as potent as our A2.1 peptides, its potency is acceptable.

Preferably the epitope is recognized by CTLs from at least two different individuals, more preferably at least five different individuals.

More preferably, the CTL epitope satisfies two or more of the above desiderata.

The 946L peptide, although recognized by HLA-A2.1-restricted melanoma-specific CTL, may not be optimal at present. It is known that some residues on the nonamer peptide are particularly important for binding of the peptide to the MHC molecule (residues 2,9), while others are particularly important for Tc recognition (residues 4–8). The other residues may be important for either or both. It is proposed that amino acid substitutions for the 946 peptide may be useful at increasing immunogenicity, particularly by attempting to change residues that may increase binding to the MHC such as changing residue 9 to a valine or residue 3 to anything other than glutamic acid (E). Using existing knowledge about which of these residues may be more likely to affect binding either to the MHC or to the TcR, a rational approach to this process may be employed. The resulting peptides, if more effective, could be used for any of the purposes described herein. (refs: E. L. Huczko et al. J. Immunol. 151:2572, 1993; J. Ruppert et al. Cell 74: 929, 1993; Madden Dr et al. Cell 75:693–708, 1993.) It is possible to predict peptides binding to specific Class I MHC molecules by identifying amino acid sequences fitting described binding motifs within known protein sequences. In attempting to identify epitopes for melanoma-specific CTL, these peptides can be screened for their ability to sensitize non-melanoma targets for recognition by melanoma specific CTL.

Therefore, in addition to epitopes which are identical to the naturally occurring melanoma-specific epitopes, the present invention embraces epitopes which are substantially homologous with such epitopes, and therefore melanoma-specific in their own right.

The term "substantially homologous", when used in connection with amino acid sequences, refers to sequences which are substantially identical to or similar in sequence with each other, giving rise to a homology in conformation and thus to similar (or improved) biological activity. The term is not intended to imply a common evolution of the sequences.

An epitope is considered substantially homologous to a reference epitope if it has at least 10% of an immunological activity of the reference epitope and differs from the reference epitope by no more than one non-conservative substitution not suggested by a known binding motif of the pertinent MHC molecule. Any number of highly conservative, conservative or semi-conservative substitutions, or non-conservative substitutions suggested by known binding motifs, subject to the activity limitation, are permitted.

Kast, et al., J. Immunol, 152:3964–12 (1994) sets forth HLA-A specific peptide binding motifs for the HLA molecules A1, A2.1, A3, A11 and A24. Engelhard, et al., in Sette, ed., Naturally Processed Peptides, 57:39–62 (1993) explored the features that determined binding to HLA-A2.1 and HLA-B7. See also Habohm et al; Eur. J. Immunol., 23:1271–6 (1993); Kawakami, et al., J. Immunol., 154: 3961–8 (1995). Based on these and other sources, the preferred and tolerated AAs for various HLA molecules include (but are not limited to) the following:

TABLE 10

| Molecule | Position | Preferred AA | tolerated AA |
| --- | --- | --- | --- |
| A1 | 2 | T, S, M | |
| | 3 | D, E | A, S |
| | 9 | Y | |
| A2.1 | 2 | L, M | I, V, A, T |
| | 9 | L, V, I | A, M, T |
| A3 | 2 | L, M, I, V, S, A, T, F | C, G, D |
| | 9 | K, R, Y, H, F | A |
| A11 | 2 | M, L, I, V, S, A, T, G, N | C, D, F |
| | 9 | K | R, H, Y |
| A24 | 2 | Y, F, W | M |
| | 9 | F, L, I, W | |
| B7 | 1 | A | M, S, R, L |
| | 2 | P | V |
| | 3 | R | A, K, S, M |
| | 9 | L | I, A, V |
| B8 | 3 | K | not known |
| | 5 | K | not known |
| | 9 | L | not known |
| B27 | 2 | R | not known |
| | 9 | R, K, H | not known |
| B35 | 2 | P | not known |
| | 9 | Y | not known |
| B53 | 2 | P | not known |

If a position is not listed, studies revealed a greater variability of AAs than for the listed positions. For listed positions; AAs not listed may be tolerated, especially if they are conservative or semi-conservative substitutions for "preferred" or "tolerated" AAs.

An example of a peptide variant which satisfies the known binding motif is (SEQ ID NO:103) Tyr Leu Glu Pro Gly Pro Val Thr VAl (SEQ ID No:14). This differs from 946L at position 9. However, V is a preferred a.a: at position 9 of HLA-A2.1 binding peptides.

Substantially homologous peptide epitopes may be identified by a variety of techniques. It is known in the art that one may synthesize all possible single substitution mutants of a known peptide epitope. For a nonpeptide, there are (20×9–1=179) such mutants. Geysen, et al., Proc Nat. Acad. Sci. (USA), 81:3998–4002 (1984). While the effects of different substitutions are not always additive, it is reasonable to expect that two favorable or neutral single substitutions at different residue positions in the epitope can safely be combined in most cases.

One may also synthesize a family of related single or multiple substitution mutants, present the mixture to the HLA-A2.1 positive lymphoblastoid cell line T2 (or other cell line capable of presenting melanoma-specific CTL epitopes), and expose the T2 cells to melanoma-specific CTLs. If the T2 cells are lysed, the effective epitopes may be identified either by direct recovery from the T2 cells or by a progressive process of testing subsets of the effective peptide mixtures. Methods for the preparation of degenerate peptides are described in Rutter, U.S. Pat. No. 5,010,175, Haughten, et al., Proc. Nat. Acad. Sci. (USA), 82:5131–35 (1985), Geysen, et al., Proc. Nat. Acad. Sci. (USA), 81:3998–4002 (1984); WO86/06487; WO86/00991.

Multiple mutagenesis may be used to screen a few residue positions intensely or a larger number of positions more diffusely. One approach is to explore at least a representative member of each a.a. type at each position, e.g., one representative of each of exchange groups I–V as hereafter defined. Preferably, Gly and Pro are screened in addition to one other group I residue. Preferably, at least one screened residue is an H-bonding resiude. If a positive mutant features a particular representative, like amino acids can be explored in a subsequent library. If, for example, a Phe substitution improves binding, Tyr and Trp can be examined in the next round.

In the case of the peptide 946L (SEQ. ID. No.:14), a possible multiple mutagenesis strategy would be as follows:

| Parental | Tyr | Leu | Glu | Pro | Gly | Pro | Val | Thr | Ala |
| --- | --- | --- | --- | --- | --- | --- | --- | --- | --- |
| Possible Mutations | Phe | Ile | Asp | Ala | Pro | Ala | Ile | Ala | Thr |
| | Trp | Val | | Ser | Ala | Ser | Leu | Ser | Ser |
| | | Met | | Thr | Ser | Thr | Met | Pro | Pro |
| | | Ala | | Gly | Thr | Gly | | Gly | Gly |
| | | Thr | | | | | | | Leu |
| | | | | | | | | | Val |
| | | | | | | | | | Ile |
| | | | | | | | | | Met |

For peptide 1030 (SEQ. ID NO.:9), a possible strategy would be:

| Parental | Tyr | Met | Asp | Gly | Thr | Met | Ser | Gln | Val |
|---|---|---|---|---|---|---|---|---|---|
| | Phe | Val | Glu | Pro | Ala | Val | Ala | Asn | Ile |
| | Trp | Ile | | Ala | Ser | Ile | Thr | | Leu |
| | | Leu | | Ser | Pro | Leu | Pro | | Met |
| | | Ala | | Thr | Gly | | Gly | | Ala |
| | | Thr | | | | | | | Thr |

Other strategies are, of course, possible. For example, the Asp/Glu and Gln/Asn sets can be merged. It is known from comparison of peptide 1030 with the homologous tyrosinase segment that substitution of Asn for Asp in position 3 reduces CTL activity 100-fold. However, a multiple mutagenesis strategy could identify compensating mutations at other sites.

For our preferred A3 peptide, a possible multiple mutagenesis strategy would be

| Ala | Leu | Leu | Ala | Val | Gly | Ala | Thr | Lys |
|---|---|---|---|---|---|---|---|---|
| Thr | Ile | Ile | Thr | Ile | Ala | Thr | Gly | Arg |
| Ser | Val | Val | Ser | Leu | Thr | Ser | Ala | His |
| Pro | Met | Met | Pro | Met | Ser | Pro | Ser | Tyr |
| Gly | Ser | | Gly | | Pro | Gly | Pro | Phe |
| | Cys | | | | | | | Ala |
| | Gly | | | | | | | |
| | Asp | | | | | | | |
| | Ala | | | | | | | |
| | Thr | | | | | | | |
| | Phe | | | | | | | |

For our preferred A1 peptide, a possible multiple mutagenesis strategy would be

| Lys | Cys | Asp | Ile | Cys | Thr | Asp | Glu | Tyr |
|---|---|---|---|---|---|---|---|---|
| Arg | Thr | Glu | Leu | Thr | Ala | Glu | Asp | Phe |
| His | Ser | | Val | Ser | Ser | | | Trp |
| | Ala | | Met | Ala | Pro | | | |
| | Met | | | Gly | Gly | | | |

These strategies take into account both conservative substitutions for the wild type AAs, and the known A1, A2.1 and A3 binding motifs.

The person of ordinary skill in the art, in determining which residues to vary, may also make comparisons of the sequences of the naturally processed MHC associated peptides, and may obtain 3D structures of the MHC: peptide: TCR complexes, in order to identify residues involved in MHC or TCR binding. Such residues may either be left alone, or judiciously mutated in an attempt to enhance MHC or TCR binding.

It is also possible to predict substantially homologous epitopes by taking into account studies of sequence variations in families of naturally occurring homologous proteins. Certain amino acid substitutions are more often tolerated than others, and these are often correlatable with similarities in size, charge, etc. between the original amino acid and its replacement. Insertions or deletions of amino acids may also be made. N- and C-terminal truncations or extensions are more likely to be tolerated than internal deletions or insertions. With regard to truncation, the peptide may be truncated by one or more amino acids and still be substantially homologous, however, it cannot be fewer than five amino acids. Extensions are permissible, however, note that larger peptides are digested in vivo prior to presentation.

Conservative substitutions may be made in the amino acid sequence of the proteins of interest without compromising the desired properties of the peptides, i.e., induction of cytotoxic T-lymphocytes in a patient when administered thereto.

Conservative substitutions are herein defined as exchanges within one of the following five groups:

I. Small aliphatic, nonpolar or slightly polar residues:
Ala, Ser, Thr, Pro, Gly II. Polar, negatively charged residues: and their amides
Asp, Asn, Glu, Gln III. Polar, positively charged residues:
His, Arg, Lys IV. Large, aliphatic, nonpolar residues:
Met, Leu, Ile, Val, Cys V. Large, aromatic residues:
Phe, Tyr, Trp Within the foregoing groups, the following substitutions are considered "highly conservative":

Asp/Glu
His/Arg/Lys
Phe/Tyr/Trp
Met/Leu/Ile/Val

Semi-conservative substitutions are defined to be exchanges between two of groups (I)–(V) above which are limited to supergroup (A), comprising (I), (II) and (III) above, or to supergroup (B), comprising (IV) and (V) above. Also, Ala is considered a semi-conservative substitution for all-non group I amino acids.

It will be appreciated that highly conservative substitutions are less likely to affect activity than other conservative substitutions, conservative substitutions are less likely to affect activity than merely semi-conservative substitutions, and semi-conservative substitutions less so than non-conservative substitutions.

Although a substitution mutant, either single or multiple, of the peptides of interest may not have quite the potency of the original peptide, such a mutant may well be useful.

Substitutions are not limited to the genetically encoded, or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluoro-phenylalanine, D- or L-p-biphenylphenylalanine, D- or L-p-methoxybiphenylphenylalanine, D- or L-2-indole-(alkyl) alanines, and D- or L-alkylainines where alkyl may be substituted or unsubstituted methyl, ethyl, propyl, hexyl, butyl, pentyl, iso-propyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —SO$_3$H) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage can be replaced by a ketomethylene moiety, e.g. (—C(=O)—CH$_2$—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D-amino acid but which can additionally be referred to as the R— or the S—, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

The thiol group of cysteine reacts very rapidly with alkyl halides, such as iodoacetate, iodoacetamide, methyl iodine, and so on, to give the corresponding stable alkyl (substituted or unsubstituted) derivatives, such as —CH$_2$—S—CH$_3$. The thiol group can also add across double bonds such as those of N-ethylmaleimide or of maleic anhydride, and it can open the ring of ethyleneimine, providing a new site for tryptic cleavage. Thiols form complexes with various metal (especially mercury, silver, arsenic, copper, iron, zinc, cobalt, molybdenum, manganese and cadmium ions) and organometal ions (e.g., R—Hg$^+$, such as para-mercuribenzoic acid).

The thiol group may be oxidized to yield a disulfide bond or a sulfonate. A thiol may be converted to a disulfide by thiol-disulfide exchange, for example, exchange with an aromatic disulfide such as dithionitrobenzoic acid (DTNB) or Ellman's reagnet. Of course, a cysteine residue may be disulfide bonded to a cysteine residue in the same or a different peptide, or to a free cysteine. By way of further examples, some of which are already embraced by the general discussion above, cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alp-ha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and -glutamyl residues may be converted to asparaginyl and glutaminyl residues by reaction with ammonium ions.

Glutaminyl and asparaginyl residues may be readily deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'—dithiobis(succinimidylpropionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecule Properties, W.H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps. Glycosylation is also possible.

Derivatized moieties may impart altered affinity for their target, altered immunogenicity, or improved solubility, absorption, biological half life, and the like, or attenuated undesirable side effects. Moieties capable of mediating such effects are disclosed, for example, in Remington's Pharmaceutical Sciences, 16th ed., Mack Publishing Co., Easton, Pa. (1980).

Modifications are not limited to the side chains of the amino acids. One may also modify the peptidyl linkage itself, e.g., —NRCO— (where R is alkyl or aryl), instead of —NHCO—, as in the so-called "peptoids."

The peptides may also comprise isoteres of two or more residues in the immunogenic peptide. An isotere as defined here is a sequence of two or more residues that can be sustituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, peptides and Proteins, Vol. VII (Weinstein ed., 1983).

It is also possible to construct and use so-called peptide mimetics whose conformation is similar to that of a peptide but do not have a peptide-like molecular formula. In effect, in a mimetic, all of the residues of the peptide are replaced by one or more isoteres as defined above.

The Melanoma-Specific Immunogen

The melanoma-specific immunogen of the present invention is a molecule corresponding to or otherwise comprising a melanoma-specific CTL epitope as previously described. The immunogen may comprise one or more melanoma-specific CTL epitopes, which may be the same or different. Preferably, the immunogen is chosen so that at least one epitope is effective in each of two or more restriction systems, e.g., HLA-A2 and HLA-A3. In some instances, a single epitope may be effective in more than one restriction system. For example HLA-A2 and HLA-69, or HLA-A3 and HLA-A11, are pairs of MHC molecules having similar peptide binding motifs. Otherwise, for the immunogen to be effective in more than one restriction system, two or more epitopes (at least one for each MHC molecule of interest) will need to be provided. These epitopes may be separate or overlapping.

It should be noted that instead of linking epitopes within a single immunogen, the compositions of the present invention may include two or more immunogens which present different epitopes.

If the immunogen comprises a plurality of such epitopes, they may be linked directly, or through a spacer of some kind, or by noncovalent means such as an avidin:biotin complex. The immunogen may take any form that is capable of eliciting a melanoma-specific cytotoxic immune response. By way of example and not of limitation, the immunogen may be a fusion of a plurality of CTL epitopes which is sufficiently large to be immunogenic, a conjugate of one or more epitopes to a soluble immunogenic macromolecular carrier, such as serum albumin, keyhole limpet hemocyanin, or dextran, a recombinant virus engineered to display the epitope on its surface, or a conjugate of a plurality of epitopes to a branched lysine core structure, a so-called "multiple antigenic peptide" (see Posnett, et al., J. Biol. Chem., 263:1719–25, 1988).

The immunogenic conjugate may also comprise moieties intended to enhance the immune response, such as a T helper peptide, a cytokine or an adjuvant; a targeting agent, such as an antibody or receptor ligand or ligand analogue; on a stabilizing agent, such as a lipid.

[3] BAGE: expressed in Melanoma (22%), Bladder CA (15%), Breast CA (10%), Head and neck CA (<10%), NSCLC (<10%) [50]

[4] GAGE-1, -2: expressed in Melanoma (24%), Bladder CA (12%), Breast CA (9%), Head & neck CA (19%), NSCLC (19%), Sarcomas (25%), Prostate cancers (10%) [50]

[5] Isoleucine (I) at position 5 is the result of mutation. The wild type sequence si EEKLSVVLF (SEQ ID NO: 293).

[6] Phenylalanine (F) at pos. 9 is the result of mutation. The wild type sequence is SYLDSGIHS (SEQ ID NO:294).

If it is desirable to present more than one CTL epitope, rather than presenting all of the epitopes on a single immunogen, they may be presented on two or more different immunogens. These may be administered separately, or as part of a mixture, e.g., a mixture of epitopic peptides.

Mode of Production

The peptide portion of the immunogens of the present invention may be produced by any conventional technique, including
  (a) nonbiological synthesis by sequential coupling of component amino acids,
  (b) production by recombinant DNA techniques in a suitable host cell, and
  (c) chemical or enzymatic modification of a sequence made by (a) or (b) above.

Gene Expression. The peptides disclosed herein may be produced, recombinantly, in a suitable host, such as bacteria from the genera Bacillus, Escherichia, Salmonella, Erwinia, and yeasts from the genera Hansenula, Kluyveromyces, Pichia, Rhinosporidium, Saccharomyces, and Schizosaccharomyces, or cultured mammalian cells such as COS-1. The more preferred hosts are microorganisms of the species Pichia pastoris, Bacillus subtilis, Bacillus brevis, Saccharomyces cerevisiae, Escherichia coli and Yarrowia lipolytica. Any promoter, regulatable or constitutive, which is functional in the host may be used to control gene expression.

It has been found that peptide fragments from the protein pMEL17 reconstitute HLA A2.1 and A3 epitopes. The pMEL17 gene is a single-stranded cDNA reading 5' to 3'. The gene encoding for pMEL17, SEQ. ID. NO. 91 is:

```
GGAAGAACAC   AATGGATCTG   GTGCTAAAAA   GATGCCTTCT   TCATTTGGCT

GTGATAGGTG   CTTTGCTGGC   TGTGGGGGCT   ACAAAAGTAC   CCAGAAACCA

GGACTGGCTT   GGTGTCTCAA   GGCAACTCAG   AACCAAAGCC   TGGAACAGGC
```

-continued

```
AGCTGTATCC   AGAGTGGACA   GAAGCCCAGA   GACTTGACTG   CTGGAGAGGT
GGTCAAGTGT   CCCTCAAGGT   CAGTAATGAT   GGGCCTACAC   TGATTGGTGC
AAATGCCTCC   TTCTCTATTG   CCTTGAACTT   CCCTGGAAGC   CAAAAGGTAT
TGCCAGATGG   GCAGGTTATC   TGGGTCAACA   ATACCATCAT   CAATGGGAGC
CAGGTGTGGG   GAGGACAGCC   AGTGTATCCC   CAGGAAACTG   ACGATGCCTG
CATCTTCCCT   GATGGTGGAC   CTTGCCCATC   TGGCTCTTGG   TCTCAGAAGA
GAAGCTTTGT   TTATGTCTGG   AAGACCTGGG   GCCAATACTG   GCAAGTTCTA
GGGGGCCCAG   TGTCTGGGCT   GAGCATTGGG   ACAGGCAGGG   CAATGCTGGG
CACACACACC   ATGGAAGTGA   CTGTCTACCA   TCGCCGGGGA   TCCCGGAGCT
ATGTGCCTCT   TGCTCATTCC   AGCTCAGCCT   TCACCATTAC   TGACCAGGTG
CCTTTCTCCG   TGAGCGTGTC   CCAGTTGCGG   GCCTTGGATG   GAGGGAACAA
GCACTTCCTG   AGAAATCAGC   CTCTGACCTT   TGCCCTCCAG   CTCCATGACC
CTAGTGGCTA   TCTGGCTGAA   GCTGACCTCT   CCTACACCTG   GGACTTTGGA
GACAGTAGTG   GAACCCTGAT   CTCTCGGGCA   CCTGTGGTCA   CTCATACTTA
CCTGGAGCCT   GGCCCAGTCA   CTGCCCAGGT   GGTCCTGCAG   GCTGCCATTC
CTCTCACCTC   CTGTGGCTCC   TCCCCAGTTC   CAGGCACCAC   AGATGGGCAC
AGGCCAACTG   CAGAGGCCCC   TAACACCACA   GCTGGCCAAG   TGCCTACTAC
AGAAGTTGTG   GGTACTACAC   CTGGTCAGGC   GCCAACTGCA   GAGCCCTCTG
GAACCACATC   TGTGCAGGTG   CCAACCACTG   AAGTCATAAG   CACTGCACCT
GTGCAGATGC   CAACTGCAGA   GAGCACAGGT   ATGACACCTG   AGAAGGTGCC
AGTTTCAGAG   GTCATGGGTA   CCACACTGGC   AGAGATGTCA   ACTCCAGAGG
CTACAGGTAT   GACACCTGCA   GAGGTATCAA   TTGTGGTGCT   TTCTGGAACC
ACAGCTGCAC   AGGTAACAAC   TACAGAGTGG   GTGGAGACCA   CAGCTAGAGA
GCTACCTATC   CCTGAGCCTG   AAGGTCCAGA   TGCCAGCTCA   ATCATGTCTA
CGGAAAGTAT   TACAGGTTCC   CTGGGCCCCC   TGCTGGATGG   TACAGCCACC
TTAAGGCTGG   TGAAGAGACA   AGTCCCCCTG   GATTGTGTTC   TGTATCGATA
TGGTTCCTTT   TCCGTCACCC   TGGACATTGT   CCAGGGTATT   GAAAGTGCCG
AGATCCTGCA   GGCTGTGCCG   TCCGGTGAGG   GGGATGCATT   TGAGCTGACT
GTGTCCTGCC   AAGGCGGGCT   GCCCAAGGAA   GCCTGCATGG   AGATCTCATC
GCCAGGGTGC   CAGCCCCCTG   CCCAGCGGCT   GTGCCAGCCT   GTGCTACCCA
GCCCAGCCTG   CCAGCTGGTT   CTGCACCAGA   TACTGAAGGG   TGGCTCGGGG
ACATACTGCC   TCAATGTGTC   TCTGGCTGAT   ACCAACAGCC   TGGCAGTGGT
CAGCACCCAG   CTTATCATGC   CTGTGCCTGG   GATTCTTCTC   ACAGGTCAAG
AAGCAGGCCT   TGGGCAGGTT   CGGCTGATCG   TGGGCATCTT   GCTGGTGTTG
ATGGCTGTGG   TCCTTGCATC   TCTGATATAT   AGGCGCAGAC   TTATGAAGCA
AGACTTCTCC   GTACCCCAGT   TGCCACATAG   CAGCAGTCAC   TGGCTGCGTC
TACCCCGCAT   CTTCTGCTCT   TGTCCCATTG   GTGAGAATAG   CCCCCTCCTC
AGTGGGCAGC   AGGTCTGAGT   ACTCTCATAT   GATGCTGTGA   TTTTCCTGGA
GTTGACAGAA   ACACCTATAT   TTCCCCCAGT   CTTCCCTGGG   AGACTACTAT
TAACTGAAAT   AAATACTCAG   AGCCTGAAAA   A
```

The peptide 946L (SEQ. ID NO:14) (SEQ. ID NO: 14) reconstitutes an A2.1 epitope. Its encoding gene sequence is (SEQ. ID. NO. 90) TAC CTG GAG CCT GGC CAA GTC ACT GCC. Because this peptide has proven immunologic activity, it is ideal for specific immunization. Such immunization may be accomplished either directly, or by use of a vaccine consisting of virus (e.g., Vaccinia)encoding or HLA-A2 cells expressing a genetic sequence encoding this peptide. The peptide of (SEQ ID NO:98) which corresponds to residues 17–25 of pMel-17, reconstitutes an A3 epitope.

Also promising is the gene sequence encoding tyrosinase-related peptide 1030, Tys Met Asp Gly Thr Met Ser Gln Val (SEQ ID NO:9) TAT ATG GAT GGA ACA ATG TCC GAG GTA (SEQ. ID. NO.:92), which reconstitutes an A2-epitope, and that encoding SEQ ID NO:93, which reconstitutes an A1 epitope of tyrosinase.

The Genetic Code can readily be used to design a gene encoding an arbitrary amino acid sequence, such as that of the preferred HLA-A3 epitope, (SEQ ID NO:98) Preferably, where more than one codon could be used to encode a particular amino acid, consideration is given to the codon preferences of the intended host organism.

These sequences may be constructed in such a manner, including the appropriate expression systems for use in gene therapy procedures. Because several different nucleotide sequences may encode a single amino acid, alternate DNA sequences may also encode these peptides.

Standard reference works setting forth the general principles of recombinant DNA technology include Watson, J. D., et al., *Molecular Biology of the Gene*, Volumes I and II, The Benjamin/Cummings Publishing Company, Inc., publisher, Menlo Park, Calif. (1987); Darnell, J. E., et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering,* 2d edition, University of California Press, publisher, Berkeley, Calif. (1981); Sambrook, J., et al., *Molecular Cloning: A Laboratory Manual*, Cold Spring Harbor Laboratory, Cold Spring Harbor, NY (1989); and Ausubel, et al., *Current Protocols in Molecular Biology*, Wiley Interscience, N.Y., (1987, 1992). These references are herein entirely incorporated by reference.

Chemical Peptide Synthesis. Chemical peptide synthesis is a rapidly evolving area in the art, and methods of solid phase peptide synthesis are well-described in the following references, hereby entirely incorporated by reference: (Merrifield, B., *J. Amer. Chem. Soc.* 85:2149–2154 (1963); Merrifield, B., Science 232:341–347 (1986); Wade, J. D., et al., *Biopolymers* 25:S21–S37 (1986); Fields, G.B., *Int. J. Polypeptide Prot. Res.* 35:161 (1990); MilliGen Report Nos. 2 and 2a, Millipore Corporation, Bedford, Mass., 1987) Ausubel, et al, supra, and Sambrook, et al, supra.

In general, as is known in the art, such methods involve blocking or protecting reactive functional groups, such as free amino, carboxyl and thio groups. After polypeptide bond formation, the protective groups are removed (or de-protect-ed). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tboc method," the amino group of the amino acid being added to the resin-bound C-terminal amino acid is blocked with tert-butyloxycarbonyl chloride (tBoc). This protected amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoro-methanesulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the ∝-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethyl-formamide (DMF), and the final HF cleavage treatment is eliminated. A TFA solution is used instead to cleave side chain protecting groups and the peptide resin linkage simultaneously.

At least three different peptide-resin linkage agents can be used: substituted benzyl alcohol derivatives that can be cleaved with 95% TFA to produce a peptide acid, methanolic ammonia to produce a peptide amide, or 1% TFA to produce a protected peptide which can then be used in fragment condensation procedures, as described by Atherton, E., et al., *J. Chem. Soc. Perkin Trans.* 1:538–546 (1981) and Sheppard, R. C., et al., *Int. J. Polypeptide Prot. Res.* 20:451454 (1982). Furthermore, highly reactive Fmoc amino acids are available as pentafluorophenyl esters or dihydro-oxobenzotriazine esters derivatives, saving the step of activation used in the tboc method.

Pharmaceutical Methods and Preparations

The preferred animal subject of the present invention is a primate mammal. By the term "mammal" is meant an individual belonging to the class Mammalia, which, of course, includes humans. The invention is particularly useful in the treatment of human subjects, although it is intended for veterinary uses as well. By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hunaman monkeys of India); and superfamily Hominoidae, family Pongidae (including gibbons, orangutans, gorillas, and chimpanzees). The rhesus monkey is one member of the macaques.

The term "protection", as used herein, is intended to include "prevention," "suppression" and "treatment." "Prevention" involves administration of the protein prior to the induction of the disease. "Suppression" involves administration of the composition prior to the clinical appearance of the disease. "Treatment" involves administration of the protective composition after the appearance of the disease.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." It should also be understood that to be useful, the protection provided need not be absolute, provided that it is sufficient to carry clinical value. An agent which provides protection to a lesser degree than do competitive agents may still be of value if the other agents are ineffective for a particular individual, if it can be used in combination with other agents to enhance the level of protection, or if it is safer than competitive agents.

The composition may be administered parentally or orally, and, if parentally, either systemically or topically. Parenteral routes include subcutaneous, intravenous intradermal, intramuscular, intraperitoneal, intranasal, transdermal, or buccal routes. One or more such routes may be employed. Parenteral administration can be, e.g., by bolus injection or by gradual perfusion over time. Alternatively, or concurrently, administration may be by the oral route. The immunization is preferably accomplished initially by intramuscular injection followed by intradermal injection, although any combination of intradermal and intramuscular injections may be used.

It is understood that the suitable dosage of a immunogen of the present invention will be dependent upon the age, sex, health, and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This will typically involve adjustment of a standard dose, e.g., reduction of the dose if the patient has a low body weight.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow, et al., eds., *The Merck Manual,* 15th edition, Merck and Co., Rahway, N.J., 1987; Goodman, et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985), which references and references cited therein, are entirely, incorporated herein by reference.

The total dose required for each treatment may be administered in multiple doses (which may be the same or different) or in a single dose, according to an immunization schedule, which may be predetermined or ad hoc. The schedule is selected so as to be immunologically effective, i.e., so as to be sufficient to elicit an effective CTL response to the antigen and thereby, possibly in conjunction with other agents, to provide protection. The doses adequate to accomplish this are defined as "therapeutically effective doses." (Note that a schedule may be immunologically effective even though an individual dose, if administered by itself, would not be effective, and the meaning of "therapeutically effective dose" is best interpreted in the context of the immunization schedule.) Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

The doses may be given at any intervals which are effective. If the interval is too short, immunoparalysis or other adverse effects can occur. If the interval is too long, immunity may suffer. The optimum interval may be longer if the individual doses are larger. Typical intervals are 1 week, 2 weeks, 4 weeks (or one month), 6 weeks, 8 weeks (or two months) and one year. The appropriateness of administering additional doses, and of increasing or decreasing the interval, may be reevaluated on a continuing basis, in view of the patient's immunocompetence (e.g., the level of antibodies to melanoma-associated antigens).

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

In one embodiment, the immunogen is dissolved or suspended in an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The peptides of the invention may also be administered via liposomes, which serve to target the peptides to a particular tissue, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among melanocytes or melanomas, or with other therapeutic or immunogenic compositions. Thus, liposomes filled with a desired peptide of the invention can be directed to the site of target cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019369, incorporated herein by reference.

For targeting to the melanoma cells, a ligand to be incorporated into the liposome can include, e.g., antibodies or fragments thereof specific for cell surface determinants of the desired melanoma cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. the balance of the composition is ordinarily propellant. A carrier can also be included, as desired, as with, e.g., lecithin for intranasal delivery.

In addition to the peptides or analogues of the invention, a pharmaceutical composition may contain suitable pharmaceutically acceptable carriers, such as excipients, carriers and/or auxiliaries which facilitate processing of the active compounds into preparations which can be used pharmaceutically.

The appropriate dosage form will depend on the disease, the immunogen, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein. However, it is expected that each vaccine preparation will include 1–100 µg of the peptide epitope.

The composition may also include an adjuvant. Typical adjuvants include proteins, peptides, carbohydrates, lipids and liposaccharides. An example of a currently popular adjuvant is DETOX (Ribi Immunochemicals)(muramyl dipeptide and cell wall fragments from *Mycobacterium phlei*). Other adjuvants include QS-21, Montamide ISA-21, incomplete Freund's adjuvant, aluminum phosphate, aluminum hydroxide, alum, DEAE-dextran, saponin, and mineral oil. Montamide ISA-51 is manufactured by Seppic, Inc. (75 Quai D'Orsay, 75321, Paris, France). Its composition is manide oleate in mineral oil solution.

QS-21 is manufactured by Cambridge Biotech (365 Plantation Street, Worcester, Mass. 01605–2376). It is a triterpene glycoside isolated from the bark of a South American tree (Quillaja saponaria). The tradename for QS-21 is Stimulon™. Its molecular formula is $C_{92}O_{46}H_{148}$, and its molecular weight is 1,990. Its complete chemical name is 3-O-β-D-galactopyranosyl-(1->2)-[β-D-xylopyranosyl-(1->3)]-β-D-glucuronpyranosyl-quillaic acid 28-O-β-D-apiofuranosyl-(1->3)-β-D-xylopyranosyl-(1->4)-α-L-rhamnopyranosyl-(1->2)-3-[5-O-α-L-arabinofuranosyl 3,5-dihydroxy-6-methyloctanoyl]-3,5-dihydroxy-β-methyloctanoyl]-β-D-fucopyranoside.

If desired, the adjuvant may be conjugated to the epitope and not simply a part of a mixture. See Deres, et al, Nature, 342:561–4 (1989).

The composition may also include an immunomodulator, especially cytokines such as IL-1, IL-2, IL-4, IL-6, IL-7, IL-12, Interferon-alpha, Interferon-gamma, Granulocyte Macrophage Colony Stimulating Factor (GMCSF), Tumor Necrosis Factor (TNF)-alpha, and TNF-beta.

The composition may also include antigen-presenting cells, such as dendritic cells or macrophages. Preferably, the APCs are harvested, e.g., from peripheral blood or bone marrow, conjugated, covalently or noncovalently (e.g., by pulsing) to the immunogen, e.g., a peptide, and administered to the patient.

The composition may also include a molecule which activates or helps in activating CTLs, such as a CD-28 stimulatory molecule (e.g., B7.1, B7.2, or anti-CD28). If the molecule may be administered in place of the molecule itself.

CD80 (B7 BB1) is expressed on activated B cells and dendritic cells. It is a ligand for CD28 and CTLA-4. It has been found to represent two (partially homologous) proteins, B7–1 and B7–2. See Ramarathinam, et al. T cell costimulation by B7/BB1 induces CD8 T-cell-dependent tumor rejection: an important role of B7/BB1 in the induction, recruitment, and effector function of antitumor T cells. J.Exp. Med. 1994: 1790: 1205–1214; Freeman et al. Cloning of B7–2: a CTLA-4 counter-receptor that costimulates human T cell proliferation. Science 1993, 262: 909–911; Li et al. Costimulation of tumor-reactive CD4+ and CD8+ T lymphocytes by B7, a natural ligand for CD28, can be used to treat established mouse melanoma. J. Immunol. 1994, 153: 421–428; Hodge et al. Admixture of a recombinant vaccinia virus containing the gene for the costimulator molecule B7 and a recombinant vaccinia virus containing a tumor-associated antigen gene results in enhanced specific T-cell responses antitumor immunity. Cancer Res. 1995, 55: 3598–3603.

A pharmaceutical composition according to the present invention may further comprise at least one cancer chemotherapeutic compound, such as one selected from the group consisting of an anti-metabolite, a bleomycin peptide antibiotic, a podophyllin alkaloid, a Vinca alkaloid, an alkylating agent, an antibiotic, cisplatin, or a nitrosourea. A pharmaceutical composition according to the present invention may further or additionally comprise at least one viral chemotherapeutic compound selected from ganuna globulin, amantadine, guanidine, hydroxybenzimidazole, interferon-α, interferon-β, interferon-γ, thiosemicarbarzones, methisazone, rifampin, ribvirin, a pyrimidine analog, a purine analog, foscarnet, phosphonoacetic acid, acyclovir, dideoxynucleosides, or ganciclovir. See, e.g., Katzung; supra, and the references cited therein on pages 798–800 and 680–681, respectively, which references are herein entirely incorporated by reference.

As an alternative to a pharmaceutical composition comprising the immunogen of the present invention, per se, the pharmaceutical composition may instead comprise a vector comprising an expressible gene encoding such an immunogen. The pharmaceutical composition and method would then be chosen so that the vector was delivered to suitable cells of the subject, so that the gene would be expressed and the immunogen produced in such a manner as to elicit an immune response. A preferred vector would be a Vaccina virus, such as a construct containing a minigene encoding the peptide 96L: (SEQ ID NO:14) ((Try Ile Glu Pro Gly Pro Val Thr Val (SEQ. (SEQ ID No:98). A gene encoding the protein pMel-17 is also of some interest. In the case of genes encoding naturally occurring proteins, or peptide fragments thereof, one may, but need not, use the DNA sequence which encodes the proteins or peptides in nature. A preferred route for immunization would be scarification. A preferred immunization protocol would be 10E6 to 10E8 pfu/dose in the initial injection, followed up with boosters at 1,3 and 12 months. The boosters could be the previously described immunogen-containing composition.

In the case of genes encoding naturally occurring proteins, or peptide fragments thereof, one may, but need not, use the DNA sequence which encodes the proteins or peptides in nature.

Recombinant vaccinia virus constructs have been used for immunization against hepatitis B (Moss, et al., *Nature,* 311, 67, 1984), herpes simplex virus (Wacchsman, et al., *Biosci. Rep.* 8, 323; 334, 1988), parainfluenza type 3 (Spriggs, et al., *J. Virol.,* 62, 1293, 1988), and Lassa fever virus (Fisher-Hoch, et al., *Proc. Natl. Acad. Sci. USA,* 86, 317, 1989). Vaccinia virus constructs comprising gene for cancer-associated antigens have also been prepared (Lathe, et al., *Nature,* 326, 878, 1987; Bernards, et al., *Proc. Natl. Acad. Sci. USA,* 84, 6854, 1987; Estin, et al., *Proc. Natl. Acad. Sci. USA,* 85, 1052, 1988).

Alternatively or additionally, the composition may comprise melanoma-specific CTL. Antigenic peptides may be used to elicit CTL ex vivo. Ex vivo CTL responses to a melanoma antigen are induced by incubating in tissue culture the patient's CTL precursor cells ($CTL_p$) together with a source of antigen-presenting cells (APC) and the appropriate immunogenic peptide. After an appropriate incubation time (typically 1–8 weeks), in which the $CTL_p$ are activated and mature and expand into effector CTL, the cells are infused back into the patient, where they will destroy their specific target cell. In order to optimize the in vitro conditions for the generation of specific cytotoxic T cells, the culture of stimulator cells may be maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 200 or more, human Class I MHC molecules loaded with peptide to be expressed on the surface of each stimulator cell. Preferably, the stimulator cells are incubated with at least 1 mg/ml, more preferably >20 μg/ml peptide.

Resting or precursor CD8+ cells are then incubated in culture with the appropriate stimulator cells for a time period sufficient to activate the CD8+ cells.

Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 1:5 to 20:1, more preferably 3:1 to 5:1. The effector/stimulator culture may be maintained for as long a time as is necessary to stimulate a therapeutically useful or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Often it is useful, in the generation of peptide-specific CTL, to stimulate with mutant cell lines that have some empty MHC molecules. An exmample is the human lymphoid cell line, T2. However, mutant cell lines expressing every MHC molecule are not yet available. Thus, in some cases, it may be useful to strip endogenous MHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8–10 residues, 2) a transmembrane heavy polymorphic protein chain which bears the peptide-binding site in its α1 and α2 domains, and 3) a non-covalently associated non-polymorphic light chain, $β_2$ microglobulin. Removing the bound peptides and/or dissociating the α2 microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include the culture temperature from 37° C. to 26° C. overnight to destabilize $β_2$ microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^{6-5\times10^7}$ cells are used in mice.

Preferably, as discussed above, the activated CD8+ cells are harvested from the cell culture prior to administration of the CD8+ cells to the individual being treated. It is important to note, however, that unlike other present and proposed treatment modalities, the present method preferably uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

Adoptive transfer of melanoma-specific CTL has been accompanied by tumor shrinkage in a large minority of patients with advanced melanoma and by disappearance of all detectable tumor in a smaller proportion of patients. (Rosenberg et al, NEM 319: 1676–1680, 1988) and in animal studies appears to be particularly promising for the treatment of solid tumors (Rosenberg S A et al. Science 233:1318–1321). One of the problems with existing methods for CTL generation is that they require the resection of large metastic tumor deposits to initiate the process. If the requirement for available autologous tumor could be circumvented, then patients with no measurable disease but a high risk of recurrence (eg, melanoma patients with primary tumors greater than 4 mm thick or with microscopic tumor metastatic to regional nodes) could be treated with adoptive therapy even if their tumor were removed and fixed in formalin and no other gross tumor was evident. These patients have a very high likelihood of harboring micrometastic disease for which no other effective therapy is now available; so most will die of the melanoma. It is possible that the presence of bulky tumor suppresses the autologous immune response; so treatment of patients without bulky disease would be an attractive goal. Especially in murine systems, CTL have been generated and maintained by stimulation with cells to which the peptide epitope has been bound. We propose that, e.g., HLA-A2.1+ or HLA-A3+cells (autologous B cells, macrophages, or dendritic cells, ideally), would be pulsed in vitro with peptide (e.g., peptide 946, Tyr Xaa Glu Pro Gly Pro Val Thr Ala (SEQ ID NO:123) and used as in vitro simulators for autologous lymph node cells or peripheral blood lymphocytes. The patients could be pre-stimulated with a peptide vaccine prior lymphocyte harvest if the existing response was inadequate. Lymphocytes stimulated with peptide in vitro could then be expanded to $10^{10}$ or $10^{11}$ cells, then re-infused into the patients in a manner analogous to that used for LAK cell therapy. It is expected that the adoptively transferred CTL would survive best with IL-2 infusion at low to intermediate doses, and that putative inhibitors of Tc suppression (eg: cyclophosphamide) may be employed also, prior to the infusions of CTL.

Clinical studies with adoptive immunotherapy using A2-restricted tumor infiltrating lymphocytes (TIL) have shown a strong correlation between Pmel-17/gp100 reactivity and positive clinical responses of patients treated with those TIL. Kawakami, et al., J. Immunol., 154:3961–8 (1995).

Melanoma-Specific Diagnostic Agents

A melanoma-specific diagnostic agent is (1) a molecule which is or which comprises a melanoma-specific epitope as previously defined, and which is labeled, immobilized, or otherwise rendered suitable for diagnostic use, or (2) an antibody which specifically binds such a melanoma-specific epitope, and which is labeled, immobilized, or otherwise rendered suitable for diagnostic use, or (3) a T-cell line (e.g., murine or human), which specifically recognizes a melanoma-specific epitope.

Diagnostic Uses and Compositions

The relationship between the host's immune response and his or her tumor is poorly understood. Better understanding of that response depends on evaluation of the specific responses against individual epitopes, such as the 946 peptide. If patients do have an immune response to 946 naturally, then evaluation and quantitation of that by precursor frequency analysis of the CTL in the patient's blood pool may permit some assessment of the protection that person's immune system is providing. As new therapies become available for melanoma, it may be useful to screen patients for the presence of the 946 peptide on their tumor and the presence of CTL in their blood pool with specificity for the 946 peptide on HLA-A2. In like manner one may screen for (SEQ ID NO:98) peptides on the tumor and for anti-(SEQ ID NO:98) CTLs in the blood of A3+patients. These findings may determine whether further augmentation of the immune response is indicated or whether other, non-immunologic, therapy should be employed. A parallel to this is the determination on breast cancers of the presence of estrogen and progesterone receptors before considering hormonal therapy or chemotherapy.

Thus, the peptides of the present invention may be used to screen a sample for the presence of an antigen with the same epitope, or with a different but cross-reactive epitope, or for the presence of CTLs which specifically recognize the corresponding epitopes. The sample will normally be a biological fluid, such as blood, urine, lymphatic fluid, amniotic fluid, semen, saliva, tears, milk, or cerebrospinal fluid, or a fraction or derivative thereof, or a biological tissue, in the form of, e.g., a tissue section or homogenate. The preferred sample is blood, or a fraction or derivative thereof.

Assays may be divided into two basic types, heterogeneous and homogeneous.

In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

Assays may also be divided into competitive and non-competitive formats. In the competitive format, the analyte competes with a labeled analyte analogue for binding to a binding partner. In a common noncompetitive format called a sandwich assay, the analyte is first bound by a capture reagent, and then by a tag reagent.

In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically. The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^{3}$H, $^{125}$I, $^{131}$I, $^{35}$S, $^{14}$C, and, preferably, $^{125}$I.

It is also possible to label a compound with a fluorescent compound. When the fluorescently labeled anti-body is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be attached to the binding protein using such metal chelating groups as diethyl-enetriaminepentaacetic acid (DTPA) and ethylene-diamine-tetraacetic acid (EDTA).

The peptides also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bio-luminescent compounds for purposes of labeling are luciferin, luciferase and aequorin.

Enzyme labels, such as horseradish peroxidase, alkaline phosphatase, malate dehydrogenase, staphylococcal nuclease, δ-V-steroid isomerase, yeast alcohol dehydrogenase, α-glycero phosphate dehydrogenase, triose phosphate isomerase, asparaginase, glucose oxidase, β-galactosidase, ribonuclease, glucose-6-phosphate dehydrogenase, glucoamylase and acetyl-choline esterase, are preferred. When an enzyme label is used, the signal producing system must also include a substrate for the enzyme. If the enzymatic reaction product is not itself detectable, the SPS will include one or more additional reactants so that a detectable product appears.

A label may be conjugated, directly or indirectly (e.g., through a labeled antibody), covalently (e.g., with SPDP) or noncovalently, to the peptide, to produce a diagnostic reagent. Similarly, the peptide may be conjugated to a solid phase support to form a solid phase ("capture") diagnostic reagent. Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Additionally, the peptides may be used as a diagnostic tool to evaluate whether other immunotherapeutic treatments (tumor vaccines of any kind, adoptive transfer of CTL, etc) are having a beneficial effect.

Figure 11:
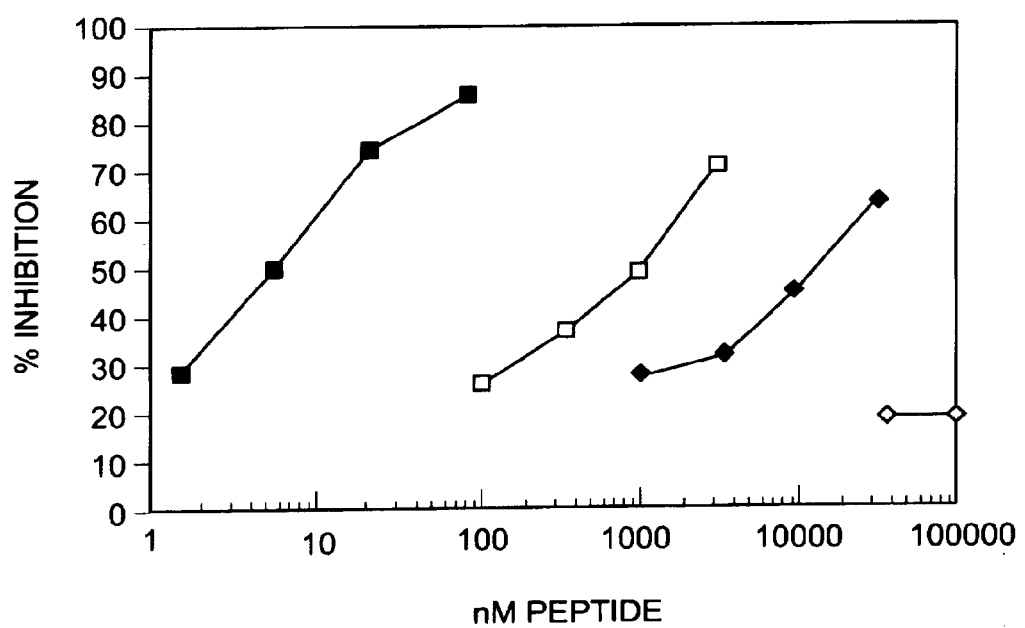
FIG. 11 illustrates the binding of synthetic 946 peptides to HLA-A2.1.

Also the peptides 946L (SEQ ID NO:14) and 946I (SEQ ID NO:39) have low to intermediate affinity for the HLA-A2.1 molecule. This is illustrated in FIG. 11. For this reason, they will be useful as control peptides for the evaluation of candidate peptide/MHC binding affinity. Because they represent a low affinity range, they can be used in laboratory studies on binding affinity of other peptides. This methodology, in a preferred embodiment, would likely include: binding the peptide to T2 cells, then evaluating lysis of the T2 cells by any of various standard methods, such as a proliferative response of the CTL, or cytokine release by the CTL exposed to the T2 cells+peptide.

EXAMPLES

Materials and Methods—Cell Lines and HLA Typing

All tumor cell lines were of human origin. Melanoma cell lines HT144 and Sk-MeI-24, osteosarcoma 143b, colon cancer CCL-228 (SW480), and breast cancer MDA-MB-468 were obtained from the American Type Culture Collection (Bethesda, Md.). Fibroblasts GM126 were obtained from the National Institute of General Medical Sciences Human Genetic Mutant Cell Repository, Bethesa, Md. Melanoma lines DM6, DM13, DM14, and DM93 were the gift of Drs. Hilliard F. Siegler and Timothy L. Darrow. VMM1 and VMM5 are melanoma cell lines established from metastatic melanoma resected from patients at the University of Virginia (Charlottesville, Va.). VBT2 (squamous cell lung carcinoma), VA01 (adenocarcinoma of the ovary), and VAB5 (adenocarcinoma of the breast) are cell lines also established at this institution. JY, MICH, MWF, 23.1, RPMI 1788, and Herluff are EBV-transformed B lympho-blastoid lines. K562 is a NK-sensitive human erythroleukemia line. The cell line T2 is derived from the fusion of a T cell line, CEM, and a human B cell mutant, LCL 721.174. This cell line expresses HLA-A2.1 molecules but has an Ag-processing defect that is associated with enhanced presenta-tion of exogenous peptides.

HLA types of the specimens used in this study (Examples I–VIII) are summarized in Table 1.

Expression of HLA-A2 on tumor cells was assessed by staining with BB7.2. Expression of the A2 subtype HLA-A2.1 was confirmed by susceptibility to lysis by HLA-A2.1-specific murine CTL clones AT1-15 and AX21-9, and by staining with HLA-A2.1/A2.2-specific mAb CR11.351.

Generation of Tumor-Specific Cytotoxic T Cells

Detailed methods of CTL generation have been previously reported. Malignant melanoma metastatic to cervical lymph nodes was resected from an 80-yr old patient designated VMM5. The nodes were mechanically dissociated and then enzymatically digested in Eagle's MEM (GIBCO, Grand Island, N.Y.) containing 2.5% FCS (GIBCO, or Whittaker, Walkersville, Md.), 0.1% collagenase B (Boehringer-Mannheim, Indianapolis, Ind.), 0.002% DNase (Sigma, St. Louis, Mo.), penicillin 100 U/ml, streptomycin 100 microg/ml (Pen-Strept, GIBCO) at room temperature. After 4 h, dissociated cells were collected and cryopreserved. Remaining tumor fragments were returned to the digestion media overnight. The digests were harvested in a similar fashion daily for 3 days, with viable tumor cells and lymphocytes obtained each day. These cells were cryopreserved in FCS+10% DMSO in liquid nitrogen. Initial cultures were established with the mixture of lymphocytes and tumor from the tumor-involved node. The ratio of tumor cells to lymphocytes placed in culture were approximately 1:1. The cells were cultured in 24-well tissue culture plates (Linbro, Hamden, Conn.) in RPMI 1640 (Sigma) containing 10% FCS, Pen-Strept, and 20 U/ml rIL-2 (Cetus, Emeryville, Calif.). The CTL were restimulated with irradiated (100 Gy) fresh cryo-preserved autologous tumor (VMM5) at a TLR (tumor: lymphocyte ratio) of 1:10 on day 16. Beginning with the third in vitro stimulation (day 32), and thereafter every 10 to 15 days, the CTL were restimulated with the allogeneic HLA-A2.1+melanoma cell line DM6. A TLR of 1:5 was used until the cells were 70 days

TABLE 1

Human cell lines used in this study: HLA types and susceptibility to lysis by VMM5 CTL[1a]

| Cell Line (Ref.) | Cell Type[b] | HLA-A | HLA-B | HLA-C | HLA-DR | HLA-DQ | Lysis by VMM5 CTL[a] |
|---|---|---|---|---|---|---|---|
| DM6 (11) | Melanoma | 2.1[c] | 12, 13 or 35 | 1, 2 | 6.10.(7)[d] | —[e] | ++ |
| DM13 (11) | Melanoma | 2.1, 31 | 13, 18 | ND | ND | ND | +++ |
| DM14 (11) | Melanoma | 11, 28 | 5, 8 | 2, 4 | — | — | -- |
| DM93 (11) | Melanoma | 2.1, 33 | 8, 49, w6 | ND | 2, 4, 6[d] | 3 | ++ |
| SkMe124 (26) | Melanoma | 1, 2.1 | 12, 14 | — | — | — | -- |
| HT144 (26) | Melanoma | 1, 24 | 13, 15 | 3 | 4, 7 | — | -- |
| HT144 A2--03 | Melanoma | 1, 2.1, 24 | 13, 15 | 3 | 4, 7 | — | + |
| VMM1 | Melanoma | 3, 26 | 51, w4, w6 | ND | — | — | -- |
| VMM5 | Melanoma | 2.1 | 39 | ND | 7, 11, 52, 53 | 2, 7 | +++ |
| VBT2 | Lung CA | 34, 68 | 35, (53?) | 4? | — | — | -- |
| VAO1 | Ovarian CA | 2 | — | — | — | — | -- |
| VAB5 | Breast CA | 2, 25 | 60, 62 | 3 | — | — | -- |
| MDAMB468 (26) | Breast CA | 23, 30 | 27, 35 | 2, 4 | — | — | -- |
| CCL228 (26) | Colon CA | 2.1 | 8, 17 | — | — | — | -- |
| 143b (29) | Osteosarcoma | 2.1 | — | — | — | — | -- |
| GM126 (29) | Fibroblasts | 2.1 | — | — | — | — | -- |
| K562 | Erythroleukemia | — | — | — | — | — | -- |
| MICH (28) | EBV-β[g] | 2.1, 32 | 15, 27 | — | 5, 5 | — | -- |
| RPMI-1788 (26) | EBV-β | 2.1, 33 | 7, 14 | — | — | — | -- |
| JY (28) | EBV-β | 2.1, 2.1 | 7, 7 | — | 4, 6 | — | -- |
| Herluff (27) | EBV-β | 2.1, 2.1 | 12, 35 | — | — | — | -- |
| 23.1 (28) | EBV-β | 2, 2 | 27, 27 | — | 8, 8 | — | -- | old, after which a TLR between 1:2 and 2:1 was used. Several VMM5 CTL lines were generated following this protocol closely and with consistent results from each. Similar methods were enployed for generation of other CTL lines studied.

Cytotoxicity Assays

Cell-mediated killing was determined in vitro using a 4-h chromium release assay. 51Cr-labeled target cells were plated at $2\times10^3$ cells/well in triplicate on 96-well V-bottom plates (Costar, Cambridge, Mass.) with varying numbers of effector cells in a final volume of 250 microl. Wells containing either culture medium and target cells only or 1 M HCl and target cells served as background 51Cr release controls and total release controls, respectively. The plates were centrifuged at 100×g for 3 min and incubated at 37° C. in 5% CO2 for 4 h. The plates were again centrifuged, and 0.20 ml of medium from each well was removed for counting in a gamma counter. The cytotoxic index was calculated as:

$Cpm$(experimental)–$cpm$(background)×100% $Cpm$ (total release)–$cpm$(background)

Lytic units were calculated for several of the cytotoxicity assays, using a software package prepared by the National. Cancer Institute (Bethesda, Md.), which solves for the equation $y=A\times[1-\exp(-kx)]$, where x is the E:T ratio, y is the cytotoxic index, A is the curve maximum, and k is a constant used to calculate the slope of the best fit line. For the purposes of this study, a lytic unit was defined as the number of effector cells needed to mediate 30' lysis of target cells. The number of lytic units was calculated per $10^5$ effector cells (LU30 per $10^5$ cells).

Example I

Extraction of HLA-A2.1-Associated Peptides from Melanoma Cells

The human melanoma cells DM6 and DM93 were cultured in 10-chamber cell factories (Nunc, Thousand Oaks, Calif.) in MEM supplemented with 1% FCS and Pen-Strept. In initial experiments, the cells were harvested with 0.03% EDTA in PBS, whereas in later experiments 0.025% trypsin was also included. Trypsinization resulted in more complete harvests and in higher cell viability without any evident change in reconstitution of epitopes or in the peptide profile (data not shown). Peptides bound to the A2 molecules were acid eluted and isolated by centrifuge filtration using a modification of the protocol described by Hunt et al. Cells were washed three times in cold PBS and solubilized in 20 ml, per $10^9$ cells, of 1% NP-40, 0.25% sodium deoxycholate, 174 microg/ml PMSF, 5 microg/ml aprotinin, 10 microg/ml leupeptin, 16 microg/ml pepstatin A, 33 microg/ml iodoacetamide, 0.2% sodium azide, and 0.03 microg/ml EDTA. The mixture was incubated at 4° C. for 1 h, then centrifuged for 1 h at 100,000×g at 4° C. The supernatant was passed through a 0.22-microm filter, then was passed slowly over two protein A-Sepharose (Sigma) columns in series. The first contained GAP-A3 antibody, specific for HLA-A3, as a negative control, whereas the second column contained BB7.2, specific for HLA-A2. The columns were separately washed and eluted with 0.2N acetic acid, pH 2.7. The HLA molecules and peptides were dissociated at pH 2.1 by bringing the solution to 10% acetic acid and boiling 5 min. Peptides were separated from masses of >5 kDa (antibody, class I H chain, beta-2 microglobulin) by centrifugation through an Ultrafree-CL filter (5000 NMWL, Millipore, Bedford, Mass.). Yields of the peptide were estimated from the quantitation of HLA-A2.1H chain obtained, using SDS-PAGE. The average estimated yield of HLA-A2.1 molecules was 125 microg per $5\times10^9$ cells. The quantity of peptide eluted from 1 microg of HLA-A2.1 will hereafter be referred to as 1 U of peptide.

Example II

HPLC Fractionation of Peptide Extracts

The peptide extracts were fractionated by reversed phase high performance liquid chromatography (HPLC) on an Applied Biosystems model 130A (Foster City, Calif.) separation system. Peptide extracts were concentrated to 100 microl on a Speed Vac, injected onto a Brownlee narrow-bore C-18 Aquapore column (2.1 mm×3 cm, A, 7 microm) and eluted with a 40-min gradient of 0 to 60% (v/v) acetonitrile/0.085% trifluoracetic acid (TFA) in 0.1% TFA. Fractions were collected at 1-min intervals. Cytotoxicity assays were performed to identify fractions that reconstituted CTL epitopes. For some experiments, reconstituting fractions were divided into two equal parts. The first was injected onto a Brownlee narrow-bore C-18 Aqua-pore column (2.1 mm×3 cm, 300 A, 7 microm) and eluted with a 40-min gradient of 0 to 60% (v/v) acetonitrile in 0.1% HFA that had been adjusted to pH 8.1 with 14.8 M ammonium hydroxide. The second half was injected onto the same type of column and eluted with a 40-min gradient of 0 to 0.60% (v/v) acetonitrile/0.1% heptafluorobutyric acid (HFBA) in 0.1% HFBA. Fractions for both second dimension separation methods were collected at 1-min intervals. Cytotoxicity assays were again performed to identify fractions that reconstitute CTL epitopes.

Example III

Reconstitution Experiments

Soluble peptide fractions were partially dehydrated on a Speed Vac, reconstituted in assay media (RPMI 1640, 10% FCS, antibiotics), then incubated for 2 h with $2\times10^3$ 51Cr-labeled T2 cells in 150 microl/well in 96-well plates. Effector cells were added in 100 microl assay medium to give an E:T ratio of 10:1, and were incubated at 37° C. The remainder of the assay is performed as in standard chromium release assays described above. Wells containing peptide and target cells but no CTL were used as controls to rule out toxicity of the peptides themselves. Except with very acidic fractions 1 to 3, no cytotoxicity was observed with peptide alone; after the first two assays, the pH in these early fractions was adjusted to pH 7 using 1 M NaOH.

Example IV

Generation of Melanoma-Specific A2.1-Restricted Human CTL

Lymphocytes and melanoma cells harvested from tumor-involved lymph nodes of a patient with metastatic melanoma (VMM5) were cocultured in the presence of rIL-2 and were restimulated biweekly, first with autologous and then with allogenic HLA-A2.1$^+$ melanoma. In FIG. 1, the specificity of VMM5 CTL is shown. The CTL were generated as described heretofore in Materials and Methods. Cytotoxic activity was evaluated in a 4-h chromium release assay on the HLA-A2+ melanomas DM6 (solid squares) and DM93 (solid circles), the HLA-A2-melanomas DM14 (open squares) and HT144 (open circles), K562 (solid triangles) and T2 (triangles). Specific lysis of the HLA-A2.1+melanomas DM6 and DM93 was observed by day 39 of culture, whereas the HLA-A2 negative melanomas DM14 and HT144, the NK target K562, and the HLA-A2.1+ lymphoblastoid Ag-processing-mutant T2 were lysed minimally. This specificity was maintained for at least 4 mo. in culture, during which time the minimal lysis of K562 and T2 diminished further. In assays against a panel of 13 targets, the specific lysis of HLA-A2.1+melanomas was confirmed, whereas HLA-A2-melanomas and A2+tumors of other cell types were not lysed. In FIG. 2A, melanoma-specific CTL line VMM5 was assayed in a 4-h chromium release assay on day 94 of culture. In FIG. 2B, the murine CTL clone AX21-9, specific for HLA-A2.1 molecules, was assayed. In both panels, an E:T ratio of 10:1 is represented. The name of the-HLA-A2.1 transfectant of HT144 is abbreviated as HT/A2.3. Murine CTL clone AX21-9, which is specific for HLA-A2 expressed on a variety of cell types, did lyse all of the A2+targets well. These results verify that failure of VMM5 CTL to lyse the A2+nonmelanomas is not caused by inherent resistance of the targets to CTL lysis. In separate experiments, lysis of additional HLA-A2+ nonmelanomas was minimal as set forth in TABLE I. As illustrated in TABLE II, the CTL lysed both fresh and cultured autologous tumor, but failed to lyse autologous PHA blasts or autologous LPS blasts.

TABLE II

Lysis of autologous targets by VMM5 CTL and murine HLA-A2-specific CTL
%

| Effector Cell | Target Cell | Specific Cr-51 Release |
|---|---|---|
| VMM5 | CTLFresh VMM5 melanoma | 79 |
| | Cultured VMM5 melanoma | 75 |
| | VMM5 PHA blasts | -1 |
| | VMM5 LPS blasts | -3 |
| AT 1-15 | CTLFresh VMM145 melanoma | 62 |
| | Cultured VMM5 melanoma | 22 |
| | VMM5 PHA blasts | 21 |
| | VMM5 LPS blasts | 20 |

Lysis of the blasts by AT1-15 clones in one experiment is shown in the above table. In additional experiments, lysis of PHA blasts by AX21-9CTL and AT-15 CTL was 80% and 25%, respectively, at an E:T ratio of 20:1, whereas lysis by the VMM5 CTL was 1%. One HLA-A2+ melanoma, SkMel24, was not lysed by VMM5 CTL. The HLA-A2 negative melanoma HT144 was transfected with the A2.1 gene: the resulting transfectant, HT144 A2.03, expressed HLA-A2.1 and was susceptible to lysis by VMM5 CTL, whereas the parent line was not lysed. Thus, VMM5 CTL are a population of melanoma-specific human CTL, restricted by HLA-A2.1 molecules, that resemble other class I-MHC-restricted, human melanoma-specific CTL lines reported in the literature in that they lyse the majority of HLA-A2.1+ melanomas but fail to lyse autologous nonmelanoma cells, HLA-A2+ nonmelanomas, or HLA-A2-melanomas. Similar specifity for HLA-A2+ melanomas has been observed with the other CTL lines studied.

Example V

Identification of Peptide Fractions that Reconstitute Melanoma-Specific Epitopes T2 cells were employed in the present invention to test reconstitution of melanoma-specific epitopes by soluble exogenous melanoma-derived peptides. These cells as well as other cells expressing appropriate HLA molecules and with or without an enhanced presentation of exogenous peptides may be used as functionally equivalent in the context of the invention. In particular, these cells may be used for stimulating lymphocytes in vitro for the purpose of activating CTL for the subsequent administration to a melanoma patient.

Peptides were acid-eluted from affinity-purified HLA-A2.1 molecules isolated from detergent solubilized human melanoma cells. As graphed in FIG. 3, extracts eluted from A2.1 specific (circles) or negative control immunoaffinity columns (squares) were added to $2 \times 10^3$ 51Cr-labeled T2 cells. The solid symbols represent extracts plus CTL and the open symbols represent extracts alone. One unit of peptide equals that amount of peptide derived from 1 microg of HLA-A2.1 molecules. The dose of negative control extracts is based on cell equivalents, matched to the A2.1 peptide extracts. Lysis of DM93 cells (positive control) was 68%. Unfractionated peptide extract from DM93 cells did reconstitute melanoma-specific epitopes on T2 cells. Maximal lysis of 37% was achieved with 1 U of peptide. Reconstitution of CTL epitopes with unfractionated peptides, but not with negative control extracts, verified the presence in the extract of one or more peptides that reconstitute melanoma-specific epitopes.

Figure 4A:
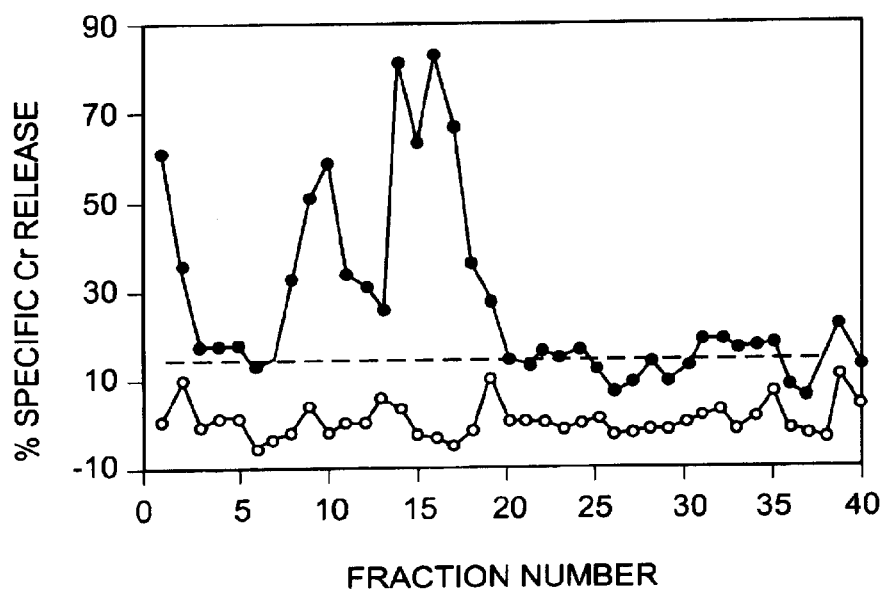
FIG. 4 is a graph of the reconstitution of melanoma-specific epitopes using reversed phase HPLC fractionated peptide extracted from HLA-A2.1 molecules expressed on DM6 cells (FIG. 4A) or lymphoblastoid cells JY (FIG. 4B)
Figure 4B:
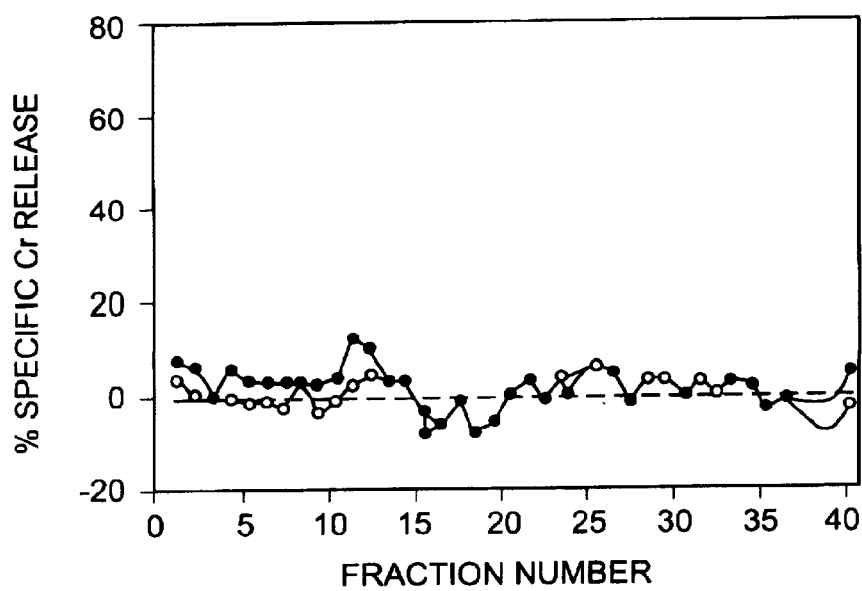
Figure 5A:
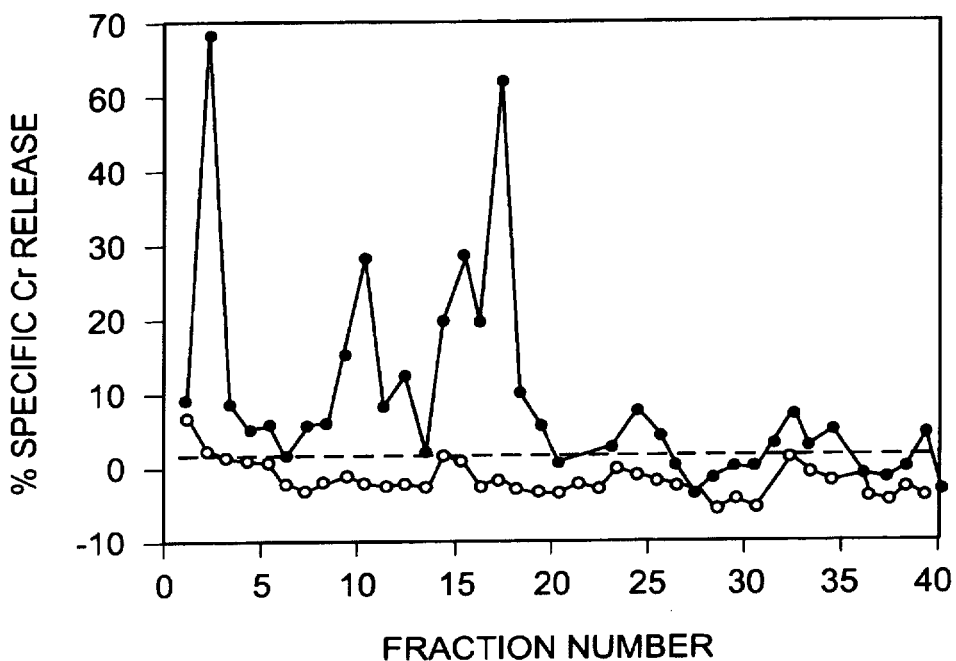
FIG. 5 illustrates in a graph the reconstitution of melanoma-specific epitopes using reversed phase HPLC-fractionated peptide extracted from HLA-A2.1 molecules expressed on DM93 cells (FIG. 4A) or lymphoblastoid cells JY (FIG. 4B)
Figure 5B:
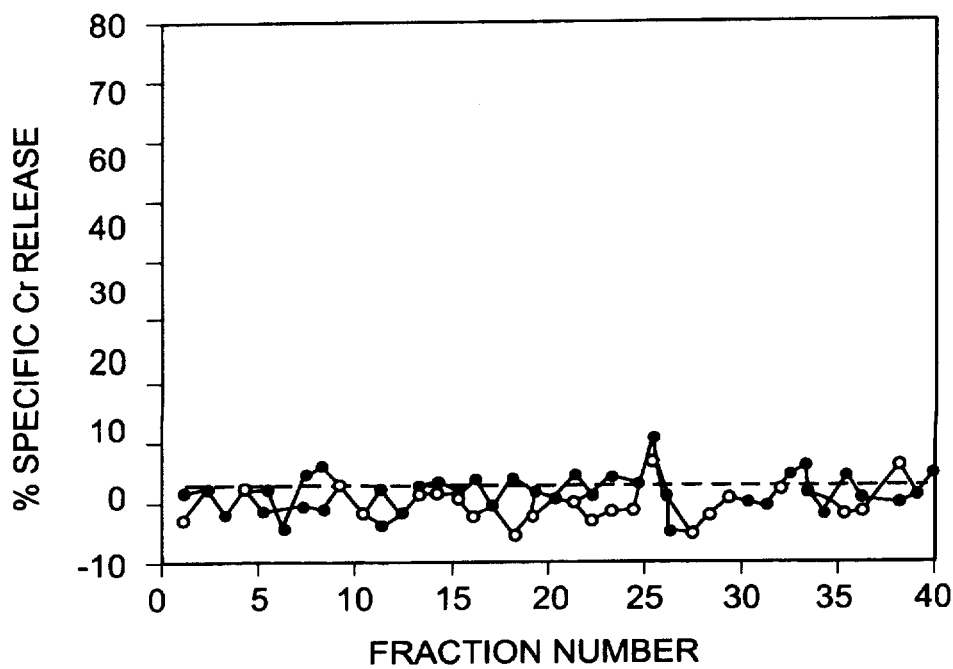
Figure 7A:
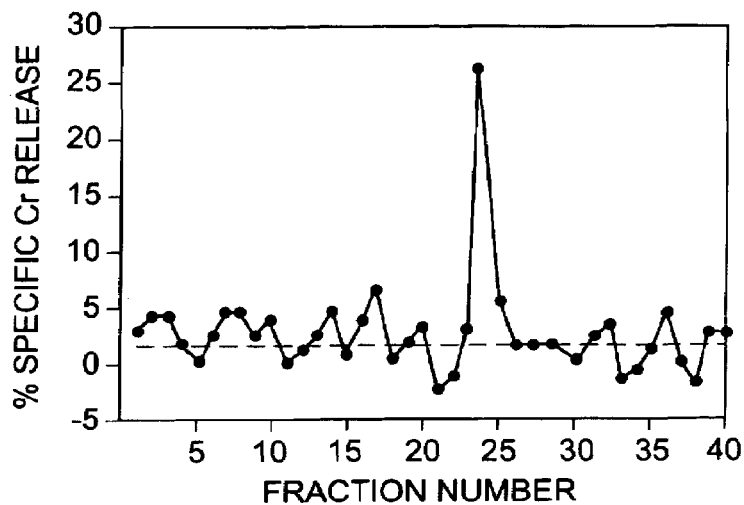
FIG. 7 graphs the second dimension separations of peptide extracts (FIGS. 7A–7D show separation of peaks A–D from DM93.
FIG. 7E, of peak D peptides from DM6)
Figure 7B:
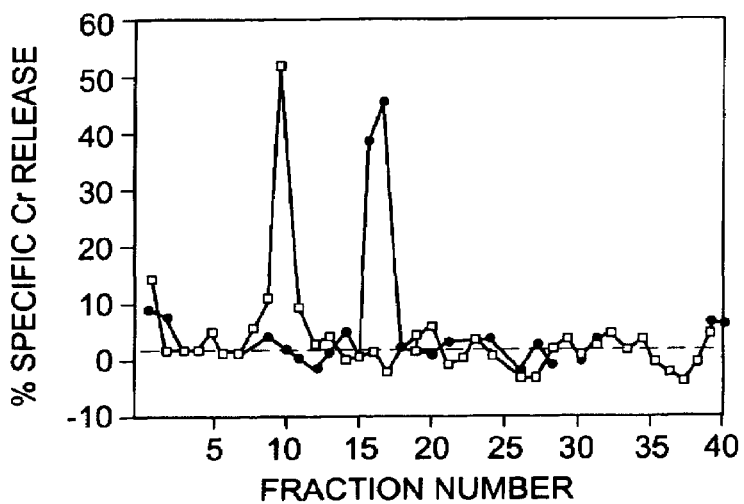
Figure 7C:
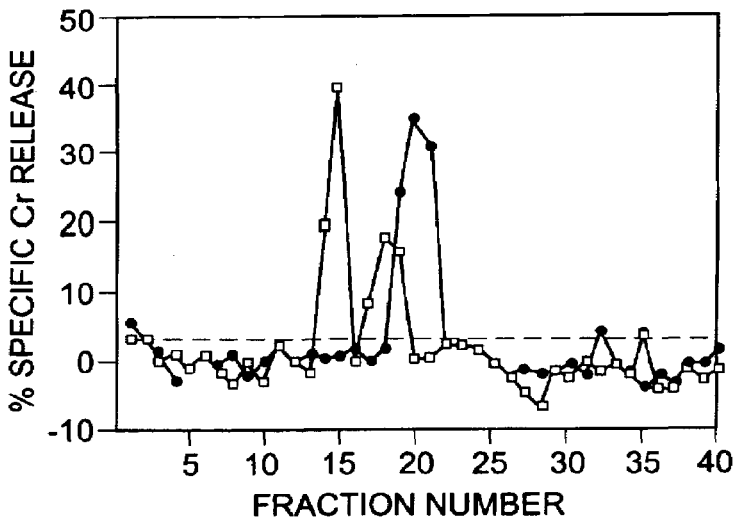
Figure 7D:
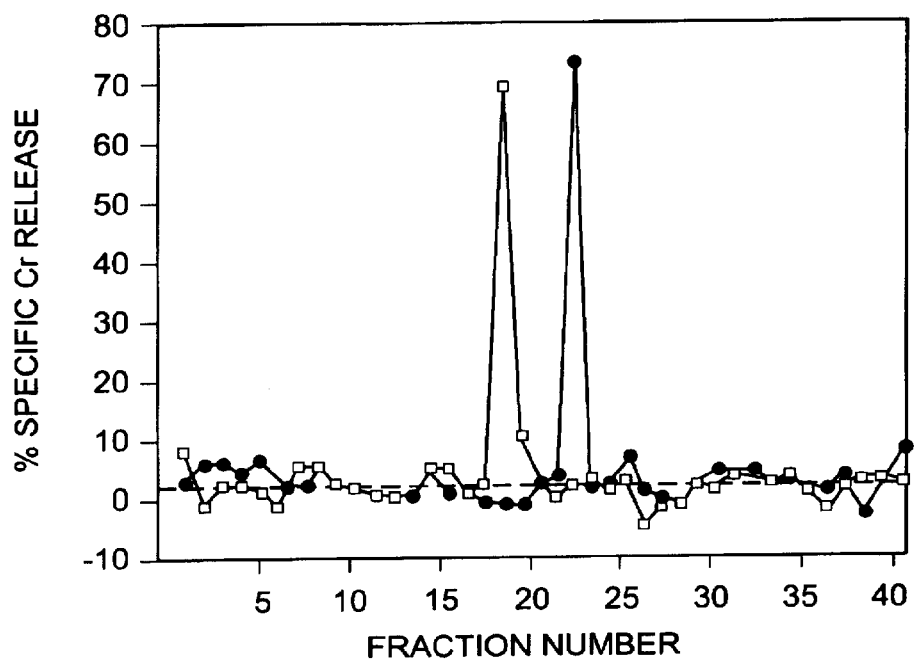
Figure 7E:
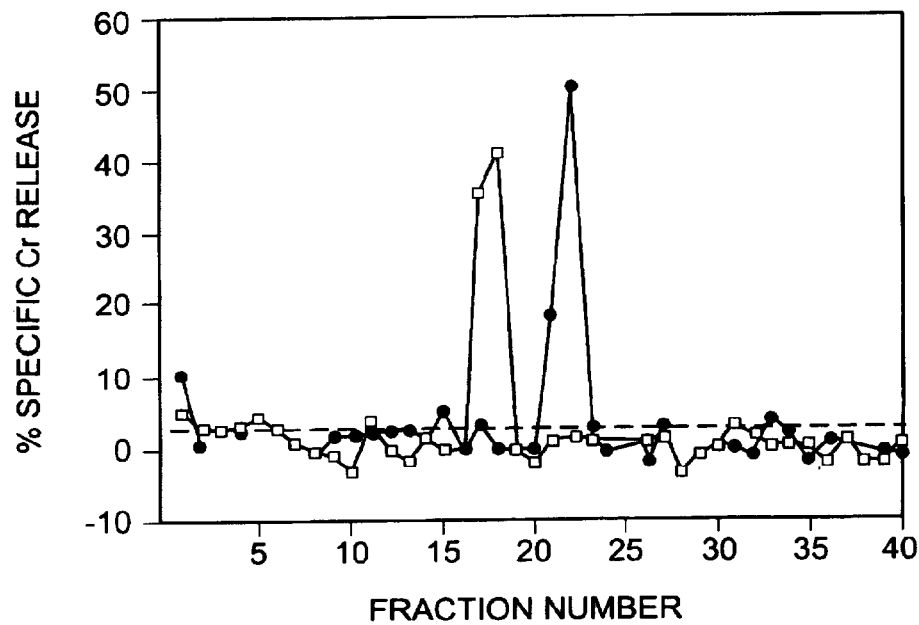

To define further the components responsible for reconstituting CTL epitopes, the mixture of peptides extracted from the A2.1 molecules on DM6 cells was fractionated by reversed phase HPLC, and individual fractions were added to T2 cells, as shown in FIG. 4. Individual HPLC fractions were added to $2 \times 10^3$ 51Cr-labeled T2 cells and then incubated in the presence (solid circles) or absence (open circles) of melanoma-specific CTL. FIG. 4A illustrates peptides extracted from DM6 cells; FIG. 4B, peptides extracted from lymphoblastoid cells JY; background lyse of T2 cells without peptide is plotted as a horizontal dotted line. Lysis of DM93 cells was 65% in A and 31% in B. Four prominent peaks of reconstitution, A, B, C, and D, located at fractions 1, 10, 14, and 16, respectively are shown in FIG. 4A. A fifth, smaller, peak B1 at fraction 12 was also observed. The specificity of reconstitution with these fractions from DM6 melanoma cells was established by the inability to reconstitute CTL epitopes using HPLC-fractionated peptide extracts from the A2.1 molecules expressed on the EBV-transformed lymphoblastosis cell line, JY shown in FIG. 4B. This pattern of reconstitution observed with DM6-derived peptides was compared to that of another HLA-A2.1+ melanoma cell line, DM93, which had not been used to restimulate these CTL is illustrated in FIG. 5. DM93-derived peptides of FIG. 5A produced the same pattern of multiple peaks of reconstitution that was observed as with DM6 of FIG. 4A. Individual HPLC fractions were added to $2 \times 10^3$ 51Cr-labeled T2 cells and then incubated in the presence (closed circles) or absence (open circles) of melanoma-specific CTL. A, peptides extracted from an A2.1 specific immunoaffinity column; B, peptides extracted from a negative control immunoaffinity column. Background lysis of T2 is plotted as a horizontal dotted line. Lysis of DM93 cells was 68% in A and 45% in B. From left to right peaks A, B, B1, C, and D are observed in FIG. 5A. The specificity of reconstitution with the A2 extract from DM93 was confirmed by the inability to reconstitute CTL epitopes with HPLC fractions of the negative control extracts, using doses comparable with those used for reconstitution with A2.1-associated peptides from the melanoma cells, as illustrated in FIG. 5B.

Figure 6:
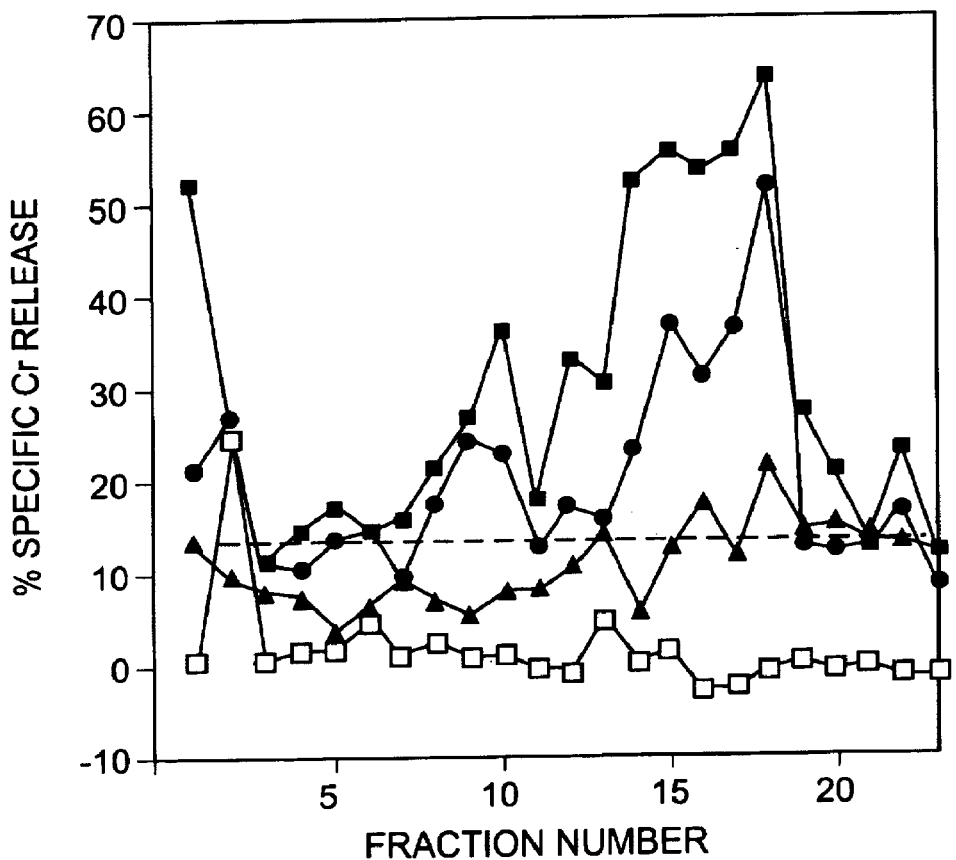
FIG. 6 illustrates graphically the titration of peptide dose for reconstitution.

Peptide fractions were used to evaluate reconstitution of CTL epitopes as described in Materials and Methods and illustrated in the graph of FIG. 6. The doses of peptide used were eight (solid squares), 1.25 (solid circles), and 0.25 (solid triangles) units per well. Background lysis of T2 is plotted as a horizontal dotted line. Cells were also incubated with 8 U of peptide without CTL (open squares). Reconstitution for each peak was dose dependent within the range 0.25 to 8 U/well. The pattern of five peaks of reconstitution was observed in six different experiments with five different peptide extracts, using 1 to 10 U of peptide/well. With three additional extracts, all except peak A were present. These data demonstrate that peptides present in multiple HPLC fractions common to two melanoma lines reconstitute epitopes for melanoma-specific CTL.

First dimension HPLC fractions that reconstituted melanoma-specific epitopes on T2 cells were fractionated a second time using either HFA (open squares) or HFBA (solid circles) as an organic modifier, and fractions were evaluated for reconstitution of CTL epitopes by addition to T2 cells, as shown in FIG. 7, A to E,. In each graph, a dotted horizontal line represents the background lysis of T2 cells by CTL only. FIG. 7A shows HFBA separation of 31 U of Peak A peptides from DM93 cells; FIG. 7B HFA and HFBA separations of 22 U of peak B peptides from DM93; FIG. 7C HFA and HFBA separations of 24 U of peak C peptides from DM93; FIG. 7D HFA and HFBA separations of 22 U of peak D peptides from DM93; and FIG. 7E HFA and HFBA separations of 7 U of peak D peptides from DM6. Because of its highly polar nature, peak A was separated using HFBA only. A single reconstituting peak was identified in FIG. 7A. Second dimension separations of peaks B and D revealed a single peak of activity in both HFA and HFBA (FIG. 7B, 7D, 7E). The activity from peak D appears at identical fractions in HFA and in HFBA for both DM6 and DM93 (FIG. 7D, 7E). Separation of the peak C HFA resulted in two peaks of reconstitution whereas HFBA gave one broad peak (FIG. 7C). With the resolution of peak C into two peaks, and including peak B1, a total of at least six shared CTL epitopes are demonstrated. These epitopes are labeled A2Mel-A, A2Mel-B, A2Mel-B1, A2Mel-C1, A2Mel-C2, and A2Mel-D.

In the peptide mixture responsible peak B, one peptide was identified as Sequence Tyr Met Asp Gly Thr Met Ser Gly Val (SEQ ID NO:9). The peptide is identical to a portion of the tyrosinase protein except at Position 3 where an Asp(D) is found instead of Asn(N).

Example VI

Peptides Recognized by Melanoma-Specific CTL

HLA-A2.1 molecules were immunoaffinity purified from detergent lysates of the human melanoma cell line DM6. The associated peptides were released by acid extraction, separated from HLA-A2.1 and antibody by filtration, and fractionated by multiple stages of HPLC. At each stage, HPLC fractions containing relevant peptides were identified by testing their ability to reconstitute epitopes for two melanoma-specific CTL lines, VMM5 and DM204-13, after incubation with the HLA-A2.1 positive lymphoblastoid cell line T2 In FIG. 8A peptides bound to A2.1 molecules were extracted and fractionated by reversed-phase HPLC, C. L. Slingluff Jr., et al, J. Immunol. (1993) 50, 2955, by using a gradient of acetonitrile/0.085% trifluoroacetic acid (TFA) in 0.1% TFA with acetonitrile increasing from 0 to 9% (0–5 min), 9 to 36% (5–55 min), 36 to 60% (55–62 min) (v/v), collecting one-minute fractions. In FIG. 8B Fractions 2 and 3 from the separation shown in panel A were pooled and rechromatographed with a 55 minute gradient of 0 to 30% acetonitrile/0.1% heptafluorobutyric acid (HFBA) in 0.1% HFBA, collecting one-minute fractions. For both panels, peptide: fractions were incubated for 2–3h with $2\times10^3$ 51Cr-labelled T2 cells in 150 11 assay media per well in 96-well plates. CTL were added to give an effector:target ratio of 10:1, and a standard chromium release assay was conducted. The panels show lysis of target cells plus peptide by VMM5 CTL (open circles), DM204-13 CTL (closed circles) and media only (solid line without symbols). Lysis of T2 cells without peptide by VMM5 CTL was 0.3% in (A) and 0.8% in (B) and by DM204-13 CTL was 0.7% in (A) and −0.2% in (B), while positive control lysis of HLA-A2+ melanoma cells by VMM5 CTL was 41% in FIGS. 8A and 67% in FIG. 8B and by DM204-13 CTL was 28% in FIGS. 8A and 78% in FIG. 8B.

Figure 8A:
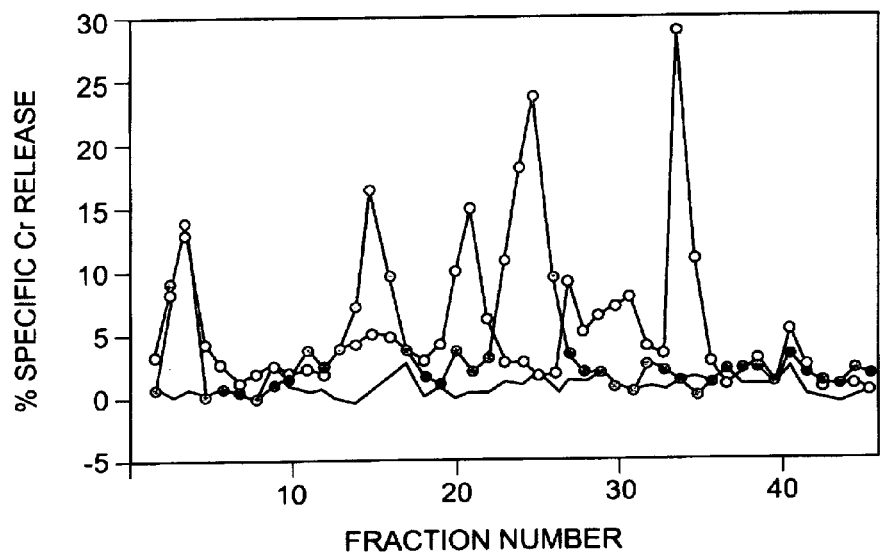
FIG. 8 illustrates the reconstitution of epitopes for two melanoma-specific CTL lines with HPLC fractions derived from naturally processed peptides extracted from HLA-A2.1 molecules (FIG. 8A initial fractionation.
FIG. 8B, result of pooling fractions 2 and 3 from FIG. 8A and rechromatographing)
Figure 8B:
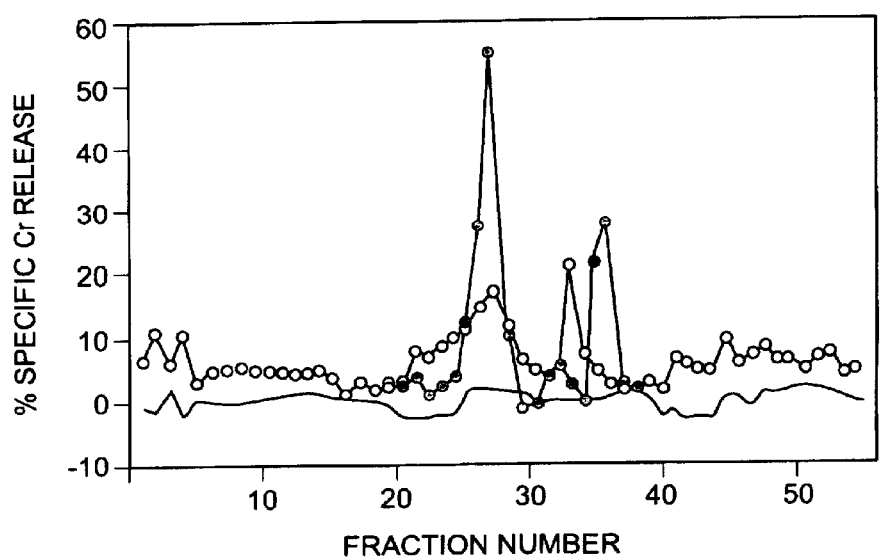

After first dimension HPLC separation, six peaks of activity were identified for VMM5 and three for DM204-13 as shown in FIG. 8A. Fractions 2–3 and 14–15 appeared to contain peptides recognized by both CTL lines. However, several hundred peptides were detected by mass spectrometry in each of the active fractions in this chromatograph. Consequently, fractions 2 and 3 were pooled and submitted to a second separation using HFBA instead of TFA as the organic modifier, FIG. 8B. Two peaks of activity were found for each CTL line, one of which contained peptides recognized by both. The most active fractions in the peak recognized by both CTL lines still contained over 50 peptides. The m/z values for a number of peptides that reconstituted epitopes for each CTL line were determined based on their presence in active fractions and absence in adjacent inactive fractions. The number of candidate peptides exceed the number that could be sequenced with available material.

Applicants used a peptide elution strategy to identify CTL epitopes among oligopeptides corresponding to selected segments of pMel-17. The use of a novel apparatus, which split a microcapillary stream into two streams in capillaries of different diameter and thereby permitted simultaneous immunological and mass spectrometric analysis of the effluent from a microcapillary HPLC column used for the initial fractionation, greatly facilitated this evaluation. For example, an HPLC fraction which mass spectra showed to contain at least 25 peptides contained only three whose relative abundances matched the activity profile for CTLs from DM 204. One of these three (peptide 946) was later confirmed as active. It was not predictable, prior to this work, that this splitting could be achieved without undue turbulence.

Figure 9A:
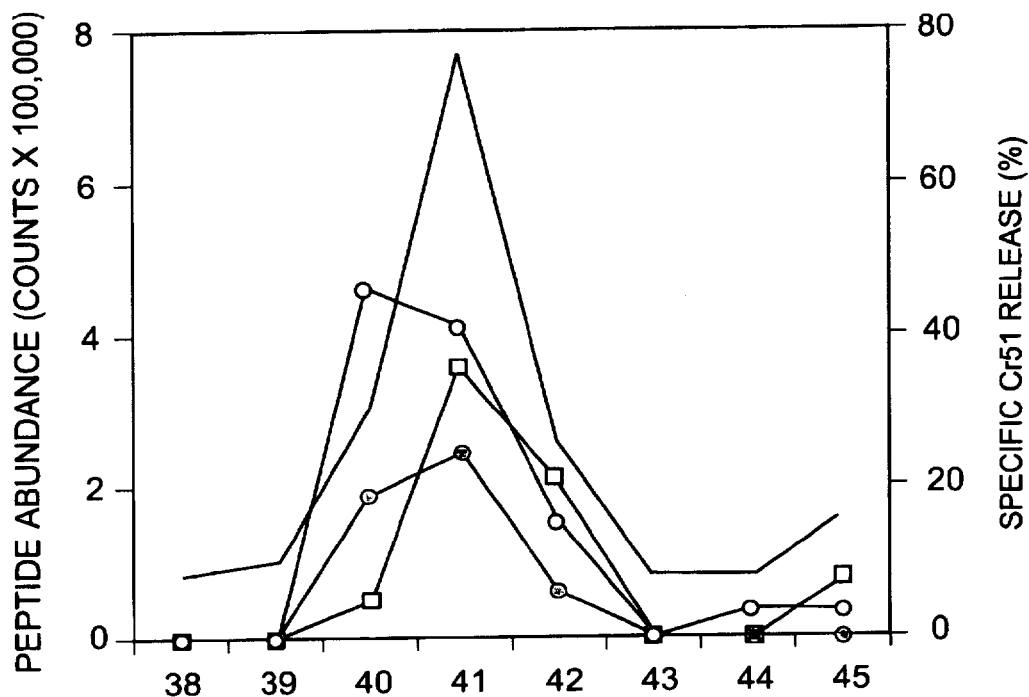
FIG. 9 graphs the identification of candidate peptides (FIG. 9A) by mass spectrometry and correlates it with the activity profile for DM204-13 (FIG. 9B)
Figure 9B:
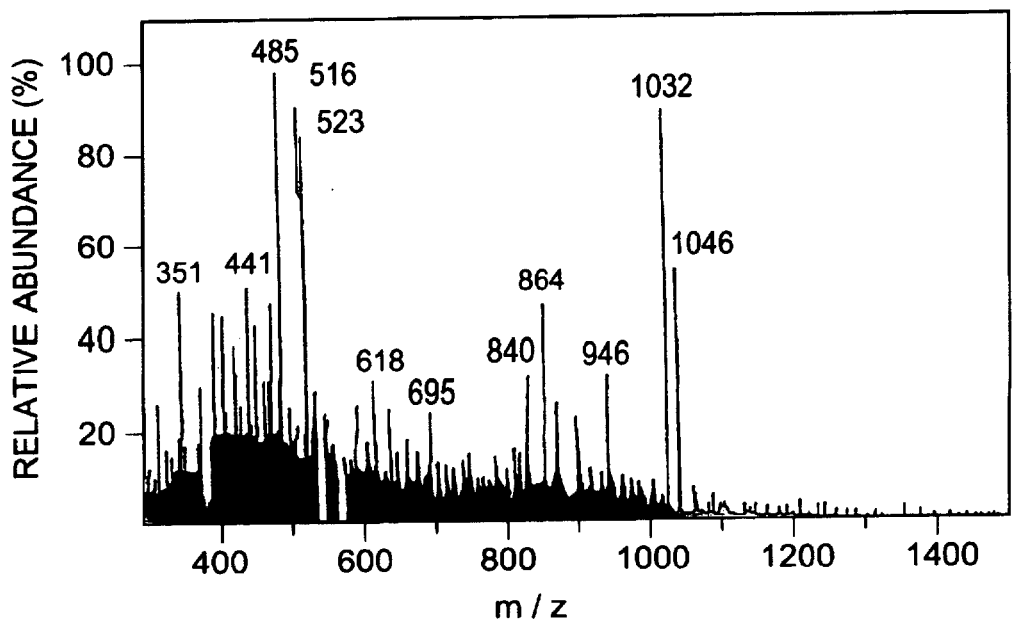

Second dimension HPLC fractions 26 and 27 from FIG. 8B were injected into an electrospray ionization tandem mass spectrometer using a novel online microcapillary column effluent splitter which directs the effluent simultaneously to the mass spectrometer and to the wells of a microtiter plate. Because third dimension separations using standard HPLC methods resulted in large losses of material and failed to reduce significantly the number of candidate peptides, a specific apparatus was constructed. A PRP-1 (Hamilton) microcapillary HPLC column (100 μm by 22 cm) was butt-connected using a zero dead volume union (Valco) to two small capillaries of different lengths and interior diameters (25 μm and 40 μm ID, Polymicro Technologies). The column was eluted into the union with a 34 minute gradient of 0 to 60% acetonitrile. The 20 μm capillary deposited ⅙ of the material into 50 μl of culture media in microtiter plate wells. The larger of the two capillaries directed the remaining ⅚ of the material into the electrospray ionization source, and mass spectra of the peptides deposited in each well were recorded on a Finnigan-MAT (San Jose, Calif.) triple quadrupole mass spectrometer, R. A. Henderson et al., Proc. Natl. Acad. Sci. USA 90, 10275 (1993). A subsequent chromium release assay identified the wells containing peptide epitopes. Second dimension HPLC fractions 26 and 27 were pooled and analyzed using this apparatus. Both CTL lines showed a single peak of activity. Mass spectra showed that these fractions contained approximately 50 peptides (FIG. 9A), but the relative abundances of only three of these (with m/z values of 1046, 946 and 864) matched the activity profile for DM204-13 (FIG. 9B). In FIG. 9A, the summation of mass spectra recorded on peptides deposited in well 41 are illustrated. Many of these were eliminated as candidates because their relative abundance failed to correlate with the observed lysis. In FIG. 9B the bold solid line indicates percent lysis as determined by chromium release assay. Peptide amount, as indicated by ion abundance, is plotted for m/z 1046 (open circles), m/z 946-(solid circles), and m/z 864 (open squares).

Figure 10A:
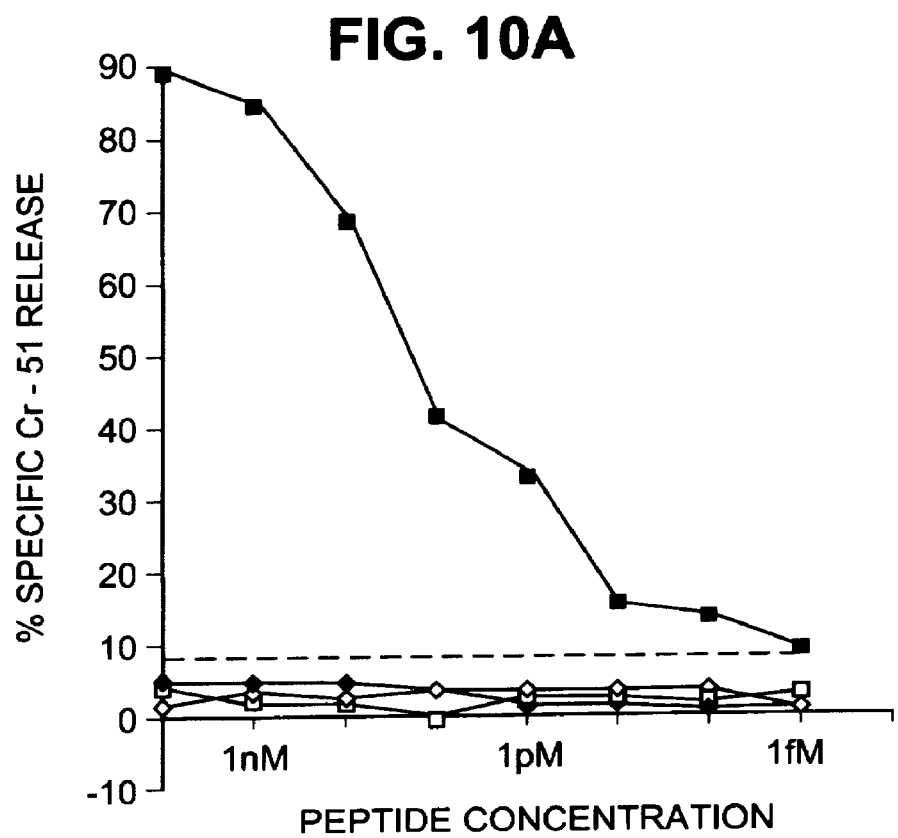
FIG. 10 illustrates the dose-titration curves for synthetic peptideswith respect to reconstituting an epitope for melanoma-specific CTL VMM5 (FIG. 10A) and DM204-13 (FIG. 10B)
Figure 10B:
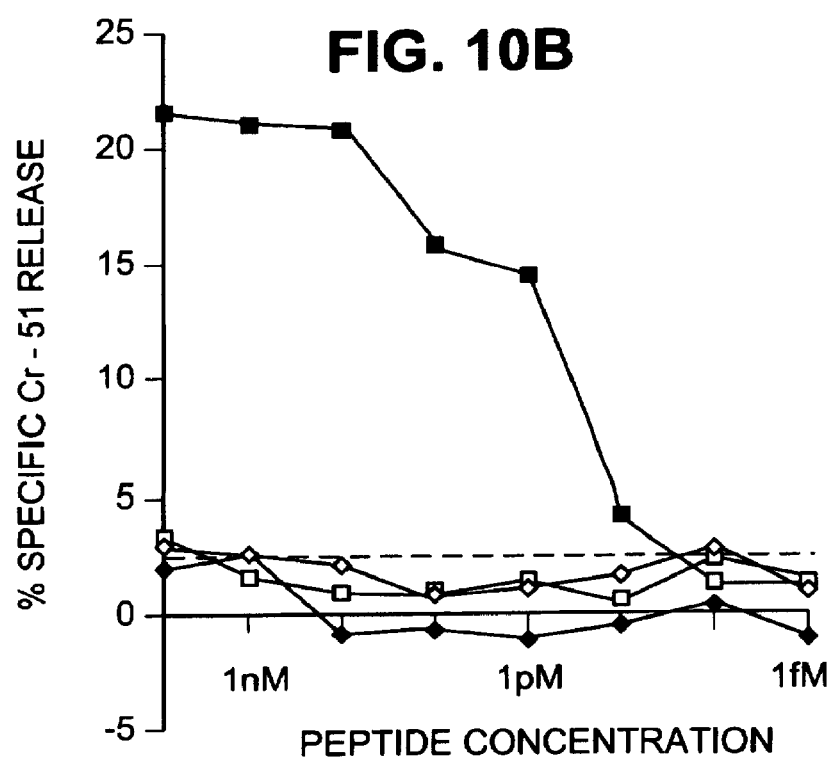

Collision-activated dissociation analyses performed on the $(M+H)^+$ ions for each of these three peptides difined their amino acid sequences as: m/z 864, Ser Met Ala Gly Asn Thr Ser Val (SEQ ID NO:124); 946 (SEQ ID NO:123) where X=L or I; and 1046, Ala Xaa Tyr Asp Ala Thy Tyr Glu Thr (SEQ ID NO:125). The sequenced peptides were synthesized, using an equimolar mixture of Leu and Ile in place of X. The ability to reconstitute an epitope for melanoma specific CTL VMM5, and DM204-13, illustrated in FIGS. 10A and 10B, is shown for peptides 946 (closed squares), 864 (open squares), and 1046 (open circles). Lysis of T2 without peptide is represented by a horizontal dotted line. As shown in FIG. 10, peptide 946 reconstituted the epitopes for both VMM5 and DM204-13, with half-maximal reconstitution achieved between 1 and 10 pM. When tested independently, both (SEQ ID NO:14) and (SEQ ID NO:39) effectively reconstituted the epitope for VMM5 at similar concentrations. Peptides 864 and 1046 had no effect at concentrations up to 10 nM. The amount of peptide 946 present in well 41 in the experiment shown in FIG. 9B corresponded to a concentration of 8 pM, indicating that the synthetic 946 peptide sensitized at doses comparable to that of the naturally occurring species.

Peptide 946 reconstitutes T cell recognition at concentrations that are at least two orders of magnitude lower than those of several optimized HLA-A2.1 restricted epitopes of viral or cellular origin. The antigenicity of this peptide could be explained by high affinity for the MHC or high affinity of the TcR. The ability of the test peptides to compete with the raiolabeled standard peptide Phe Leu Pro Ser Asp Tyr Phe Pro Ser Val (SEQ ID NO:126) for binding to purified HLA-A2.1 molecules was measured using an equilibrium binding assay, J. Ruppert et al., Cell 74, 929 (1993) and Y. Chen et al., J. Immunol. in press (1994) with (Open Squares) (SEQ ID NO:14) (peptide 946L); (solid diamonds) (SEQ ID NO:39) (peptide 946I); (solid squares) Ala Leu Trp Gly Phe Phe Pro Val Leu (SEQ ID NO:1127) endogenous peptide isolated from HLA-A2.1, R. A. Henderson et al. Proc. Natl. Acad. Sci. USA 90 10275 (1993); (open diamonds), Ala Pro Arg Thr Val Ala Leu Thr Ala (SEQ ID NO:128) and endogenous peptide isolated from HLA-B7, E. L. Huczko et al., J. Immunol. 151, 2572 (1993). The concentrations giving 50% inhibition of binding of a standard peptide to purified HLA-A2.1 molecules were 1.06 microM and 13.7 microM for the Leu and Ile version of the 946 peptide, respectively as illustrated in the graph of FIG. 11. While the Leu version of 946 contains the predicted motif residues at positions 2 and 9 that support peptide binding to HLA-A2.1, the substitution of Ile at position 2 is expected to lower affinity by about a factor of 10. However, both of these values lie well outside the 5–30 nM range observed for several other naturally processed peptides, and indicate the 946 isomers have considerably lower affinities. This may be due in part to the presence of a negatively charged residue at position 3, which is predicted to have a detrimental effect on binding. In keeping with the low affinity of peptide 946 for HLA-A2.1, this molecule is not present in high copy number on the cell surface. The sequence of 946 was obtained from 15 fmol of peptide present in a second dimension HPLC fraction representative of $4 \times 10^{10}$ DM6 cells. Assuming a 5% overall yield through purification and extraction and 3 HPLC separations, it is calculated that 946-HLA-A2.1 complexes are present at only 5 copies per melanoma cell. This number is well below the 50–200 copies/cell estimated to be necessary for T cell recognition. It is conceivable that, due to the low affinity of 946 for the HLA-A2.1 molecule, the peptide may have been disproportionately lost during the washes that accompany the affinity purification procedure. Regardless, the ability of this peptide to sensitize for CTL-mediated lysis at concentrations that are $10^4$–$10^5$ lower than the $IC_{50}$ value indicates that CTL lines VMM5 and DM204-13 have an extremely high affinity for this epitope.

Figure 12:
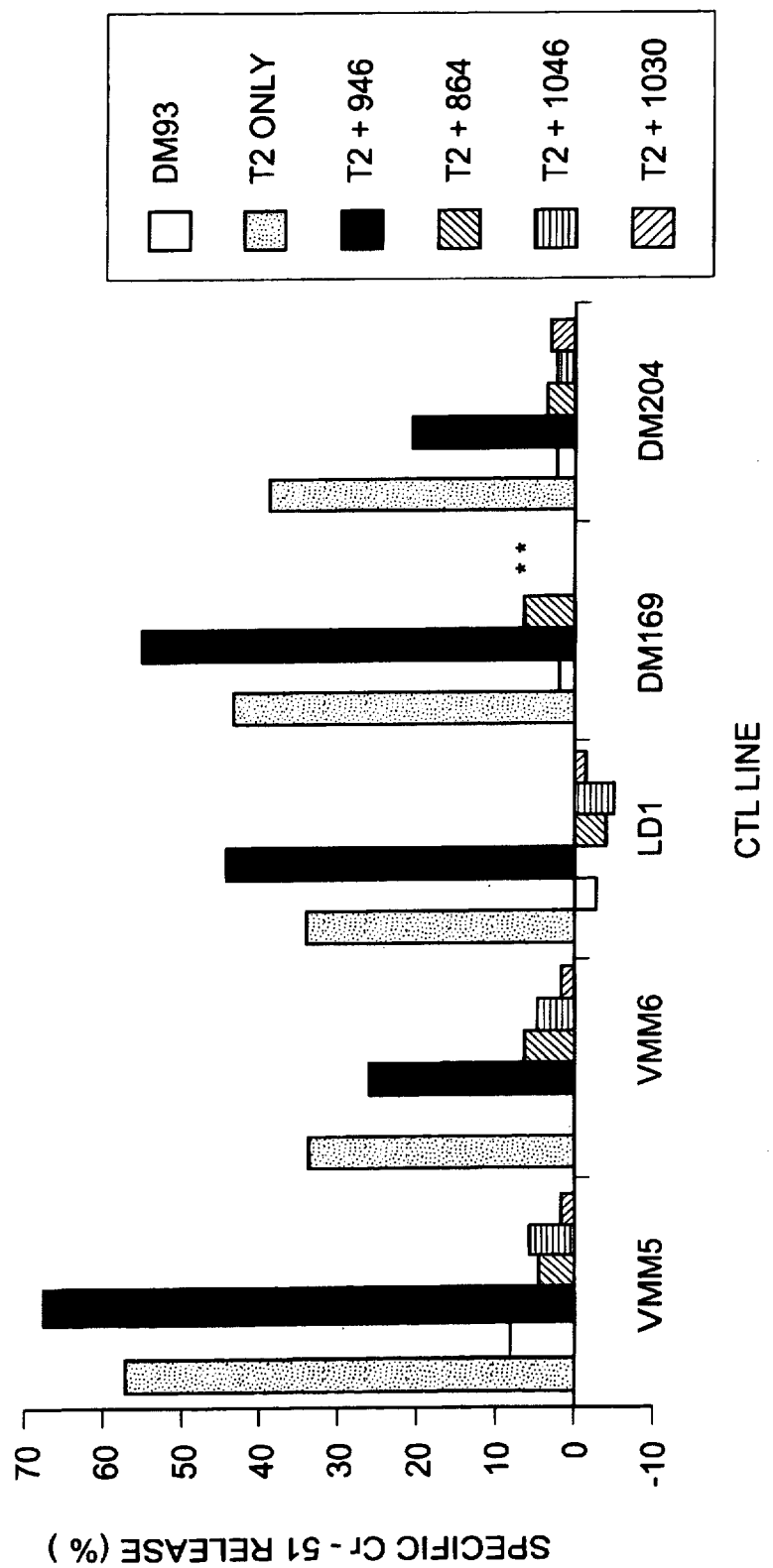
FIG. 12 illustrates the peptide 946 reconstitutes epitope for 5 melanoma-specific CTL lines in a standard chromium release assay.

To determine whether peptide 946 was a generally relevant epitope for HLA-A2.1 restricted melanoma specific CTL, lines from 3 additional patients were tested. CTL lines VMM5 and VMM6 were generated by stimulation with autologous tumor. VMM5 CTL were maintained on allogeneic. A2.1+melanoma DM6 after specificity was obtained, C. L. Slingluff Jr. et al., J. Immunol. 150, 2955 (1993). DM169-13 and DM204-13 CTL were generated by stimulation with allogeneic A2.1+melanoma DM13, N. J. Crowley et al., J. Immunol. 146, 1692 (1991), then maintained with DM6. LD1 CTL were stimulated on a rotating schedule of stimulating allogeneic A2.1+melanomas DM6, DM13, and DM93. DM93 is an HLA-A2.1+melanoma used as a positive control. Peptides were synthesized by solid phase Fmoc chemistry on Wang resins with a Gilson (Middleton, Wis.) Model AMS 422 multiple peptide synthesizer. T2 cells were preincubated with the peptides whose $(M+H)^+$ values are indicated in the legend, FIG. 12. Peptide 946 was used at a concentration of 0.1 nM, except 1 nM for DM169. All other peptides were used at a concentration of 10 nM except 250 nM for DM169 and 0.1 nM for LD1. Asterisks (*) mark peptides not evaluated. The sequences of the peptides 864 (Seq. ID No. 88), 946 (SEQ. ID NO.:39), 1046 (SEQ. ID NO:89) are described in the text. Peptide 1030 has the sequence (SEQ ID NO:94) (peptide from tyrosinase molecule). The 946 peptide, at concentrations of 0.1–1 nM, shown in FIG. 12, reconstituted recognition by each of these 3 lines, while neither 864 nor 1046 had any detectable activity at equal or higher concentrations. Dose response curves obtained for two of these lines showed half-maximal lysis in the 1–10 pM range. These results establish that 5 out of 5 patients examined had high affinity t-cells that recognized the HLA-A2.1-associated peptide 946. An additional peptide (SEQ ID NO:94), which originates from tyrosinase and had been identified by Boon and colleagues as an HLA-A2.1 restricted melanoma specific T cell epitope, was also evaluated. None of 4 CTL lines recognized cells incubated with this peptide.

These five CTL lines were established in two different laboratories using varied stimulation protocols and several different stimulating tumors. Most were stimulated initially with autologous tumor (VMM6, VMM5) or allogeneic A2.1+melanoma DM13 (DM169-13, DM204-13), although many were maintained on DM6 after specificity was obtained. None of the CTL lines was stimulated exclusively with DM6, the line from which the 946 peptide was identified. The VMM6 CTL line was stimulated exclusively with autologous fresh cryo-preserved tumor. Its recognition of 946 is evidence that the T-cell response to that peptide does not require stimulation with DM6, and that fresh VMM6 melanoma cells must present the 946 peptide in a manner that induces a CTL response. The fact that all five lines recognize this 946 peptide despite their varied origins is strong evidence that this peptide may be capable of stimulating a CTL response in a large number of HLA-A2.1$^+$ individuals.

The Leu containing version of peptide 946 (SEQ. ID NO.:14) was found in a protein identified as Pmel-17, B. S. Kwon et al., *Proc. Natl. Acad. Sci. USA* 88, 9228 (1991, B. S. Kwon et al., *Molecular Biology and Medicine* 4, 339 (1987). Pmel-17 is a 645 amino acid protein expressed in melanocytes and melanoma and has not been detected in nonpigmented cells, B. S. Kwon et al., *Proc. Natl. Acad. Sci. USA* 88, 9228 (1991; B. S. Kwon et al., *Molecular Biology and Medicine* 4, 339 (1987). Although its function is unknown, it has been postulated to be a component of the melanin biosynthetic pathway, B. S. Kwon et al., *Proc. Natl. Acad. Sci. USA* 88, 9228 (1991); B. S. Kwon et al., *Molecular Biology and Medicine* 4, 339 (1987). Its presence in melanocytes as well as melanoma is consistent with the observation that some melanoma specific CTL clones recognize melanocytes, A. Anichini et al, *J. Exp. Med.* 177, 989 (1993). This observation, coupled with the fact that spontaneous remissions of human melanoma have been observed in conjunction with the simultaneous development of vitiligo, T. C. Everson and W. H. Cole, Eds., *Spontaneous Regression of Cancer* (W. B. Saunders Company, Philadelphia, 1966), suggests that an autoimmune response directed against melanocytes may be a natural accompaniment to the development of immunity to melanoma. Although we do not yet have evidence that 946-specific CTL recognize normal melanocytes, the possibility that 946 is one of the epitopes responsible for cross-reactivity of melanoma-specific CTL with normal melanocytes raises questions about the relationship between tumor immunity and autoimmunity.

Example VII

After identification of a melanoma specific CTL epitope from the protein PMEL17 (SEQ ID NO:123), wherein Xaa is Ile or Leu)(PEPTIDE 946I or 946L), other possible epitopes consisting of 9, 10, or 11 amino acids from PMEL17 were synthesized. To select possible epitopes, A2.1 motif information previously generated previously was used. A Gilson AMS 422 Multiple Peptide Synthesizer was used to make the synthetic peptides, which permits synthesis of only 48 peptides at one time. Due to the need to synthesize other peptides, the first set of peptides derived from PMEL17 was synthesized and contained 38 nonamers with Leu, Ile, or Met at position 2 and Leu, Ile, Val, or Ala at position 9. The sequences of these nonamers are shown below. They include the two versions of the biologically active peptide (SEQ ID NO:123) wherein Xaa=Leu or Ile, one version with Leu at Position 2 (Seq. Id. No. 14) and one version with Ile at Position 2 (Seq. Id. No. 39). The second batch synthesized included nonamers with Thr at the ninth position, as well as 10 and 11 mers with Leu or Met at position 2 and Leu, Ile, Val, Ala, or Thr at position 9. Not all of the 11 mers with this motif were synthesized. The list of these peptides is also shown below.

Example VIII

Peptides Synthesized 9-mers

SEQ. ID. NO. 1 Asp-Leu-Val-Leu-Lys-Arg-Cys-Leu-Leu
SEQ. ID. NO. 2 Leu-Leu-His-Leu-Ala-Val-Ile-Gly-Ala
SEQ. ID. NO. 3 His-Leu-Ala-Val-Ile-Gly-Ala-Leu-Leu
SEQ. ID. NO. 4 Leu-Leu-Ala-Val-Gly-Ala-Thr-Lys-Val
SEQ. ID. NO. 5 Gln-Leu-Tyr-Pro-Glu-Trp-Thr-Glu-Ala
SEQ. ID. NO. 6 Val-Ile-Trp-Val-Asn-Asn-Thr-Ile-Ile.
SEQ. ID. NO. 7 Val-Leu-Gly-Gly-Pro-Val-Ser-Gly-Leu
SEQ. ID. NO. 8 Gly-Leu-Ser-Ile-Gly-Thr-Gly-Arg-Ala
SEQ. ID. NO. 9 Tyr-Met-Asp-Gly-Thr-Met-Ser-Gln-Val
SEQ. ID. NO. 10 Ser-Ile-Gly-Thr-Gly-Arg-Ala-Met-Leu
SEQ. ID. NO. 11 Met-Leu-Gly-Thr-His-Thr-Met-Glu-Val
SEQ. ID. NO. 12 Gln-Leu-His-Asp-Pro-Ser-Gly-Tyr-Leu
SEQ. ID. NO. 13 Thr-Leu-Ile-Ser-Arg-Ala-Pro-Val-Val
SEQ. ID. NO. 14 Tyr-Leu-Glu-Pro-Gly-Pro-Val-Thr-Ala
SEQ. ID. NO. 15 Gly-Met-Thr-Pro-Glu-Lys-Val-Pro-Val
SEQ. ID. NO. 16 Gly-Met-Thr-Pro-Ala-Glu-Val-Ser-Ile
SEQ. ID. NO. 17 Ser-Ile-Thr-Gly-Ser-Leu-Gly-Pro-Leu
SEQ. ID. NO. 18 Pro-Leu-Leu-Asp-Gly-Thr-Ala-Thr-Leu
SEQ. ID. NO. 19 Thr-Leu-Arg-Leu-Val-Lys-Arg-Gln-Val
SEQ. ID. NO. 20 Arg-Leu-Val-Lys-Arg-Gln-Val-Pro-Leu
SEQ. ID. NO. 21 Asp-Ile-Val-Gln-Gly-Ile-Glu-Ser-Ala
SEQ. ID. NO. 22 Val-Leu-Pro-Ser-Pro-Ala-Cys-Gln-Leu
SEQ. ID. NO. 23 Ser-Leu-Ala-Asp-Thr-Asn-Ser-Leu-Ala
SEQ. ID. NO. 24 Ser-Leu-Ala-Val-Val-Ser-Thr-Gln-Leu
SEQ. ID. NO. 25 Gln-Leu-Ile-Met-Pro-Val-Pro-Gly-Ile
SEQ. ID. NO. 26 Leu-Ile-Met-Pro-Val-Pro-Gly-Ile-Leu
SEQ. ID. NO. 27 Ile-Met-Pro-Val-Pro-Gly-Ile-Leu-Leu
SEQ. ID. NO. 28 Gly-Ile-Leu-Leu-Thr-Gly-Gln-Glu-Ala
SEQ. ID. NO. 29 Leu-Leu-Thr-Gly-Gln-Glu-Ala-Gly-Leu
SEQ. ID. NO. 30 Gly-Leu-Gly-Gln-Val-Pro-Leu-Ile-Val
SEQ. ID. NO. 31 Pro-Leu-Ile-Val-Gly-Ile-Leu-Leu-Val
SEQ. ID. NO. 32 Leu-Ile-Val-Gly-Ile-Leu-Leu-Val-Leu
SEQ. ID. NO. 33 Gly-Ile-Leu-Leu-Val-Leu-Met-Ala-Val
SEQ. ID. NO. 34 Ile-Leu-Leu-Val-Leu-Met-Ala-Val-Val
SEQ. ID. NO. 35 Leu-Leu-Val-Leu-Met-Ala-Val-Val-Leu
SEQ. ID. NO. 36 Leu-Met-Ala-Val-Val-Leu-Ala-Ser-Leu
SEQ. ID. NO. 37 Arg-Leu-Met-lys-Gln-Asp-Phe-Ser-Val
SEQ. ID. NO. 38 Pro-Ile-Gly-Glu-Asn-Ser-Pro-Leu-Leu
SEQ. ID. NO. 39 Tyr-Ile-Glu-Pro-Gly-Pro-Val-Thr-Ala
10 mers
SEQ. ID. NO. 40 Val-Leu-Lys-Arg-Cys-Leu-Leu-His-Leu-Ala
SEQ. ID. NO. 41 Cys-Leu-Leu-His-Leu-Ala-Val-Ile-Gly-Ala
SEQ. ID. NO. 42 Leu-Leu-His-Leu-Ala-Val-Ile-Gly-Ala-Leu
SEQ. ID. NO. 43 His-Leu-Ala-Val-Ile-Gly-Ala-Leu-Leu-Ala
SEQ. ID. NO. 44 Ala-Leu-Leu-Ala-Val-Gly-Ala-Thr-Lys-Val SEQ. ID. NO. 45 Trp-Leu-Gly-Val-Ser-Arg-Gln-Leu-Arg-Thr SEQ. ID. NO. 46 Arg-Leu-Asp-Cys-Trp-Arg-Gly-Gly-Gln-Val SEQ. ID. NO. 47 Ser-Leu-Lys-Val-Ser-Asn-Asp-Gly-Pro-Thr SEQ. ID. NO. 48 Ala-Leu-Asn-Phe-Pro-Gly-Ser-Gln-Lys-Val SEQ. ID. NO. 49 Ala-Met-Leu-Gly-Thr-His-Thr-Met-Glu-Val SEQ. ID. NO. 50 Met-Leu-Gly-Thr-His-Thr-Met-Glu-Val-Thr SEQ. ID. NO. 51 Pro-Leu-Ala-His-Ser-Ser-Ser-Ala-Phe-Thr SEQ. ID. NO. 52 Ala-Leu-Asp-Gly-Gly-Asn-Lys-His-Phe-Leu SEQ. ID. NO. 53 Phe-Leu-Arg-Asn-Gln-Pro-Leu-Thr-Phe-Ala SEQ. ID. NO. 54 Gln-Leu-His-Asp-Pro-Ser-Gly-Tyr-Leu-Ala SEQ. ID. NO. 55 Tyr-Leu-Ala-Glu-Ala-Asp-Leu-Ser-Tyr-Thr SEQ. ID. NO. 56 Thr-Leu-Ile-Ser-Arg-Ala-Pro-Val-Val-Thr SEQ. ID. NO. 57 Pro-Leu-Thr-Ser-Cys-Gly-Ser-Ser-Pro-Val SEQ. ID. NO. 58 Thr-Leu-Ala-Glu-Met-Ser-Thr-Pro-Glu-Ala SEQ. ID. NO. 59 Gly-Met-Thr-Pro-Ala-Glu-Val-Ser-Ile-Val SEQ. ID. NO. 60 Val-Leu-Ser-Gly-Thr-Thr-Ala-Ala-Gln-Val SEQ. ID. NO. 61 Ser-Leu-Gly-Pro-Leu-Leu-Asp-Gly-Thr-Ala SEQ. ID. NO. 62 Leu-Leu-Asp-Gly-Thr-Ala-THr-Leu-Arg-Leu SEQ. ID. NO. 63 Val-Leu-Tyr-Arg-Tyr-Gly-Ser-Phe-Ser-Val SEQ. ID. NO. 64 Glu-Leu-Thr-Val-Ser-Cys-Gln-Gly-Gly-Leu SEQ. ID. NO. 65 Gly-Leu-Pro-Lys-Glu-Ala-Cys-Met-Glu-Ile SEQ. ID. NO. 66 Val-Leu-Pro-Ser-Pro-Ala-Cys-Gln-Leu-Val SEQ. ID. NO. 67 Ser-Leu-Ala-Asp-Thr-Asn-Ser-Leu-Ala-Val SEQ. ID. NO. 68 Ser-Leu-Ala-Val-Val-Ser-Thr-Gln-Leu-Ile SEQ. ID. NO. 69 Gln-Leu-Ile-Met-Pro-Val-Pro-Gly-Ile-Leu SEQ. ID. NO. 70 Ile-Leu-Leu-Val-Leu-Met-Ala-Val-Val-Leu SEQ. ID. NO. 71 Ile-Leu-Leu-Thr-Gly-Gln-Glu-Ala-Gly-Leu SEQ. ID. NO. 72 Pro-Leu-Ile-Val-Gly-Ile-Leu-Leu-Val-Leu SEQ. ID. NO. 73 Leu-Leu-Val-Leu-Met-Ala-Val-Val-Leu-Ala SEQ. ID. NO. 74 Val-Leu-Met-Ala-Val-Val-Leu-Ala-Ser-Leu SEQ. ID. NO. 75 Leu-Met-Ala-Val-Val-Leu-Ala-Ser-Leu-Ile SEQ. ID. NO. 76 Gln-Leu-Pro-His-Ser-Ser-Ser-His-Trp-Leu SEQ. ID. NO. 77 Val-Leu-Pro-Asp-Gly-Gln-Val-Ile-Trp-Val 9 mers with Thr in position 9

SEQ. ID. NO. 78 Leu-Ile-Ser-Arg-Ala-Pro-Val-Val-Thr

SEQ. ID. NO. 79 Val-Leu-Gln-Ala-Ala-Ile-Pro-Leu-Thr

SEQ. ID. NO. 80 Ser-Ile-Val-Val-Leu-Ser-Gly-Thr-Thr

SEQ. ID. NO. 81 Ser-Ile-Met-Ser-Thr-Glu-Ser-Ile-Thr

SEQ. ID. NO. 82 Ser-Leu-Gly-Pro-Leu-Leu-Asp-Gly-Thr 11 mers

SEQ. ID. NO. 83 Leu-Leu-His-Leu-Ala-Val-Ile-Gly-Ala-Leu-Leu

SEQ. ID. NO. 84 Cys-Leu-Leu-His-Leu-Ala-Val-Ile-Gly-Ala-Leu

SEQ. ID. NO. 85 His-Leu-Ala-Val-Ile=Gly-Ala-Leu-Leu-Ala-Val

SEQ. ID. NO. 86 Asp-Leu-Val-Leu-Lys-Arg-Cys-Leu-Leu-His-Leu

SEQ. ID. NO. 87 Val-Leu-Lys-Arg-Cys-Leu-Leu-His-Leu-Ala-Val

Additional Sequences

SEQ. ID. NO. 88 Ser-Met-Ala-Pro-Gly-Asn-Thr-Ser-Val

SEQ. ID. NO. 89 Ala-Xaa-Tyr-Asp-Ala-Thr-Tyr-Glu-Thr, wherein Xaa=Leu or Ile.

Figure 13:
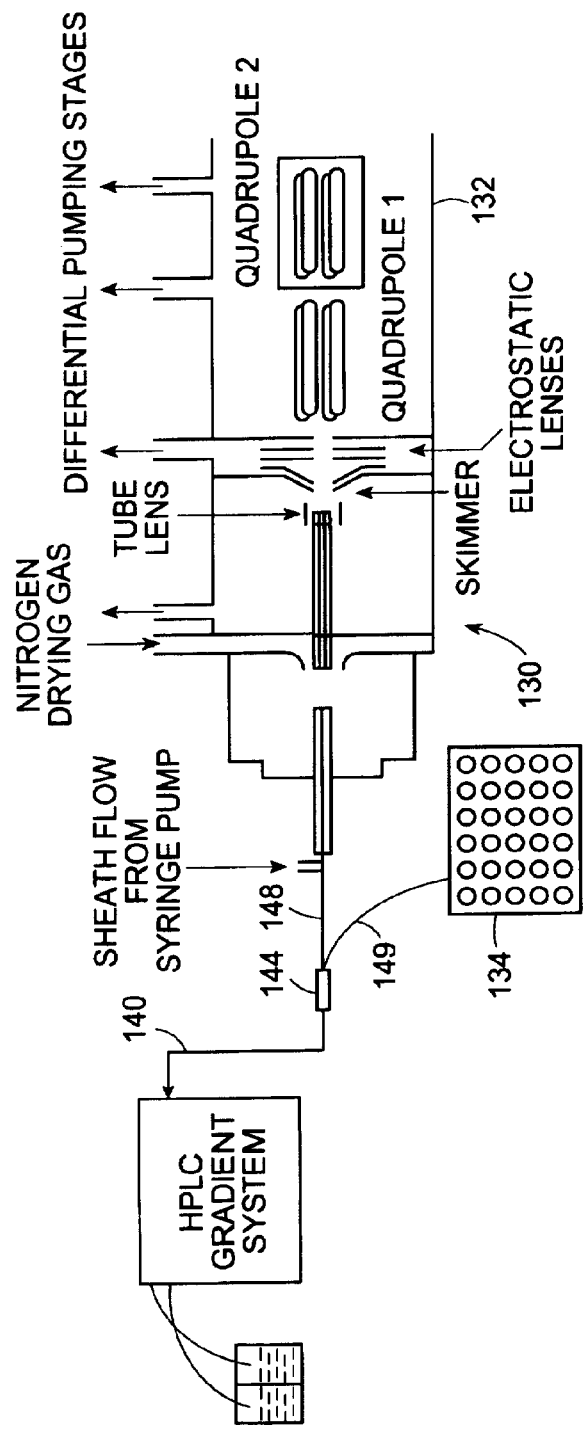
FIG. 13 is a side view of the splitter.
Figure 14:
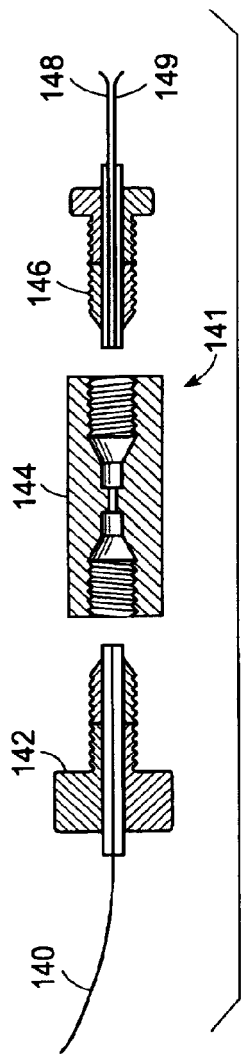
FIG. 14 is a side view of peptide sequencing by microcapillary liquid chromatography/electrospray ionization tandem mass spectrometry.

In order to identify active peptides in the complex mixture obtained from the melanoma cells described above, it was necessary to find a way to split a column of liquid flowing at a rate of 840 nl/min into two equal parts without introducing turbulence (dead volume) that would destroy the chromatographic separatino achieved in the microcapillary column. Commercially available low-dead volume connections were evaluated and found to be totally unsatisfactory in the above regard. Fortunately, the system shown in FIG. 13 worked beautifully. Chromatographic resolution was found to be the same with or without the splitter in the system. The splitter is rapid to assemble and are extremely dependable. The splitter consists of a 250 microm bore SS union. Inserted into one side is a PEEK ferrule and nut containing a 350 microm o.d.×100 microm i.d. fused silica column packed with POROS beads and stuffed into Teflon tubing (1/16 inch×3 mm). Inserted into the other side is a second PEEK ferrule with SS nut containing two equal lenghts of 140 uicrom o.d.×25 microm i.d. silylated fused silica tubing also stuffed into Teflon tubing (1/16 inch×0.3 mm). Compression of the teflon tubing creat4es the zero dead volume union. The system is illustrated in FIGS. 13 and 14.

Electrospray ionization tandem mass spectrometry system 130 with online microcapillary column effluent splitter 141 to direct the effluent simultaneously to the mass spectrometer 132 and to the wells of a microtiter plate 134. A microcapillary HPLC column 140 (typically 100 μm by 22 cm) was butt connected using a zero dead volume union 144 (Valco) to two small capillaries 148 and 149 of different lengths and interior diamters (typically 25 μm and 40 μm ID, Polymicro Technologies). Typically the column was eluted with an approximate flow rate of 500 nl/min into the union with a 34 minute gradient of 0 to 60% acetonitrile. The larger of the two capillaries directed 5/6 of the material into the electrospray ionization source (Analytica) and mass spectra were recorded on the material using a Finnigan-MAT TSQ-700 (San Jose, Calif.) triple quadrupole mass spectrometer. The 20 μm capillary deposited the remaining 1/6 of the material into 50 μl of media in microtiter plate wells. This allows deposition of a few nanoliters of eluent into a well without loss of chromatographic resolution. Timing of the splitter is adjusted so that m/z values of the peptides are recorded at the instant in which they are deposited into the well, providing a record fo the peptides present in each well.

The chromium release assay described in FIG. 1 was used to determine which well contained the peptide portion of the epitope.

The above peptides were tested for activity in 51Cr release assay using the procedures set forth supra, and there was preliminary evidence that several had biologic activity as CTL epitopes. However, when confirmatory experiments were performed, the only peptides with substantial VMM6 (HLA-A2.1-restricted melanoma-specific) CTL stimulatory activity were peptides 946I (SEQ ID NO: 39) and 946L (SEQ ID NO: 14). This demonstrates the significance and serendipity of the discovery of the activity of the latter two peptides. The following table examines the CTL stimulatory activity of 946I and 946L at different concentrations:

% specific release (of Cr-51)

1 μM1 nM1 pM1 fM

T2+946-I 70.058.144.143.3

T2+946-L 69.473.953.652.0 T2+946-I (no CTL) 0.1–0.9–1.4–0.4 T2+946-L (no CTL)-1.4–1.7–1.4–1.8

Background lysis of T2 melanoma cells by the CTL was 29%. Positive control lysis, of HLA-A2+melanoma cell line DM6, was 72%. Thus, half-maximal lysis would be halfway between 29% and 70%–72%, or 50%; half-maximal lysis was observed between 1pM and 1 nM for 946I, and at 1fM for 946L. In other assays, 1pM has given half-maximal lysis for a 946L/I mix.

Example VIII

The naturally occurring peptide (SEQ ID NO:9) was tested for recognition by the tyrosinase specific CTL clone IVSB, which had been used to identify the genetically encoded peptide (SEQ ID NO:94). T. Wolfei, et. al., *Eur. J. Immuno.* 24, 759 (1994). Interestingly, (SEQ ID NO:9) sensitized target cells for lysis at a 100-fold lower concentration than did (SEQ ID NO:94) (half maximal lysis with 0.1 μM and 10 μM, respectively). Even when target cells were pretreated with the monoclonal antibody MA2.1 in order to facilitate exogenous peptide binding to HLA-A2.1. T. Wolfei, et al., *Eur. J. Immunol.* 24, 759 (1994; H. Bodmer et al., *Nature* 342, 443 (1989), the concentration of (SEQ ID NO:94) required to give half-maximal target cell lysis was greater than 1 μM. This is significantly higher than that observed for numerous other peptide epitopes. R. A. Henderson, et al., *Proc. Natl. Acad. Sci. USA* 90, 10275 (1993); A. L. Cox, et al., *Science* 264, 716 (1994); J. Bertoletti, et al., *J. Virol.* 67, 2376 (1993); U. Utz, et al., *J. Immunol.* 149, 214 (1992); M. A. Bednarek, et al., ibid. 147, 4047 (1991).

To determine whether differences in target cell sensitizing activity were due to differences in the ability of the individual peptides to bind to HLA-A2.1 molecules, the binding affinity of the two peptides was measured using a quantitative binding assay. Y. Chen, et al., *J. Immunol.* 152, 2874 (1994); J. Ruppert, et al., *Cell* 74, 929 (1993). Inhibition of the binding of a standard peptide to purified HLA-A2.1 molecules was observed at similar concentrations of (SEQ ID NO:9) and (SEQ ID NO:94). Thus, the asparagine and aspartic acid residues at position three of these peptides have either a similar or no influence on peptide binding to HLA-A2.1 and differences in binding affinity do not account for the difference in peptide recognition by the CTL.

Preferential CTL recognition of the naturally processed (SEQ ID NO:9) suggests that the T cell receptor expressed by the tyrosinase specific CTL clone IVSB has a greater affinity for this species. One possible explanation of these observations is that this aspartic acid containing peptide is derived from a previously undescribed allelic variant of tyrosinase or a mutated tyrosinase gene. Although asparagine has been found at this position (residue 371 of the precursor protein) in published sequences of human tyrosinase, B. S. Kwon, et al., *Proc. Natl. Acad. Sci USA* 84, 7473 (1987); B. Bouchard, et al., *J. Exp. Med.* 169, 2029 (1989); V. Brichard, et al., *J. Exp. Med.* 180, 35 (1994), an allelic form containing a threonine substitution at this position has been reported in oculocutaneous albino patients, W. S. Oetting, et al, *J. Invest. Dermatol.* 97, 15(1991). The naturally processed peptide YMDGTMSQV (SEQ ID NO:9) was identified in HLA-A2.1 associated peptides extracted from two melanoma cell lines DM6 and DM93, A. Cox, et al., unpublished results, and the tyrosinase genes in these cell lines have not been sequenced. Another possibility is that this peptide originates from a gene distinct from tyrosinase. Finally, the naturally processed peptide could arise from the genetically encoded tyrosinase sequence through post-translational modification. To distinguish among these hypotheses, mass spectrometry was used to analyze the HLA-A2.1 associated peptides extracted from the melanoma cell line NA8Mel, which does not express a tyrosinase gene, and NA8Mel+tyr, which has been transfected with a tyrosinase gene encoding asparagine at position 371. Peptides (SEQ ID NO:9) and (SEQ ID NO:94) molecular masses of 1032 and 1031, respectively. Analysis of the mixture of naturally processed peptides extracted from NA8Mel by microcapillary reversed-phase HPLC failed to detect any species of mass 1031–1032 at greater than 0.17 fmol/3×10$^7$ cells. However, a single major peak, corresponding to peptide(s0 in the mass window 1031–1032, was detected at the level of 200 fmol/3×10$^7$ cells among the peptides extracted from NA8Mel+tyr. This result confirms that an HLA-A2.1 associted peptide of this mass was derived from the tyrosinase gene product. When synthetic (SEQ ID NO:94) was added to the peptide extract, two distinct peaks were detected in this mass range, indicating that the naturally processed peptide did not have this sequence. Furthermore, no signal above background was discernible at the elution prosition of (SEQ ID NO:94) in normal extracts of NA8Mel+tyr, indicating that this tyrosinase gene encoded peptide is nto present among HLA-A2.1 associated peptides. By contrast, the synthetic peptide (SEQ ID NO:9) did co-elute with the naturally occurring tyrosinase peptide from NA8Mel+tyr, suggesting that these peptides were identical.

Proof for this conclusion was provided by obtaining sequence information on the naturally occurring tyrosinase peptide. Collision-activated dissociation (CAD) mass spectra were recorded on (M+H)$^+$ ions of the corresponding peptide methyl esters. The CAD spectrum representing the peptide methyl esters. The CAD spectrum representing the peptide (SEQ ID NO:9), and distinct from that of (SEQ ID NO:94) establishes that the peptide encoded by the tyrosinase gene has been post-translationally modified prior to its presentation by HLA-A2.1 on the surface of these cells.

Creation of the naturally occurring peptide (SEQ ID NO:9) from the genetically encoded sequence involves deamidation of asparagine to aspartic acid, a process that can occur spontaneously in acidic solution. To ensure that this conversion had not occurred during MHC purification and peptide extraction, the antigen processing mutant cell line T2 was pulsed with exogenous (SEQ ID NO:94) and the HLA-A2.1 associated peptides were extracted. Analysis of this extract revealed a single peak in the mass range 1031–1032, corresponding to 5.1 fmol/1.4×10$^7$ cells, which was not detected among peptides extracted from unpulsed T2 cells. Microcapillary, HPLC demonstrated that this peptide co-eluted with synthetic (SEQ ID NO:94). No peak of greater than 0.05 fmol/1.4×10$^7$ cells was observed at the elution position of synthetic (SEQ ID NO:9. Thus, the conversion of aspargine to aspartic acid in the naturaly processed peptide did not occur during the peptide extraction procedure.

These results establish that the naturally occurring peptide corresponding to a tyrosinase epitope is distinct from that previously identified using a genetic method. This modified peptide is recognized by tyrosinase-specific human CTL more effectively than the genetically encoded peptide, and is the only one of these two peptides to be presented by HLA-A2.1 molecules on the cell surface. This also leads to the conclusion that the naturally occurring peptide represents the epitope to which the melanoma specific CTL were originally primed. The only explanation for the presence of the naturally processed species is that it arises via a post-translational modification that results in the conversion of asparagine to aspartic acid.

Nonenzymatic deamidation of unmodified asparagine residues has been documented for a variety of proteins and is frequently associated with the presence of an asparagine-glycine sequence as occurs at positions 371–372 in tyrosinase. However, although the half-lives of deamidation in these proteins and peptides depend on both their sequence and structure, they are generally estimated to be of the order of days to years. (SEQ ID NO:9) could not be detected within peptides extracted from (SEQ ID NO:94) pulsed T2 cells, demonstrating that spontaneous deamidaiton of this peptide did not occur while it was associated with HLA-A2.1 at the cell surface. In addition, complete deamidation of tyrosinase or tyrosinase-encoded peptides intracellularly during the short time required for antigen processing and presentation would be unlikely. Since the two peptides have a similar binding affinity for HLA-A2.1, this mechanism would thus predict that both would be found among the naturally processed peptides associated with this MHC molecule, and that (SEQ ID NO:94) would predominate. Consequently, the failure to detect and significant amount of this peptide, while the quantity of (SEQ ID NO:9) was 1,000 times greater than background, suggests that spontaneous deamidation cannot account for the generation of this peptide epitope.

Alternatively, enzymatic deamidation of asparagine to aspartate could occur through the action of peptide:N-glycanase (PNGase). This enzyme generates an aspartate through hydrolysis of the linkage between complex-type or high-mannose glycans and asparagine during degradation of N-linked glycoproteins, T. Suzuki, et al., *Biochem, Biophys REs. Com.* 194(3), 1124–1130 (1993); T. Suzuki, et al., *J. Biol. Chem.* 269(26), 17611–17618 (1994). A less likely possibility is glycoasparaginase which has similar activity but acts preferentially on free glycoasparagine compared to peptide bound forms, N. N. Aronson, et al., *FASEB* 3, 2615 (1989); V. Kaartinen, et al., *J. Biol. Chem.* 267, 6855 (1992); I. Mononen, et al., *FASEB* 7, 1247 (1993). Tyrosinase is a glycoprotein that contains six potential N-glycosylation sites, V. J. Hearing, et al., *Int. J. Biochem.* 19, 1141 (1987); V. J. Hearing, et al., *Pigment Cell Res.* 2, 75 (1989). One of these includes the asparagine residue at position 371 which has been shown in the present report to undergo post-translational modification to aspartic acid. N-glycosylation of the asparagine residue would protect it from nonenzymatic deamidation. Furthermore, the attachment of a large carbohydrate side chain would more than likely interfere with binding to HLA-A2.1, since this residue acts as a secondary anchor for peptide binding, Y. Chen, et al., *J. Immunol.* 152, 2874 (1994). In either case, these factors woudl result in the absence of the asparagine containing form of this peptide on the cell surface. Given the strong probability that the N reside in (SEQ ID NO:94) is glycosylated, T. Ohkura, et al., *Arch. Biochem. Biophys* 235(1), 63 (1984), it seems most likely that this mechanism accounts for the presentation (SEQ ID nO:9) in association with HLA-A2.1.

It is interesting to consider how this postulated mechanism for post-translational conversion of this residue would fit into the pathway for processing and presentation of class 1 associate peptides. The conventional pathway involves the production of peptides from proteins expressed in the cytosol and subsequent transport into the ER by the TAP proteins. It is generally assumed that peptides derived from the membrane or secreted proteins are produced after these proteins are aberrantly translated in the cytosol, rather than into the ER. However, the generation of an aspartic acid containing peptide by the action of PNGase or glycosylasparaginase would necessitate synthesis of tyrosinase on ER associated ribosomes in order for it to become N-glycosylated. The sequence and location of further processing steps is unknown. PNGase is a soluble protein whose cellular location has not yet been determined, although it has virtually no activity at lysosomal pH. On the other hand, glycoasparaginase is located exclusively in lysosomes and N-glycosylated forms of tyrosinase have been observed in this compartment. In any case, tyrosinase would need to move from the ER to the subcellular compartment containing one of these enzymes to allow generation of the deglycosylated form of the peptide. Given this scenario, it also remains uncertain whether such peptides would be dependent upon the TAP complex for transport into the ER. Interestingly, a peptide epitope derived from the HIV-1 envelope protein was shown to be generated independently of the TAP complex, whereas generation of eptitopes from the transmembrane fusion protein of measles virus, were dependent upon TAP, S. A. Hammond, et al., *Nature* 364, 158–161 (1993); R. S. van Binnendijk, et al., *J. Exp. Med.* 176, 119–128 (1992). Further investigation into the N-glycosylation/N-deglycosylation and the catabolism of tyrosinase should reveal the processes involved in formation of this naturally occurring post-translationally modified tyrosinase epitope and their significance to class 1 antigen presentation. Such a mechanism may be generally applicable to the presentation of both glycosylated and nonglycosylated peptides from membrane bound and secreted proteins.

Example IX

In the present example, we demonstrate that HLA-A3-restricted CTL recognize shared antigens on autologous and allogeneic melanoma cells, including an HLA-A3-restricted peptide derived from Pmel-17/gp100 and one or more peptides not yet identified, but apparently not derived from Pmel-17/gp100. These results support the use of Pmel-17/gp100-directed immunotherapy for patients who are HLA-A3$^+$, and suggest that HLA-A3, like HLA-A2, presents multiple shared melanoma antigens to HLA-A3 restricted CTL.

Materials and Methods

Cell lines and HLA typing: The human melanoma cell lines VMM1, VMM12, VMM18 and VMM34 were derived from patients at the University of Virginia (Charlottesville, Va.). DM6 was provided by Drs. H. F. Seigler and T. L. Darrow at Duke University (Durham, N.C.). SkMel-2 was obtained from the American Type Culture Collection (ATCC, Bethesda, Md.). Immunohistochemical staining of these cell lines with S-100, HMB-45 and vimentin antibodies was characteristic of melanoma, while staining for epithelial membrane antigen and cytokeratin was negative (data not shown). The CV-1 and 143B TK lines used in the propagation of vaccinia virus were also obtained from the ATCC. VMM12-EBV is an Epstein-Barr virus transformed B cell line derived from peripheral blood mononuclear cells (PBMC) of melanoma patient VMM12. Briefly, the PBMC were incubated with filtered supernatant from the EBV producing cell line B-958 for 1 h at 37° C., followed by culture in RPMI 1640 media with 10% fetal calf serum (FCS) and antibiotics, plus a 1:100 dilution of PHA. K562 is an NK-sensitive human erythroleukemia line. T2-A3 (an HLA-A3 transfectant of the antigen-processing-defective mutant human lymphoid cell line, T2) was provided by P. Cresswell. HLA typing was performed by microcytotoxicity assay on autologous lymphocytes (Gentrak). Expression of HLA-A3 by tumor cells was confirmed by staining with the monoclonal antibody (MAb) GAP-A3 provided by P. Cresswell.

Production of Recombinant vaccinia virus Expressing Human Pmel-17

The full-length Pmel-17 cDNA was sub-cloned from pcDNA1/neo (Invitrogen) into a modified pSC11 vector adjacent to the vaccinia. P7.5 early/late promoter using standard recombinant DNA methods. Standard dideoxy sequencing was used to confirm insertion and orientation. A recombinant vaccinia virus expressing the protein encoded by this gene (vac-Pmel-17) was generated using published methods. Briefly, CV-1 cells were infected with the parental WR strain of vaccinia virus and transfected (Lipofectin, Gibco-BRL) with the pSC11.3-Pmel-17 plasmid. Thymidine-kinase negative recombinants were amplified in 143B TK cells in the presence of bromodeoxyuridine (Sigma, St Louis, Mo.). Recombinants with beta-galactosidase activity were isolated and cloned through several rounds of plaque purification. Large-scale stocks were produced, sucrose purified, and titered in CV-1 cells. Generation of melanoma-specific cytotoxic T cells: CTL were generated following the detailed protocols previously reported. Malignant melanoma was resected from lymph nodes of patient VMM18. Nodes were mechanically dissociated and enzymatically digested in Eagle's MEM (GIBCO, Grand Island, N.Y.) containing 2.5% FCS, 0.1% collagenase B (Boehringer Mannheim), 0.002% DNAase (Sigma), penicillin 100 U/ml, streptomycin 100 ug/ml (Pen-Strept, GIBCO) at room temperature. T cell lines were established from the mixture of lymphocytes and tumor obtained from the digests, using a ratio of tumor cells to lymphocytes of 1:1. Cells were cultured in 24-well tissue culture plates (Linbro, Hamden, CT) in RPMI 1640 (Sigma) containing 10% FCS, Pen-Strept, and 20 U/ml rIL-2 (Cetus, Emeryville, Calif.) and were maintained by repeated stimulation with irradiated (10 Gy) fresh cryopreserved autologous tumor cells or with the autologous tumor cell line at a tumor to lymphocyte ratio of 1:10 every 10–12 days. T cell specificity for autologous melanoma was confirmed after 28 days of culture. Melanoma specific T lymphocytes were then expanded by a modification of methods by E. Goulmy (personal communication), by mixing $1\times10^6$ specific T-cells with $5\times10^6$ irradiated (10 Gy) autologous melanoma stimulators and $10\times10^6$ irradiated (10 Gy) allogenic PBL feeders (pooled from at least three donors). The cells were cultured at 37° C. in 80 mls RPMI 1640 containing 10% FCS, Pen-Strept, and 20 U/ml rIL-2 in the edge of an upright T-75 flask (Falcon), set at a 45° angle. After five days 40 ml fresh culture medium was added to the flask which was then placed upright for a further two days. T lymphocytes were harvested and cryopreserved in $2\times10^6$ aliquots in 90% FCS/10% DMSO for use in cytotoxic T cell assays. This method was found to permit significant expansion of T-cell numbers without changing the specificity of the CTL line (data not shown). T cells were evaluated by flow cytometry after staining with fluorescein- or phycoerythrein-conjugated antibodies to CD3, CD4, CD8 and CD16 (GenTrak Inc., Plymouth Meeting, Pa. and Olympus Corp, Lake Success, N.Y.). Multiple CD8$^+$ VMM18 CTL lines were generated following this protocol with consistent results from each. Similar methods were used for generation of CTL lines from other patients, such as VMM12. Cytotoxicity assays: Cell mediated lysis of target cells was determined using a standard 4 h $^{51}$Cr-release assay. Briefly, 51Cr-labeled target cells were plated at $2\times10^3$ cells/well in triplicate on 96-well V-bottom plates (Costar, Cambridge, Mass.) with indicated ratio of effector cells in a final volume of 200 microliters. Wells containing either culture medium or 1M HCl in place of the effector cells served as spontaneous and maximum $^{51}$Cr-release controls, respectively. Plates were centrifuged at 100×g for 3 min and incubated at 37° C. for 4 h, after which 150 microliters of supernatant from each well was counted on a gamma counter (ICN). The percent specific lysis was calculated using the equation: [(experimental release−spontaneous release)/(maximum release−spontaneous release)]×100. Vaccinia infected targets were generated by infecting cells with 50 pfu/cell of appropriate recombinant vaccinia virus at 37° C. for 5 h, prior to $^{51}$Cr-labeling. Antibody blocking assays were performed by incubating $^{51}$Cr-labeled target cells with affinity purified monoclonal antibodies (MAb) for 1 h at 37° C., prior to incubation with effector CTL. The MAbs used included W6/32, specific for a monomorphic determinant on all human class I MHC molecules; L243, specific for a determinant on human DR molecules; and GAP-A3, specific for HLA-A3. For cold target inhibition assays, CTL were incubated with unlabeled (cold) target cells for 1 h at 37° C., prior to addition of $^{51}$Cr-labeled (hot) targets.

Reconstitution with synthetic peptides: Peptide sequences were selected from the reported human sequence of Pmel-17/gp100 based on predicted HLA-A3 binding motifs. These peptides were synthesized by standard Fmoc chemistry using a Gilson model AMS422 peptide synthesizer. Peptides were reconstituted in CTL assay medium (RPMI 1640, 10% FCS, antibiotics) and pre-incubated for 2 h with $2\times10^3$ 51Cr labeled target cells in 100 microliters/well in 96-well plates. Effector cells were added in 100 microliters assay medium for a final effector to target (E:T) ratio of 20:1 and the remainder of the assay was performed as in standard chromium release assays described above. Wells containing peptide and target cells but no CTL were used as controls to rule out toxicity of the peptides themselves. Initial experiments were performed with unpurified synthetic peptides. Biologically active peptides identified at initial screening were then purified to >98% by reversed-phase HPLC on a Vydac C-4 column with 0.05% trifluoroacetic acid:water and an acetonitrile gradient, then re-evaluated in CTL assays.

Isolation of naturally processed HLA-A3 associated peptides. HLA-A3-associated peptides were acid eluted from HLA-A3 molecules affinity-purified from melanoma cells, as previously described for A2-associated peptides. Briefly, VMM18 melanoma cells cultured in cell factories (Nunc, Naperville, Ill.), were washed three times in cold PBS, pelleted, then snap-frozen. Cell pellets were detergent solubilized in 1% CHAPS, 174 mg/ml PMSF, 5 mg/ml aprotinin, 10 mg/ml leupeptin, 16 mg/ml pepstatin A, 33 mg/ml iodoacetamide, 0.2% sodium azide and 0.03 mg/ml EDTA for 1 h at 4° C. After centrifugation at 100,000×g for 1 h at 4° C., the pellet of insoluble proteins was discarded, and the supernatant was filtered (0.2 um), then passed over a protein A-Sepharose column precoated with MAb GAP-A3. HLA-A3 molecules and associated peptides, bound to GAP-A3, were then eluted with 0.2 N acetic acid, pH 2.7, then peptides were dissociated at pH 2.1 by bringing the solution to 10% acetic acid followed by boiling for 5 min. Finally, peptides were centrifuged through Ultrafree-CL 5000-KDa filters (Millipore, Bedford, Mass.) at 2500×g for 5 h. Filtrates containing purified peptides were concentrated using vacuum centrifugation and stored at −80° C.

HPLC fractionation and co-elution of naturally processed and synthetic peptides: Extracted HLA-A3 associated peptides were fractionated by reversed-phase HPLC on a Brownlee narrowbore C-18 Aquapore column (2.1 mm×3 cm, A, 7 mm) and eluted with a 40-minute gradient of 0 to 60% (v/v) acetonitrile/0.085% TFA in 0.1% TFA. Fractions were collected at 1 minute intervals. A synthetic peptide, (SEQ ID NO:98) was eluted under identical conditions to identify its elution point.

Peptide identification and sequencing by mass spectrometry: Isolated peptides were loaded onto a C18 microcapillary column (75m i.d.×12 cm) and gradient-eluted using acetonitrile and 0.1M acetic acid, with the concentration of acetonitrile increasing at 2%/min, into a Finnigan-MAT TSQ-7000 (San Jose, Calif.) triple quadrupole mass spectrometer equipped with an electrospray ion source. For mass spectrometric peptide sequencing, collision activated dissociation (CAD) mass spectra were recorded for m/z 423.

Results

HLA-A3 Restricted Melanoma Specific Human CTL Recognize one or More Commonly Expressed Antigens Cytotoxic T lymphocyte (CTL) lines were generated by repeated co-culture of lymphocytes, originally harvested from a tumor involved lymph node, with fresh or cultured autologous melanoma cells from patient VMM18 in the presence of rIL-2 as described. Several CD3$^+$, CD8$^+$, CD4$^-$ CTL lines were derived, which lysed autologous tumor, whereas there was minimal lysis of the NK target K562, an allogeneic HLA-A3$^+$ EBV-transformed B cell line (VMM12-EBV) or the HLA-A3-melanoma DM6 (FIG. 15A). Lysis of autologous tumor was MHC-class I restricted, based on inhibition with W6/32, a MAb specific for human class I molecules, but not L243, a MAb specific for a determinant on human DR molecules (FIG. 15B). Furthermore, inhibition observed with GAP-A3, a MAb recognizing HLA-A3, demonstrates that the VMM18 CTL recognize one or more peptides presented by HLA-A3 on the surface of the autologous melanoma cells.

Figure 16A:
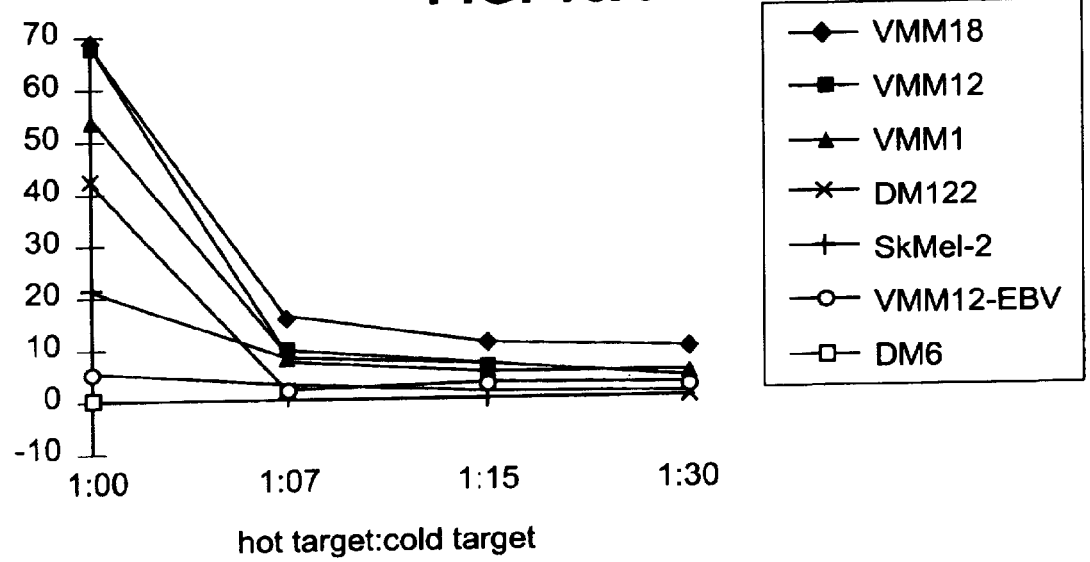
FIG. 16 VMM18 CTL recognize a shared antigen expressed by HLA-A3$^+$ melanomas. Lysis of hot ($^{51}$chromium labeled) autologous and HLA-A3$^+$ allogeneic melanoma cells (see legend) was inhibited by cold (unlabelled) VMM18 melanoma cells (t), but not by cold (unlabelled) HLA-A3$^-$ DM6 melanoma cells (FIG. 16B), 2×10$^4$ VMM18 CTL were incubated with 1.4×10$^4$ unlabelled (cold) VMM18 or DM6 melanoma cells for 1 h at 37° C., prior to the addition of 2×10$^3$ 51Cr-labelled targets as indicated, giving a final E:T ratio of 10:1.
Figure 16B:
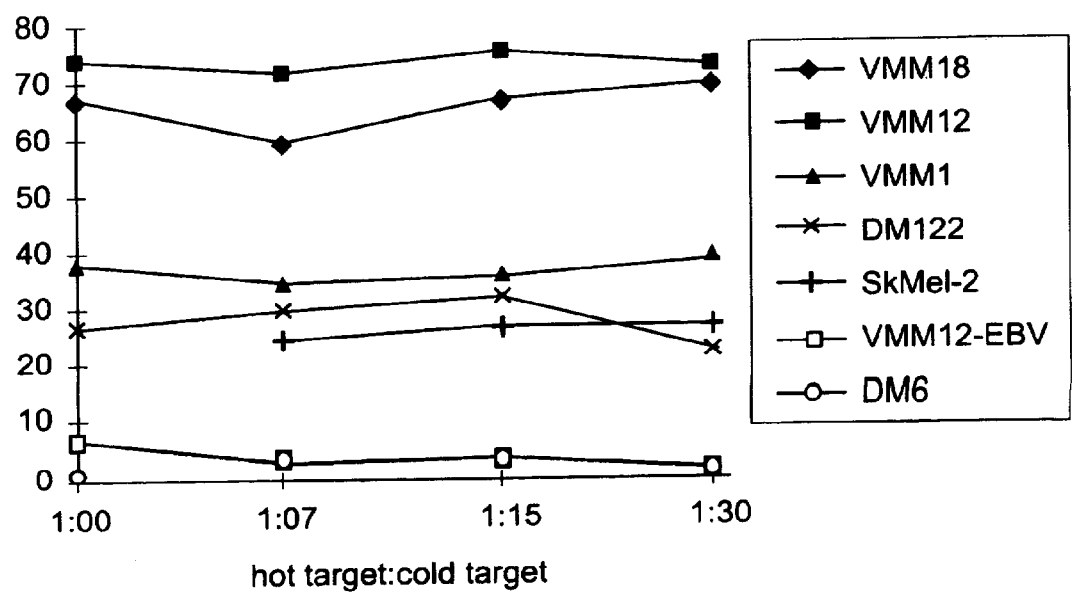

VMM18 CTL lysed several other HLA-A3 matched allogeneic melanomas: VMM1, VMM12, DM122, and SkMel-2, indicating that one or more shared epitope(s) are presented on the surface of multiple HLA-A3$^+$ melanomas (Table 101). In cold target inhibition assays, lysis of allogeneic HLA-A3 matched melanoma cells by VMM18 CTL was inhibited by unlabeled (cold) autologous melanoma cells (VMM18), but not by HLA-A3-melanoma cells (DM6) (FIG. 16). This confirms the existence of shared epitopes restricted by HLA-A3. Lysis of HLA-A3+non-melanoma cells such as the squamous lung cancer cell line SkMes-1 and the lymphoblastoid cell line VMM12-EBV was not observed (Table 101), indicating that these epitopes may be derived from one or more melanoma-specific proteins.

Identification of an HLA-A3 Restricted Peptide from the Melanocyte Differentiation Antigen Pmel-17/gp100

It has been observed that expression by melanoma cells of the melanocyte differentiation antigen Pmel-17 correlates with recognition by HLA-A2 restricted melanoma specific CTL. All of the HLA-A3$^+$ melanoma lines recognized by VMM18 CTL express Pmel-17, as determined by immunohistochemical staining with antibodies HMB-45 and NKIbeteb. Significantly, VMM34 melanoma cells which are also HLA-A3$^+$ but negative for Pmel-17 expression, were not recognized by VMM18 CTL.

Figure 17:
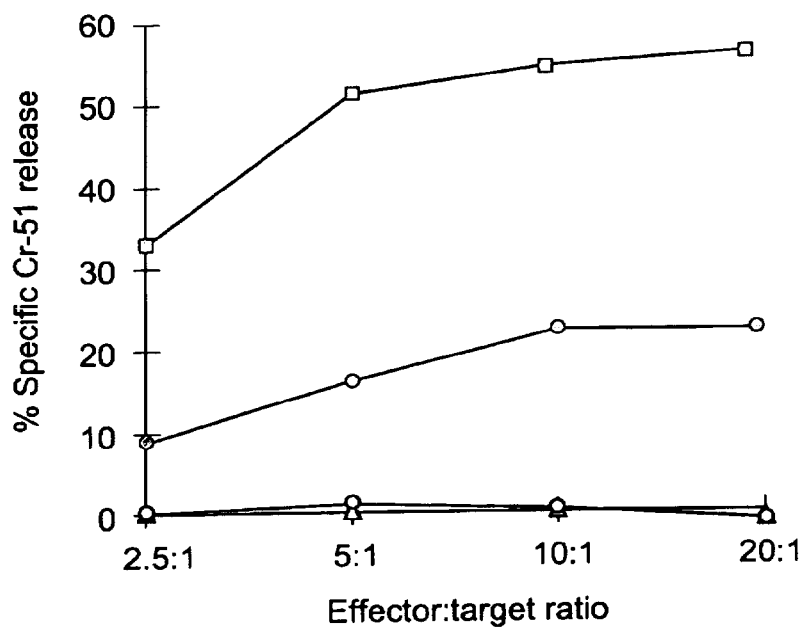
FIG. 17 Expression of Pmel-17 reconstitutes recognition of non-melanoma HLA-A3$^+$ target cells by VMM18 CTL. VMM18 CTL lysed $^{51}$Cr-labeled autologous melanoma cells VMM18 (solid squares) as well as a non-melanoma HLA-A3$^+$ cell line VMM12-EBV infected with recombinant vaccinia virus expressing Pmel-17 (vac-Pmel-17, closed circles). Minimal lysis of uninfected VMM12-EBV cells (open circles), or cells infected with control recombinant vaccinia virus expressing influenza nucleoprotein (vac-NP, open triangles), was observed.

To determine whether Pmel-17 encodes an epitope recognized by HLA-A3 restricted CTL, a recombinant vaccinia virus (vac-Pmel-17) expressing the full-length protein encoded by the Pmel-17 cDNA was constructed. Expression of Pmel-17 by the recombinant vaccinia was confirmed by infecting C1R-A2, an HLA-A2+non-melanoma cell line, with vac-Pmel-17 or an irrelevant recombinant vaccinia encoding the influenza nucleoprotein, NP (vac-NP). Only the vac-Pmel-17 infected cells were lysed by VMM5 CTL, previously demonstrated to recognize an HLA-A2 restricted peptide derived from this antigen (data not shown). When HLA-A3$^+$ VMM12-EBV cells were infected with vac-Pmel-17, they were lysed by VMM18 CTL. Whereas uninfected VMM12-EBV cells, and cells infected with a control recombinant vaccinia virus (vac-NP), were not recognized (FIG. 17). Therefore, expression of Pmel-17/gp100 by VMM12-EBV cells made these cells targets for lysis by VMM18 CTL, suggesting that the CTL recognized a peptide derived from Pmel-17/gp100 and presented by HLA-A3.

Figure 18:
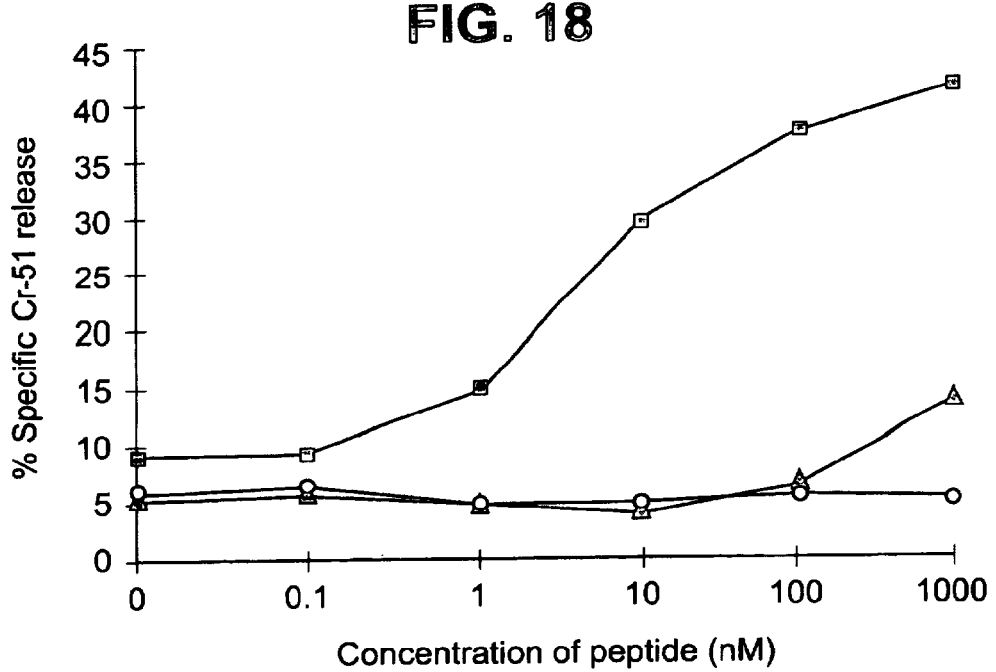
FIG. 18 Relative ability of Pmel-17 peptides to sensitize non-melanoma target cells for recognition by VMM18 CTL. $^{51}$Cr-labelled T2-A3 ells were incubated with Pmel-17 peptides (SEQ ID NO:98)(solid squares and Leu Leu Ala Val Gly Ala Thr Lys (SEQ ID NO:4) triangles) and the control HLA-A3 binding peptide Gln Val Pro Leu Arg Pro Met Thr Tyr Lys (SEQ ID NO:100) from the HIV Nef protein (open circles).

Thirty-four peptides from Pmel-17/gp100 were synthesized on the basis of peptide binding motifs for HLA-A3. These peptides were screened for their ability to sensitize allogeneic HLA-A3$^+$ non-melanoma cells for lysis by VMM18 CTL. Two of these peptides, the nonamer (SEQ ID NO:98) and its amino terminal truncated octamer (SEQ ID NO:4), sensitized VMM12-EBV for lysis by VMM18 CTL (Table 102). The relative ability of these peptides to sensitize targets for lysis was determined in a titration assay using T2-A3, the non-melanoma HLA-A3 transfectant of the antigen processing defective mutant cell line T2. Half maximal lysis was induced with 1–10 nM and >1 um of peptides (SEQ ID NO:98) and (SEQ ID NO:4) respectively, while recognition of the HLA-A3 binding peptide (SEQ ID NO:100; derived from the HIV Nef protein was not observed (FIG. 18). The nonamer peptide was able to sensitize targets for VMM18 CTL recognition at a significantly lower concentration than the octamer, suggesting that it is more likely to be the naturally processed peptide to which the CTL were primed.

The Nonamer Peptide SEQ ID NO: 98 is Naturally Processed and Presented by Melanoma Cells in Association with HLA-A3

To confirm that the HLA-A3 restricted peptide (SEQ ID NO:98) from Pmel-17/gp100 was naturally processed, HLA-A3 associated peptides were isolated from VMM18 melanoma cells and fractionated by reversed-phase HPLC, as described. The synthetic peptide (SEQ ID NO:98) (mass of 846 and m/z of 423) was eluted under identical conditions and found in fraction 14. Collision activated dissociation (CAD) sequencing of the peptide(s) m/z 423 was subsequently performed on the HLA-A3 associated peptides eluted in fraction number 14 from VMM18 melanoma cells, confirming its amino acid sequence as (SEQ ID NO:98); identical to the predicted synthetic peptide. This confirms that peptide (SEQ ID NO:98) Pmel-7/gp100 is a naturally processed antigenic peptide, presented by HLA-A3 on melanoma cells.

Discussion

Evidence of HLA-A3 restricted recognition of melanoma cells by melanoma specific CTL has been previously observed however, melanoma antigens presented by HLA-A3 were not previously identified. In the present report, we have corroborated the previous finding by demonstrating the existence of shared melanoma antigens restricted by HLA-A3. We have also identified a specific naturally-processed peptide, SEQ ID NO:98; derived from Pmel-17, as an epitope recognized by HLA-A3 restricted melanoma specific CTL from patient VMM18. Since this protein, Pmel-17, is expressed by the majority of melanoma cells and is a tissue differentiation antigen of melanocytic origin, this peptide represents a shared epitope for A3-restricted melanoma-specific CTL.

Analysis of HLA-A2 associated peptides eluted from the surface of melanoma cells has demonstrated that the amino acid sequences of naturally processed MHC-associated peptides may differ from their respective gene-encoded amino acid sequences because of post-translational modifications and that the gene-encoded sequence may not be presented at all. To confirm that the predicted peptide; (SEQ ID NO:98), is naturally processed, HLA-A3 associated peptides from VMM18 tumor cells were evaluated directly and sequenced by tandem mass spectrometry. By this method, it has been confirmed that this peptide is naturally processed and presented by HLA-A3.

HLA-A2 and -A3 are two of the most commonly expressed haplotypes in Caucasian populations, representing 46% and 24% respectively. The identification of an HLA-A3 restricted epitope expands the number of patients (to 60%) who might be targeted for immunization against Pmel-17 antigens. It also suggests that Pmel-17 directed immunotherapy may be an important part of immune therapy for melanoma patients of many different haplotypes.

Although the Pmel-17 derived peptide (SEQ ID NO:98) is recognized by VMM18 CTL, it is not recognized by CTL from another patient, VMM12. However, VMM12 CTL do recognize and lyse VMM18 melanoma cells. Because the only Class I MHC molecule shared by VMM12 and VMM18 is HLA-A3, it is evident that at least one additional shared CTL epitope is expressed by both of these tumors.

TABLE 101

Recognition of autologous and allogeneic HLA-A3 + melanoma cell lines by VMM18 CTL.

| Target cell | Cell Type | HLA-A3 expression | Pmel-17 expression | #1 | #2 | #3 |
|---|---|---|---|---|---|---|
| | | | | % Specific Lysis | | |
| VMM18 | Melanoma | + | + | 94 | 88 | 55 |
| VMM12 | Melanoma | + | + | 79 | 66 | 62 |
| VMM1 | Melanoma | + | + | 57 | 57 | 40 |
| DM122 | Melanoma | + | + | 78 | 51 | 39 |
| SkMel-2 | Melanoma | + | + | 52 | 51 | ND |
| VMM12-EBV | Lymphoblastoid | + | − | 3 | 5 | ND |

TABLE 101-continued

Recognition of autologous and allogeneic HLA-A3 + melanoma cell lines by VMM18 CTL.

| Target cell | Cell Type | HLA-A3 expression | Pmel-17 expression | #1 | #2 | #3 |
|---|---|---|---|---|---|---|
| | | | | % Specific Lysis | | |
| K562 | NK target | − | − | 8 | ND | 7 |
| SkMes-1 | Lung CA | + | − | ND | 7 | ND |
| DM6 | Melanoma | − | + | ND | 6 | 6 |

Targets were assayed in triplicate using an E:T ratio of 10:1 in the three representative experiments shown. The known HLA haplotypes of the melanoma lines are as follows: VMM18 (A3, 31, B60, C3); VMM12 (A1, A3, B7, B14); VMM1 (A3, A26, B51); DM122 (A3, A33, B7, B18); SkMel-2 (A3, determined by FACS analysis using MAb GAP-A3); DM6 (A2.1, B12, B13, C1, C2).
ND = Not determined in this experiment.

References for Example IX

1. TRAVERSARI, et al., 1992. Anonapeptide encoded by human gene MAGE-1 is recognized on HLA-A1 by cytolytic T lymphocytes directed against tumor antigen MZ2-E. J. Exp. Med. 176(5).:1453.
2. VAN DEN EYNDE, et al., 1995. Anew family of genes coding for an antigen recognized by autologous cytolytic T lymphocytes on a human melanoma. J. Exp. Med. 182(3):689–98.
3. BRICHARD, et al., 1993. The tyrosinase gene codes for an antigen recognized by autologous cytolytic T lymphocytes on HLA-A2 melanomas. J. Exp. Med. 178(2):489.
4. WOLFEL, et al., 1994 two tyrosinase nonapeptides recognized on HLA-A2 melanomas by autologous cytolytic T lymphocytes. European Journal of Immunology 24:759.
5. ROBBINS, et al., 1994. Recognition of tyrosinase by tumor-infiltrating lymphocytes from a patient responding to immunotherapy [published erratum appears in Cancer Res 1994 Jul. 15;54(14):3952]. Cancer Res. 54(12):3124.
6. SKIPPER, et al., 1995. An HLA-A2 restricted tyrosinase antigen on melanoma cells results from post-translational modification. J. Exp. Med., 183:527–34 (1996).
7. KANG, et al., 1995. Identification of a tyrosinase epitope recognized by HLA-A24-restricted, tumor-infiltrating lymphocytes. J. Immunol. 155(3):1343.
8. COX, et al., 1994. Identification of a peptide recognized by five melanoma-specific human cytotoxic t cell lines. Science 264:716.
9. BAKKER, et al., 1994. Melanoma lineage-specific antigen gp100 is recognized by melanoma-derived tumor-infiltrating lymphocytes. J. Exp. Med. 179:1005.
10. KAWAKAMI, et al., 1994. Identification of a human melanoma antigen recognized by tumor-infiltrating lymphocytes associated with in vivo tumor rejection. Proc. Natl. Acad. Sci. USA 91(14):6458.
11. KAWAKAMI, et al., 1994. Cloning of the gene coding for a shared human melanoma antigen recognized by autologous T cells infiltrating into tumor. Proc. Natl. Acad. Sci. USA 91:3515.
12. COULIE, et al., 1994. A new gene encoding for a differentiation antigen recognized by autologous cytolytic T lymphocytes on HLA-A2 melanomas. J. Exp. Med. 180:35.
13. WANG, et al., 1995. Identification of a gene encoding a melanoma tumor antigen recognized by HLA-A31-restricted tumor-infiltrating lymphocytes [published erratum appears in J Exp Med 1995 mar 1; 181(3):1261]. *J. Exp. Med.* 181(2):799.
14. WOLFEL, et al., 1989. Lysis of human melanoma cells by autologous cytolytic T cell clones. Identification of human histocompatibility leukocyte antigen A2 as a restriction element for three differet antigens. *J. Exp. Med.* 170(3):797.
15. Slingluff, C. L., Jr., A. L. Cox, R. A. Henderson, D. F. Hunt, and V. H. Engelhard. 1993. Recognition of human melanoma cells by HLA-A2.1-restricted cytotoxic T lymphocytes is mediated by at least six shared peptide epitopes. *J. Immunol.* 150(7):2955.
16. COX, et al., 1994. Identification of a peptide recognized by five melanoma-specific human cytotoxic t cell lines. *Science* 264:716.
17. ibid.
18. BAKKER, et al., 1995. Identification of a novel peptide derived from the melanocyte-specific gp100 antigen as the dominant epitope recognized by an HLA-A2.1-restricted anti-melanoma CTL line. *International Journal of Cancer* 62(1):97–102.
19. KAWAKAMI, et al., 1995. Recognition of multiple epitopes in the human melanoma antigen gp100 by tumor-infiltrating T lymphocytes associated with in vivo tumor regression. *Journal of Immunology* 154(8):3961–8.
20. ibid.
21. TRAVERSARI, et al., 1992. Anonapeptide encoded by human gene MAGE-1 is recognized on HLA-A1 by cytolytic T lymphocytes directed against tumor antigen MZ2-E. *J. Exp. Med.* 176(5):1453.
22. GAUGLER, et al., 1994. Human gene MAGE-3 codes for an antigen recognized on a melanoma by autologous cytolytic T lymphocytes. *J. Exp. Med.* 179:921.
23. HAHN, et al., 1991. Presentation of viral antigen to class I major histocompatibility complex-restricted cytotoxic T lymphocyte. Recognition of an immunodominant influenza hemagglutinin site by cytotoxic T lymphocyte is independent of the position of the site in the hemagglutinin translation product. *Journal of Experimental Medicine* 174 (3): 733–6.
24. ibid.
25. SLINGLUFF, et al., 1993. Recognition of human melanoma cells by HLA-A2.1-restricted cytotoxic T lymphocytes is mediated by at least six shared peptide epitopes. *J. Immunol.* 150(7):2955.
26. BARNSTABLE, et al., 1978. Production of monoclonal antibodies to group A erythrocytes, HLA and other human cell surface antigens—new tools for genetic analysis. *Cell.* 14:9.
27. Lampson, L. A., and R. Levy. 1980. Two populations of Ia-like molecules on a human B cell line. *J. Immunol.* 125:293.
28. Berger, A. E., J. E. Davis, and P. Cresswell. 1982. Monoclonal antibody to HLA-A3. *Hybridoma* 1:87.
29. KWON, et al., 1991. A melanocyte-specific gene, Pmel 17, maps near the silver coat color locus on mouse chromosome 10 and is in a syntenic region on human chromosome 12. *Proc. Natl. Acad. Sci. USA* 88:9228.
30. Ruppert, J., R. T. Kubo, J. Sidney, H. M. Grey, and A. Sette. 1994. Class I MHC-peptide interaction: structural and functional aspects. [Review]. *Behring Institute Mitteilungen*::48.
31. DIBRINO, et al., 1993. Endogenous peptides bound to HLA-A3 possess a specific combination of anchor residues that permit identification of potential antigenic peptides. *Proc. Natl. Acad. Sci. USA* 90(4):1508.
32. SLINGLUFF, et al., 1993. Recognition of human melanoma cells by HLA-A2.1-restricted cytotoxic T lymphocytes is mediated by at least six shared peptide epitopes. *J. Immunol.* 150(7):2955.
33. ENGELHARD, et al., 1993. Mass spectrometric analysis of peptides associated with the human class I MHC molecules HLA-A2.1 and HLA-B7 and identification of structural features that determine binding. [Review]. *Chemical Immunology* 57 (39): 39–62.
34. SLINGLUFF, et al., 1993. Recognition of human melanoma cells by HLA-A2.1-restricted cytotoxic T lymphocytes is mediated by at least six shared peptide epitopes. *J. Immunol.* 150(7):2955.
35. COX, et al., 1994. Identification of a peptide recognized by five melanoma-specific human cytotoxic t cell lines. *Science* 264:716.
36. KAWAKAMI, et al., 1993. T-cell recognition of human melanoma antigens. *J. Immunother.* 14:88.
37. BAKKER, et al., 1994. Melanocyte lineage-specific antigen gp100 is recognized by melanoma-derived tumor-infiltrating lymphocytes. *J. Exp. Med.* 179(3):1005.
38. ADEMA, et al., 1993. Melanocyte lineage-specific antigens recognized by monoclonal antibodies NKI-beteb, HMB-50, and HMB-45 are encoded by a single cDNA. *American Journal of Pathology* 143 (6): 1579–85.
39. KWON, et al., 1991. A melanocyte-specific gene, Pmel 17, maps near the silver coat color locus on mouse chromosome 10 and is in a syntenic region on human chromosome 12. *Proc. Natl. Acad. Sci. USA* 88:9228.
40. COX, et al., 1994. Identification of a peptide recognized by five melanoma-specific human cytotoxic t cell lines. *Science* 264:716.
41. KUBO, et al., 1994. Definition of specific peptide motifs for four major HLA-A alleles. *Journal of Immunology* 152 (8): 3913–24.
42. DIBRINO, et al., 1993. Endogenous peptides bound to HLA-A3 possess a specific combination of anchor residues that permit identification of potential antigenic peptides. *Proc. Natl. Acad. Sci. USA* 90(4):1508.
43. Salter, R. D., D. N. Howell, and P. Cresswell. 1985. Genes regulating HLA class I antigen expression in T–B lymphoblast hybrids. *Immunogenetics* 21:235.
44. SLINGLUFF, et al., 1993. Recognition of human melanoma cells by HLA-A2.1-restricted cytotoxic T lymphocytes is mediated by at least six shared peptide epitopes. *J. Immunol.* 150(7):2955.
45. ENGELHARD, et al., 1993. Mass spectrometric analysis of peptides associated with the human class I MHC molecules HLA-A2.1 and HLA-B7 and identification of structural features that determine binding. [Review]. *Chemical Immunology* 57 (39): 39–62.
46. Q. Chen and P. Hersey. 1992. MHC-restricted responses of CD8+ and CD4+ T-cell clones from regional lymph nodes of melanoma patients. *International Journal of Cancer* 51 (2): 218–24.
47. I. O. Ben-Izhak, P. Stark, R. Levy, R. Bergman and C. Lichtig. 1994. Epithelial markers in malignant melanoma. A study of primary lesions and their metastases. *American Journal of Dermatopathology* 16 (3): 241–6.
48. H. M. Grey, J. Ruppert, A. Vitiello, J. Sidney, W. M. Kast, R. T. Kubo and A. Sette. 1995. Class I MHC-peptide interactions: structural requirements and functional implications. [Review]. *Cancer Surveys* 22 (37): 37–49.
49. SKIPPER, et al., 1995. An HLA-A2 restricted tyrosinase antigen on melanoma cells results from post-translational modification. *J. Exp. Med.* in press.

50. HUNT, et al., 1992. Characterization of peptides bound to the class I MHC molecule HLA-A2.1 by mass spectrometry [see comments]. *Science* 255 (5049): 1261–3.
51. COX, et al., 1994. Identification of a peptide recognized by five melanoma-specific human cytotoxic t cell lines. Science 264:716.
52. KAWAKAMI, et al., 1994. Identification of a human melanoma antigen recognized by tumor-infiltrating lymphocytes associated with in vivo tumor rejection. PNAS USA 91(14):6458–62.
53. KAWAKAMI, et al., 1995. Recognition of multiple epitopes in the human melanoma antigen gp100 by tumor-infiltrating T lymphocytes associated with in vivo tumor regression. Journal of Immunology 154(8):3961–8.
54. GAUGLER, et al., 1994. Human gene MAGE-3 codes for an antigen recognized on a melanoma by autologous cytolytic T lymphocytes. J. Exp. Med. 179:921.
55. CELIS, et al., 1994. Induction of anti-tumor cytotoxic T.lymphocytes in normal humans using primary cultures and synthetic peptide epitopes. PNAS USA 91(6):2105.

Example X

A recombinant vaccinia virus has been constructed that was designed to express the full-length tyrosinase protein. Appropriate expression of the tyrosinase protein was confirmed by infecting tyrosinase-negative non-melanoma cells with this newly constructed virus and demonstrating their subsequent recognition by murine tyrosinase specific T cells. Human HLA-A2-positive lymphoblastoid cells (JY) were infected with a recombinant vaccinia virus expressing the full-length tyrosinase protein, labeled, and combined with murine cytolytic T cells specific for the HLA-A2-restricted tyrosinase "D" peptide (SEQ ID NO:9), which were generated in our laboratories. Recognition of the vaccinia encoded tyrosinase was ascertained by measuring target cell lysis in a standard chromium release assay. As expected, uninfected JY, and JY infected with a recombinant vaccinia encoding an irrelevant protein (NP), were not recognized. JY cells pulsed with the "D" peptide and DM6 melanoma cells served as positive controls, demonstrating the lytic potential and specificity of the T cells in this particular assay, as well as the efficacy of the vaccinia construct as a means of inducing expression of tyrosinase in a cell.

A panel of human cytolytic T lymphocytes (CTL) was then screened for recognition of the tyrosinase protein by the same method. One human CTL line, VMM12, was found to specifically recognize tyrosinase. This experiment was performed as above, except that the CTL were derived from patient VMM12, and the tyrosinase-negative non-melanoma human B lymphoblastoid cell line VMM12EBV served as the target cell. Recognition of VMM12 melanoma tumor cells verifies the lytic potential of these CTL. VMM12EBV infected with recombinant vaccinia encoding tyrosinase were recognized and lysed, whereas VMM12EBV infected with a recombinant vaccinia construct encoding an irrelevant protein (NP) were not recognized, demonstrating that the recognition of VMM12EBV infected with vaccinia-tyrosinase was absolutely dependent on expression of the tyrosinase protein.

The specific Major Histocompatability Complex (MHC) molecule recognized by VMM12 CTL in association with the tyrosinase epitope was determined by repeating the previously described experiment using target cells (C1R) expressing individual MHC molecules. Only those targets which shared expression of HLA-A1 with VMM12 were recognized, demonstrating HLA-A1 as the "restriction element". This experiment was also performed as above, except that additional target cells, expressing individual HLA molecules shared with VMM12EBV (A1, A3 & B7), were included. As observed with VMM12EBV infected with irrelevant vaccinia viruses (above), uninfected VMM12EBV and uninfected C1R (non-melanoma) cells were not recognized, as expected. VMM12EBV (which express the HLA-A1, -A3, -B7, and -B14 MHC molecules) infected with the tyrosinase-expressing recombinant vaccinia virus, and VMM12 melanoma tumor cells, were recognized. The only C1R (lymphoid) target cells that were recognized were those that expressed both HLA-A1 and tyrosinase.

Example XI

Identification of a Tyrosinase Epitope Recognized by Human Melanoma-Reactive, HLA-A1 Restricted CTLs Introduction We have identified the peptide (SEQ ID NO:93) (K is N-terminal), from the tyrosinase protein, as an epitope for HLA-A1-restricted melanoma-specific cytotoxic T-lymphocytes (CTL). This work has been done by generating HLA-A1-restricted melanoma-reactive CTL, creating a vaccinia construct encoding the intact human tyrosinase gene, then infecting HLA-A1+ non-melanoma target cells with the vac-tyrosinase construct. In doing so, VMM12 CTL and VMM15 CTL both recognize an HLA-A1-associated peptide derived from tyrosinase. We have since screened a large panel of peptides that we predicted to bind to HLA-A1, from the defined sequence of tyrosinase. The peptide KCDICTDEY, when pulsed onto HLA-A1+ non-melanoma cells (C1R-A1), reconstitutes an epitope for VMM15 CTL. To a lesser extent, two other peptides that are longer than 9-residues, but which contain the entire KCDICTDEY sequence, also reconstitute an epitope for these CTL. None of 116 other peptides tested worked. Thus, we believe this is an epitope which can be used as an immunogen in treating or preventing melanoma in the 20–25% of patients who express HLA-A1.

Cell lines and HLA typing: The human melanoma cell lines VMM1, VMM12, VMM15, VMM18, VMM30 and VMM34 were derived from patients at the University of Virginia (Charlottesville, Va.). Other fresh (uncultured) tumors VMM14 and VMM21 were also prepared from surgical specimens from patients at the University of Virginia. DM6 was provided by Drs. H. F. Seigler and T. L. Darrow at Duke University (Durham, N. C.). Immunohistochemical staining of these cell lines with S-100, HMB-45 and vimentin antibodies was characteristic of melanoma, while staining for epithelial membrane antigen and cytokeratin was negative. The CV-1 and 143B TK lines used in the propagation of vaccinia virus were also obtained from the American Type Culture Collection (ATCC, Bethesda, Md.). VMM12-EBV is an Epstein-Barr virus transformed B cell line derived from peripheral blood mononuclear cells (PBMC) of melanoma patient VMM12. Briefly, the PBMC were incubated with filtered supernatant from the EBV producing cell line B-958 for 1 h at 37° C., followed by culture in RPMI 1640 media with 10' fetal calf serum (FCS) and antibiotics, plus a 1:100 dilution of PHA. K562 is an NK-sensitive human erythroleukemia line. T2-A3 (an HLA-A3 transfectant of the antigen-processing-defective mutant human lymphoid cell line, T2) was provided by P. Cresswell. HLA typing was performed by microcytotoxicity assay on autologous lymphocytes (Gentrak). Expression of HLA-A1 by tumor cells was confirmed by staining with a monoclonal antibody (MAb) from One Lambda.

CTL lines: We have generated human melanoma-specific CTL lines by in vitro stimulation with autologous tumor, from patients whose tumors express melanocytic tissue differentiation antigens and express one or more of the MHC molecules A1, A3, B7, and B8. Methods for CTL generation have been described. (Table 111 and FIG. 19).

Production of Recombinant vaccinia virus Expressing the Human Genes Encoding Melanocytic Tissue Differentiation Antigens:

We have examined class I MHC-associated epitopes for the melanocytic tissue differentiation antigens by using vaccinia constructs for each of the genes Pmel17/gp100, tyrosinase, and MART-1/MelanA. A cDNA clone of the Pmel17 gene (HUMPMEL17-Genbank) was generously provided by S. N. Wagner, Essen, Germany. The tyrosinase gene was provided by Thierry Boon, Brussels. We have PCR cloned out a cDNA clone of the MART-1/Melan-A gene from DM6 melanoma cells. The entire open-reading frame for each of these cDNA's was sub-cloned into a modified pSC11 vector (Ref Hahn JEM 1991) adjacent to the vaccinia P7.5 early/late promoter using standard recombinant DNA methods. Standard dideoxy sequencing was used to confirm insertion and orientation. A recombinant vaccinia virus expressing the protein encoded by this gene (vac-Pmel-17) was generated using published methods (Ref Macket J. Virol 1984). Briefly, CV-1 cells were infected with the parental WR strain of vaccinia virus and transfected (Lipofectin, Gibco-BRL) with the pSCl1.3-Pmel-17 plasmid. Thymidine-kinase negative recombinants were amplified in 143B TK cells in the presence of bromodeoxyuridine (Sigma). Recombinants with beta-galactosidase activity were isolated and cloned through several rounds of plaque purification. Large-scale stocks were produced, sucrose purified, and titered in CV-1 cells.

The resulting recombinant vaccinia viruses were used to infect the lymphoblastoid cell lines C1R-A1, C1R-A2, C1R-A3, C1R-B7, and C1R-B8, where C1R is a human lymphoblastoid line devoid of native expression of HLA-A or HLA-B region molecules, but expressing low levels of HLA-C and MHC Class II molecules. In some cases EBV-transformed B cells with defined MHC expression were used for the infections. This resulted in transient expression of the antigens of interest. These cells were assayed for recognition by CTL in Cr51-release assays. As a negative control, target cells were also infected with a recombinant vaccinia virus with an irrelevant DNA insert (influenza nucleoprotein, NP). Thus, the cell lines listed above permit isolated evaluation of the expression of antigenic peptides in association with the common Class I MHC molecules HLA-A1, A2, A3, B7, and B8.

Evaluating Recognition of Target Cells by CTL.

Reactivity was assessed by cytotoxicity in a 4-hour chromium release assay. Positive controls were the autologous tumor and known cross-reactive tumor lines. A negative control was uninfected C1R-MHC line and a C1R-MHC line transfected with a vaccinia construct expressing influenza nucleoprotein, vac-NP only. Briefly, $^{51}$Cr-labeled target cells were plated at $1-2\times10^3$ cells/well in triplicate on 96-well V-bottom plates (Costar, Cambridge, Mass.) with indicated ratio of effector cells in a final volume of 200 microliters. Wells containing either culture medium or 1M HCl in place of the effector cells served as spontaneous and maximum $^{51}$Cr-release controls, respectively. Plates were centrifuged at 100×g for 3 min and incubated at 37° C. for 4 h, after which 150 microliters of supernatant from each well was counted on a gamma counter (ICN). The percent specific lysis was calculated using the equation: [(experimental release−spontaneous release)/(maximum release−spontaneous release)]×100. Vaccinia infected targets were generated by infecting cells with 50 pfu/cell of appropriate recombinant vaccinia virus at 37° C. for 5 h, prior to $^{51}$Cr-labeling.

Peptide Synthesis and Reconstitution with Synthetic Peptides:

Peptide sequences were selected from the reported human sequence of tyrosinase, based on predicted HLA-A1 binding motifs (see table 10). These peptides were synthesized by standard Fmoc chemistry using a Gilson model AMS422 peptide synthesizer. Peptides were reconstituted in CTL assay medium (RPMI 1640, 10% FCS, antibiotics) and pre-incubated for 2 h with $2\times10^3$ 51Cr labeled target cells in 100 microliters/well in 96-well plates. Effector cells were added in 100 microliters assay medium for a final effector to target (E:T) ratio of 20:1 and the remainder of the assay was performed as in standard chromium release assays described above. Wells containing peptide and target cells but no CTL were used as controls to rule out toxicity of the peptides themselves. Initial experiments were performed with unpurified synthetic peptides. Biologically active peptides identified at initial screening were then purified to >98% by reversed-phase HPLC on a Vydac C-4 column with 0.05% trifluoroacetic acid:water and an acetonitrile gradient, then re-evaluated in CTL assays.

Results

Figure 20A:
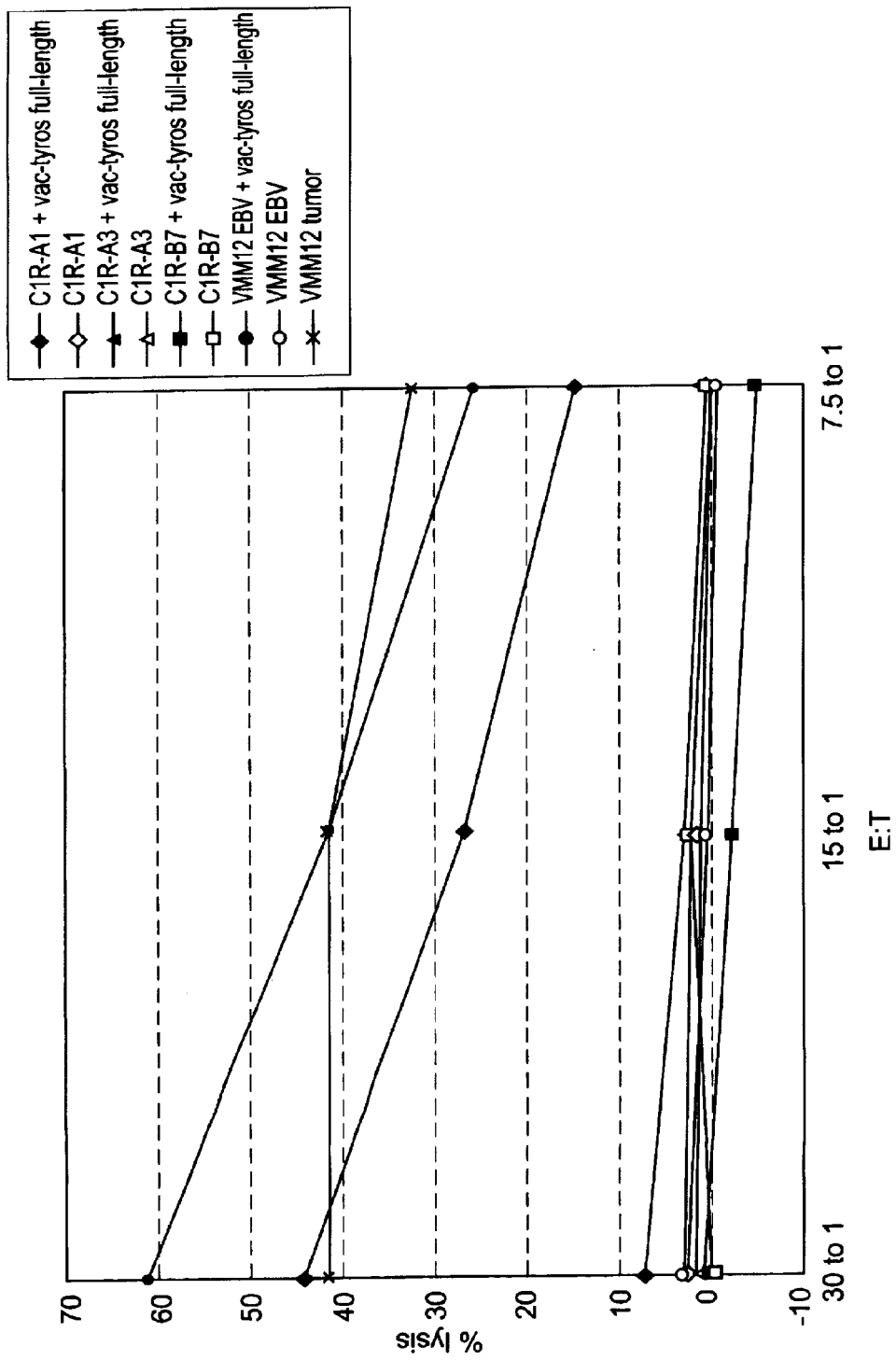
FIG. 20. HLA-A1+CTL lines recognize tyrosinase peptides on HLA-A1. In 20A), VMM12 CTL are capable of lysing C1R-A1 cells infected with a vaccinia-tyrosinase construct. In 20B), VMM15 CTL also recognize tyrosinase.
Figure 20B:
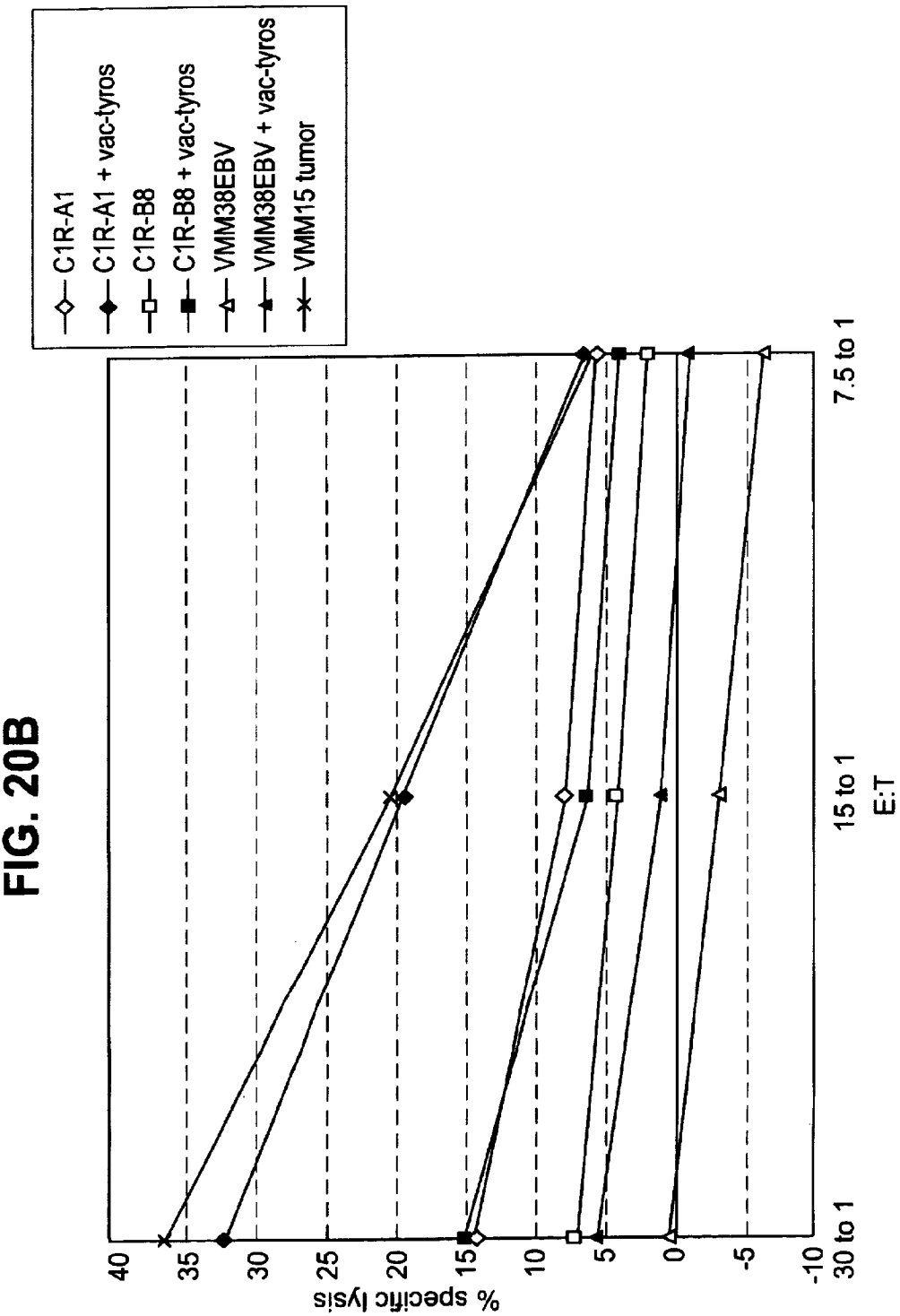

Melanoma-Reactive CTL Lines Recognize MHC-Associated Peptides From Several Melanocytic Differentiation Antigens The CTL lines listed in Table 111 were evaluated for recognition of peptides derived from the 3 melanocytic tissue differentiation antigens listed above, in chromium-release assays, by transient infection with vaccinia constructs encoding those genes. Examples of their reactivity against HLA-matched allogeneic melanomas are shown in FIG. 19. A summary of these results with vaccinia constructs are listed in Table 112 and are shown in FIG. 20. Responses to tyrosinase peptides were observed in half of cases. In addition, responses to MART-1 and gp100 peptides were observed in a smaller set of CTL lines.

At Least Two of the HLA-A1+CTL Lines Recognized Tyrosinase Peptides in an HLA-A1-Restricted Manner.

VMM12 CTL and VMM15 CTL were assayed initially on autologous EBV-B cells as targets. Reactivity against tyrosinase was observed, so additional studies were performed to confirm the reactivity and to determine the MHC restriction (FIG. 20). C1R cells that express selected Class I MHC molecules only were used as target cells. As seen in FIG. 20, C1R-A1 cells infected with vac-tyrosinase are recognized by VMM12 and VMM15 CTL, confirming that one or more tyrosinase-derived peptides are recognized by VMM12 and VMM15 CTL in association with HLA-A1.

The Peptide Representing Residues 243–251 of Tyrosinase Reconstitutes an Epitope for VMM15 CTL.

A set of peptides were synthesized from the defined amino acid sequence of tyrosinase, including 9-mers and longer peptides, with tyrosine (Y) at the C-terminal position and T, S, or M at position 2 and/or D, E, A, or S at position 3 (FIG. 21). These were assayed for their ability to reconstitute epitopes for melanoma-reactive CTL VMM12 and VMM15. C1R-A1 cells were pulsed with the peptide at concentrations ranging from 0.1 to 10 uM in normal assay medium (RPMI+ 10% FCS), then evaluated for recognition in a chromium-release assay. As shown in FIG. 22, three peptides were recognized by VMM15 CTL, all containing the sequence (SEQ ID NO:93) tyrosinase residues 243–251). The most effective, even at the lowest concentration tested, was the 9-mer peptide (SEQ ID NO:93); but also recognized were a ten-mer, (SEQ ID NO:102), and a 13-mer, (SEQ ID NO:101) (FIG. 22).

Figure 23:
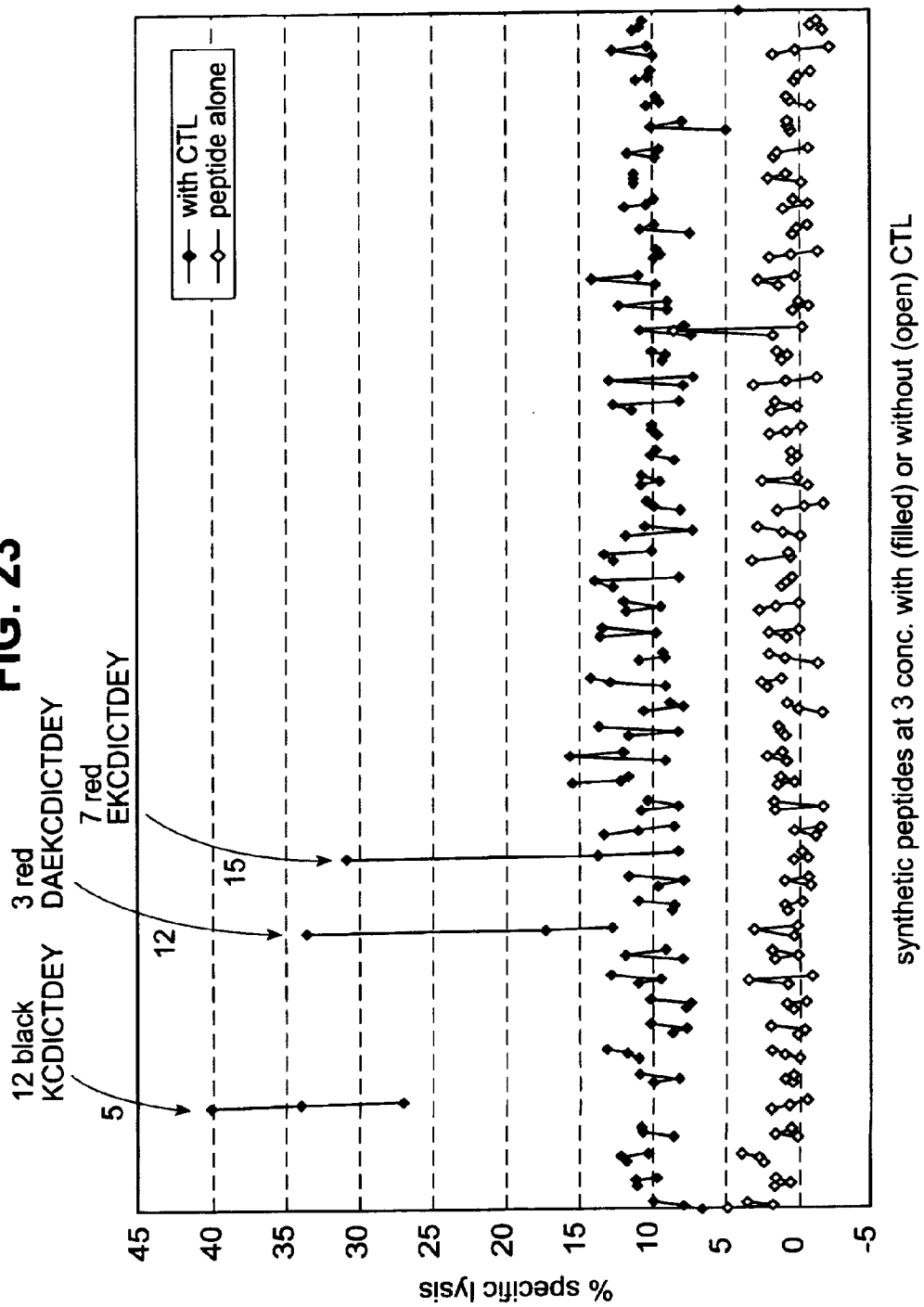
FIG. 23. VMM12 CTL recognize a peptide containing (SEQ ID NO:93) in association with HLA-A1. C1R-A1 cells were pulsed with peptides at 1 to 0.03 uM concentrations prior to adding VMM12 CTL. The peptides themselves were no cytolytic (open diamonds). The peptide of (SEQ ID NO:101) reconstituted an epitope for these VMM12 CTL, although weakly.

Similar reactivity was seen with VMM12 CTL as well, suggesting that (SEQ ID NO:93) a shared antigen on human melanoma cells expressing HLA-A1, against which multiple patients' CTL may be expected to react (FIG. 23). The location of this peptide in the intact protein tyrosinase is shown in FIG. 24.

Discussion

The peptide (SEQ ID NO:93) appears to be recognized by CTL from at least two different patients, in association with HLA-A1. Although longer peptides also are reactive, the dominant response seems to be to (SEQ ID NO:93). This peptide is unusual in its large number of polar amino acid residues, including two aspartic acid residues, one glutamic acid residue, and two cystine residues. The tyrosine residue at position 9 and the aspartic acid at position 3 are important for binding to the MHC. By a computerized system for predicting the binding affinity of individual peptides to HLA-A1 (and other HLA haplotypes), see http://bimas.d-crt.nih.gov:80/cgi-bin/molbio/ken_parker_comboform (The algorithm for this software is discussed in Parker, et al., J. Immunol., 152:163 (1994)), this peptide is predicted to the be the tyrosinase peptide with highest affinity for HLA-A1, which may make it useful for immunization after pulsing on antigen-presenting cells.

One concern with this peptide is the presence of two cystine residues, which may be susceptible to interaction with other sulfhydryl groups on biologic molecules in vitro and in vivo. Studies on the possibility of this interaction and its effect on CTL recognition are underway (SEQ ID NO:93) associated with half-maximal lysis at approximately 1 ug/ml (1 uM). Evaluating the possibility of increasing the potency of this activity is underway, by assessing various amino acid substitutions and their effects on CTL recognition.

There have been two peptides described as epitopes for melanoma-reactive HLA-A1-restricted CTL. They are the MAGE-1 and MAGE-3 peptide (SEQ ID NO:99) and SEQ ID NO:96) these have substantial potential value as immunogens, only a subset of melanoma patients express them. Most other MHC-associated peptide epitopes are HLA-A2 associated. However, HLA-A1 is expressed in approximately 29% of patients in this country. We have previously described an HLA-A3-associated epitope from gp100, (SEQ ID NO:98). Now, with defined peptide epitopes known, it is possible to consider the use of a multivalent peptide vaccine, where all patients expressing either HLA-A1, HLA-A2, or HLA-A3, which is approximately 70% of the patients at risk, may be treated with specific vaccine therapy.

TABLE 111

CTL lines studied for recognition of target cells infected with vaccinia constructs encoding Pmel17/gp100, Tyrosinase, or MART-1/MelanA

| Melanoma Patient ID | Class I MHC expression | Target cell | MHC shared with target | Pmel17-reactive | Tyrosinase-reactive | MART1-reactive |
|---|---|---|---|---|---|---|
| VMM12 | A1, A3, B7, B14 | VMM12-EBV | A1, A3, B7, B14 | 0 | Yes | — |
|  |  | VMM15-EBV | A1 | 0 | Yes | 0 |
|  |  | C1R-A1 | A1 | — | Yes | — |
|  |  | C1R-A3 | A3 | — | 0 | — |
|  |  | C1R-B7 | B7 | — | 0 | — |
| VMM15 | A1, A25, B8, B18 | VMM15-EBV | A1, A25, B8, B18 | 0 | Yes | Yes |
|  |  | C1R-A1 | A1 | — | Yes | — |
|  |  | C1R-B8 | B8 | — | +/− | — |
|  |  | VMM38-EBV | B18 | — | 0 | — |
| VMM10 | A3, A25, B62, C1, C4 | VMM15-EBV | A25 | 0 | +/− | +/− |
|  |  | VMM12-EBV | A3 | 0 | 0 | 0 |
|  |  | VMM16-EBV | C1, C4 | 0 | 0 | 0 |
| VMM30 | A1, A2 B27, B57, C2, C6 | VMM30-EBV | A1, A2 B27, B57, C3 | 0 | Yes | 0 |
| VMM14 | A1, A25, B8, B48 | VMM15-EBV | A1, A25, B8 | 0 | Yes | 0 |
| VMM21 | A1, A2, B7, B37 | VMM21-EBV | A1, A2, B7, B37 | 0 | 0 | Yes |

TABLE III-continued

CTL lines studied for recognition of target cells infected with vaccinia constructs encoding Pmel17/gp100, Tyrosinase, or MART-1/MelanA

| Melanoma Patient ID | Class I MHC expression | Target cell | MHC shared with target | Pmel17-reactive | Tyrosinase-reactive | MART1-reactive |
|---|---|---|---|---|---|---|
| VMM18 | A3, A31/33, B60, C3 | VMM18-EBV | A3, A31/33, B60, C3 | Yes | 0 | Yes |
| | | VMM12-EBV | A3 | Yes | 0 | — |
| | | C1R-A3 | A3 | Yes | — | Yes |
| | | VMM17-EBV | A33? | 0 | — | 0 |
| VMM19 | A24, B35, B55 | VMM19-EBV | A24, B35, B55 | +/− | 0 | 0 |
| DM331 | A1, A2, B15, B62 | VMM12-EBV | A1, A2, B15, B62 | 0 | 0 | — |
| VMM39 | A2, A3, B7, B44 | VMM12-EBV | A3, B7 | 0 | 0 | 0 |
| | | VMM30-EBV | A2 | 0 | 0 | +/− |

— = not tested
+/− = results are equivocal and need further investigation.

TABLE 112

Summary of CTL reactivities observed

| Patient ID | Source of CTL epitope | Restricting Class I MHC molecule |
|---|---|---|
| VMM10 | — | n/a |
| VMM12 | Tyrosinase | A1 |
| VMM14 | Tyrosinase | unknown |
| VMM15 | Tyrosinase | A1 |
| | MART-1 | unknown |
| VMM18 | Pmel17 | A3 |
| | MART-1 | A3 |
| VMM19 | — | n/a |
| VMM21 | MART-1 | unknown |
| VMM30 | Tyrosinase | unknown |
| VMM39 | — | n/a |
| DM 331 | — | n/a |

Remarks

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

For immunological techniques generally, see Coligan, et al, *Current Protocols in Immunology* (NIH: 994); Harlow and Lane, *Antibodies:A laboratory Manual* (Cold Spring Harbor Lab.: 1988).

An immunogen is deemed not to occur in nature, even though its component epitopes do occur in nature, if the immunogen itself, as a single molecule, does not occur in nature. For example, a conjugate of 946L to albumin does not occur in nature even though 946L is a fragment of pMel-17 which is generated by the immune system processing of pMel-17 and complexes with MHC.

The splitter technology described herein may be used in the recovery of CTL epitopes derived from antigens of tumors other than melanomas, or antigens of parasites, viruses, etc. and these epitopes may be used in a similar manner for therapy or diagnosis. The splitter, the dimensions and proportions, and other parameters of the splitter apparatus and of its operation may be altered, provided that such alterations do not substantially interfere with the recovery and identification of CTL epitopes.

What is claimed is:

1. An isolated, HLA-A3 specific peptide consisting of an amino acid sequence set forth in SEQ ID NO: 4 or SEQ ID NO: 98.

2. The isolated peptide of claim 1, wherein said peptide is set forth at SEQ ID NO: 4.

3. The isolated peptide of claim 1, wherein said peptide is set forth at SEQ ID NO: 98.

4. A composition comprising the isolated HLA-A3 specific peptide of claim 1 and an HLA-A2 specific peptide, consisting of the amino acid sequence of SEQ ID NO: 14, SEQ ID NO: 39, or SEQ ID NO: 9.

5. A composition comprising the isolated, HLA-A3 specific peptide of claim 1 and an HLA-A1 specific peptide, the amino acid sequence of which is set forth at SEQ ID NO: 93.

* * * * *